(12) United States Patent
Keane et al.

(10) Patent No.: US 11,840,565 B2
(45) Date of Patent: *Dec. 12, 2023

(54) METHODS AND COMPOSITIONS FOR TREATING VIRUS-ASSOCIATED INFLAMMATION

(71) Applicant: University of Miami, Miami, FL (US)

(72) Inventors: Robert W. Keane, Miami, FL (US); W. Dalton Dietrich, Miami, FL (US); Juan Pablo De Rivero Vaccari, Miami, FL (US); Helen M. Bramlett, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 92 days.

This patent is subject to a terminal disclaimer.

(21) Appl. No.: 17/525,338

(22) Filed: Nov. 12, 2021

(65) Prior Publication Data
US 2022/0153826 A1 May 19, 2022

Related U.S. Application Data

(63) Continuation of application No. 16/856,407, filed on Apr. 23, 2020, now Pat. No. 11,174,307, which is a
(Continued)

(51) Int. Cl.
*A61P 11/00* (2006.01)
*C07K 16/18* (2006.01)
(Continued)

(52) U.S. Cl.
CPC ............ *C07K 16/24* (2013.01); *A61K 31/727* (2013.01); *A61K 39/3955* (2013.01);
(Continued)

(58) Field of Classification Search
None
See application file for complete search history.

(56) References Cited

U.S. PATENT DOCUMENTS

| 8,685,400 | B2 | 4/2014 | Keane et al. |
| 10,537,566 | B2 | 1/2020 | Smith |

(Continued)

FOREIGN PATENT DOCUMENTS

| EA | 019334 B1 | 2/2014 |
| EP | 2145624 A1 | 1/2010 |

(Continued)

OTHER PUBLICATIONS

Masumoto et al., "Murine Ortholog of ASC, a CARD-Containing Protein, Self-Associates and . | Exhibits Restricted Distribution in Developing Mouse Embryos," Experimental Cell Research (2001) 262, 128-133 (Year: 2001).*

(Continued)

*Primary Examiner* — Aurora M Fontainhas
(74) *Attorney, Agent, or Firm* — COOLEY LLP

(57) ABSTRACT

The compositions and methods described herein include methods and agents that inhibit inflammasome signaling in a mammal such as antibodies directed against inflammasome components used alone or in combination with extracellular vesicle uptake inhibitor(s) or other agents. Also described herein are compositions and methods of use thereof for treating viral-associated lung inflammation, for example lung inflammation associated with viral infections such as SARS-CoV-2.

10 Claims, 30 Drawing Sheets

Specification includes a Sequence Listing.

Related U.S. Application Data continuation-in-part of application No. 16/026,482, filed on Jul. 3, 2018, now Pat. No. 10,703,811, which is a continuation-in-part of application No. PCT/US2017/068713, filed on Dec. 28, 2017.

(60) Provisional application No. 62/440,180, filed on Dec. 29, 2016.

(51) Int. Cl.

| | |
|---|---|
| *C07K 16/24* | (2006.01) |
| *A61P 25/28* | (2006.01) |
| *A61P 25/00* | (2006.01) |
| *A61K 39/00* | (2006.01) |
| *A61K 39/395* | (2006.01) |
| *A61P 29/00* | (2006.01) |
| *A61K 31/727* | (2006.01) |
| *A61P 25/14* | (2006.01) |
| *A61P 37/06* | (2006.01) |

(52) U.S. Cl.
CPC ........ *A61K 39/39541* (2013.01); *A61P 11/00* (2018.01); *A61P 25/00* (2018.01); *A61P 25/14* (2018.01); *A61P 25/28* (2018.01); *A61P 29/00* (2018.01); *A61P 37/06* (2018.01); *C07K 16/18* (2013.01); *A61K 2039/505* (2013.01); *A61K 2039/55* (2013.01); *A61K 2039/55522* (2013.01); *C07K 2317/21* (2013.01); *C07K 2317/24* (2013.01); *C07K 2317/34* (2013.01); *C07K 2317/565* (2013.01); *C07K 2317/76* (2013.01)

(56) References Cited

U.S. PATENT DOCUMENTS

| | | | |
|---|---|---|---|
| 10,703,811 | B2 | 7/2020 | Keane et al. |
| 10,961,306 | B2 | 3/2021 | Keane et al. |
| 11,174,307 | B2 | 11/2021 | Keane et al. |
| 2008/0317747 | A1 | 12/2008 | Francisco et al. |
| 2009/0104200 | A1 | 4/2009 | Keane et al. |
| 2010/0150938 | A1 | 6/2010 | Latz et al. |
| 2010/0272714 | A1 | 10/2010 | Acton et al. |
| 2011/0230413 | A1 | 9/2011 | Dhib-Jalbut |
| 2013/0316919 | A1 | 11/2013 | Edomi et al. |
| 2014/0004543 | A1 | 1/2014 | Andres et al. |
| 2014/0286956 | A1 | 9/2014 | Keane et al. |
| 2014/0314746 | A1 | 10/2014 | Artlett et al. |
| 2015/0185232 | A1 | 7/2015 | Keane et al. |
| 2015/0196543 | A1 | 7/2015 | Surber |
| 2016/0178644 | A1 | 6/2016 | Hackney et al. |
| 2016/0263183 | A1 | 9/2016 | Elias et al. |
| 2017/0003303 | A1 | 1/2017 | Keane et al. |
| 2017/0049733 | A1 | 2/2017 | Chen et al. |
| 2017/0107277 | A1 | 4/2017 | Keane et al. |
| 2017/0242043 | A1 | 8/2017 | Bielekova et al. |
| 2019/0002550 | A1 | 1/2019 | Keane et al. |
| 2019/0336598 | A1 | 11/2019 | Keane et al. |
| 2020/0308262 | A1 | 10/2020 | Keane et al. |
| 2020/0333358 | A1 | 10/2020 | de Rivero Vaccari et al. |
| 2020/0347124 | A1 | 11/2020 | Keane et al. |
| 2021/0284723 | A1 | 9/2021 | Keane et al. |
| 2021/0324065 | A1 | 10/2021 | Keane et al. |
| 2022/0169715 | A1 | 6/2022 | Keane et al. |

FOREIGN PATENT DOCUMENTS

| | | | |
|---|---|---|---|
| EP | 2404939 | A2 | 1/2012 |
| KR | 10-2018-0065772 | A | 6/2018 |
| TW | 201338781 | A | 10/2013 |
| WO | WO-9853834 | A1 | 12/1998 |
| WO | WO 2005/111083 | A2 | 11/2005 |
| WO | WO 2006/050280 | A2 | 5/2006 |
| WO | WO-2007038749 | A2 | 4/2007 |
| WO | WO-2007076524 | A2 | 7/2007 |
| WO | WO 2008/106116 | A2 | 9/2008 |
| WO | WO-2011029931 | A1 | 3/2011 |
| WO | WO 2011/143307 | A1 | 11/2011 |
| WO | WO-2013049278 | A1 | 4/2013 |
| WO | WO-2013119673 | A1 | 8/2013 |
| WO | WO 2015/016178 | A1 | 2/2015 |
| WO | WO-2016059571 | A1 | 4/2016 |
| WO | WO-2016182660 | A1 | 11/2016 |
| WO | WO-2018126009 | A1 | 7/2018 |
| WO | WO 2019/060516 | A1 | 3/2019 |
| WO | WO 2020/010273 | A1 | 1/2020 |
| WO | WO 2021/217004 | A2 | 10/2021 |

OTHER PUBLICATIONS

Brown, R.A., et al., "Additional Clinical Benefit of Enoxaparin in COPD Patients Receiving Salmeterol and Fluticasone Propionate in Combination," Pulmonary Pharmacology & Therapeutics, 2006, vol. 19, pp. 419-424.

Wu et. al., "Protective Effects of Asiatic Acid Against Spinal Cord Injury-Induced Acute Lung Injury in Rats" Inflammation, 2016, vol. 39, No. 6, pp. 1853-1861.

Sharma et al., "Biomarkers in Traumatic Brain Injury," Curr Neural Neurosci Rep (2012) 12: 560-569.

Shaw, P.J. et al., "Cutting Edge: Critical Role for PYCARD/ASC in the Development of Experimental Autoimmune Encephalomyelitis," J. Immunol. 2010; 184:4610-4614.

Walle et al., "HMGB1 release by inflammasomes," Virulence, (2011) 2:2, 162-165.

Yatsiv et al., "Elevated Intracranial IL-18 in Humans and Mice After Traumatic Brain Injury and Evidence of Neuroprotective Effects of IL-18-Binding Protein After Experimental Closed Head Injury," Journal of Cerebral Blood Flow & Metabolism, 2002, 22: 971-978.

Abulafia, D. P., et al., "Inhibition of the inflammasome complex reduces the inflammatory response after thromboembolic stroke in mice", Journal of Cerebral Blood Flow & Metabolism (2009); 29(3): 534-544.

Barber, M., et al., "Hemostatic function and progressing ischemic stroke: D-dimer predicts early clinical progression", Stroke (2004); 35(6): 1421-1425.

Biomarkers Definitions Working Group, "Biomarkers and surrogate endpoints: preferred definitions and conceptual framework", Clinical Pharmacology & Therapeutics (2001); 69(3): 89-95.

Brand, F. J., et al., "Acidification changes affect the inflammasome in human nucleus pulposus cells", Journal of Inflammation (2016); 13(29): 1-11.

Brand, F. J., et al., "RIG-I contributes to the innate immune response after cerebral ischemia", Journal of Inflammation (2015); 12(52): 1-7.

Brettschneider, J., et al., "IgG antibodies against measles, rubella, and varicella zoster virus predict conversion to multiple sclerosis in clinically isolated syndrome", PloS One (2009); 4(11):e7638, 1-5.

Bustamante, A., et al.,"Blood/brain biomarkers of inflammation after stroke and their association with outcome: from C-reactive protein to damage-associated molecular patterns", Neurotherapeutics (2016); 13(4): 671-684.

Campos, J. H., et al., "Extracellular vesicles: role in inflammatory responses and potential uses in vaccination in cancer and infectious diseases", Journal of Immunology Research (2015); 2015(832057); 14 pages.

Cao, Y., et al., "Functional inflammatory profiles distinguish myelin-reactive T cells from patients with multiple sclerosis", Science Translational Medicine (2015); 7(287): 287ra74; 11 pages.

Caradec, J., et al., "Reproducibility and efficiency of serum-derived exosome extraction methods", Clinical Biochemistry (2014); 47(13-14): 1286-1292.

Chen, Y., et al., "Serum levels of interleukin (IL)-18, IL-23 and IL-17 in Chinese patients with multiple sclerosis", Journal of Neuroimmunology (2012); 243(1-2): 56-60.

(56) References Cited

OTHER PUBLICATIONS

Compston, A., "The pathogenesis and basis for treatment in multiple sclerosis", Clinical Neurology and Neurosurgery (2004); 106(3): 246-248.

De Rivero Vaccari, J. C., et al., "Mincle signaling in the innate immune response after traumatic brain injury", Journal of Neurotrauma (2015); 32(4): 228-236.

De Rivero Vaccari, J. P., et al., "Estrogen receptor beta signaling alters cellular inflammasomes activity after global cerebral ischemia in reproductively senescence female rats", Journal of Neurochemistry (2016); 136(3): 492-496.

De Rivero Vaccari, J. P., et al., "Therapeutics targeting the inflammasome after central nervous system injury", Translational Research (2016); 167(1); 35-45.

Dujmovic, I., et al., "The analysis of IL-1 beta and its naturally occurring inhibitors in multiple sclerosis: The elevation of IL-1 receptor antagonist and IL-1 receptor type II after steroid therapy", Journal of Neuroimmunology (2009); 207(1-2): 101-106.

Dumas, A., et al., "The inflammasome pyrin contributes to pertussis toxin-induced IL-1β synthesis, neutrophil intravascular crawling and autoimmune encephalomyelitis", PLoS Pathogens (2014); 10(5): e1004150; 14 pages.

Esenwa, C. C., et al., "Inflammatory risk factors, biomarkers and associated therapy in ischaemic stroke", Nature Reviews Neurology (2016); 12(10): 594-604.

Extended European Search Report for European Application No. 18859244.8 dated Aug. 10, 2021, 14 pages.

Extended European Search Report for European Application No. 19831331.4 dated May 23, 2022, 11 pages.

Fann, D. Y., et al., "Evidence that NF-κB and MAPK signaling promotes NLRP inflammasome activation in neurons following ischemic stroke", Molecular Neurobiology (2018); 55: 1082-1096.

Fann, D. Y., et al., "Intravenous immunoglobulin suppresses NLRP1 and NLRP3 inflammasome-mediated neuronal death in ischemic stroke", Cell Death & Disease (2013); 4(9): e790; 10 pages.

Furlan, R., et al., "Caspase-1 regulates the inflammatory process leading to autoimmune demyelination", The Journal of Immunology (1999); 163(5): 2403-2409.

Gao, L., et al., "Detection of IL-10, IL-18 and IFN-γ in Serum of Patients with Multiple Sclerosis", Chinese Journal of Rehabilitation (2008); 23(1): 32-33.

Gris, D., et al., "NLRP3 plays a critical role in the development of experimental autoimmune encephalomyelitis by mediating Th1 and Th17 responses", The Journal of Immunology (2010); 185(2): 974-981.

Hauser, S. L., et al., "Cytokine accumulations in CSF of multiple sclerosis patients: frequent detection of interleukin-1 and tumor necrosis factor but not interleukin-6", Neurology (1990); 40(11): 1735-1739.

Huang, W., et al., "Increased expression of caspase-1 and interleukin-18 in peripheral blood mononuclear cells in patients with multiple sclerosis", Multiple Sclerosis Journal (2004); 10(5): 482-487.

Hurley, J. H., et al., "Membrane budding", Cell (2010); 143(6): 875-887.

Inoue, M., et al., "An interferon-β-resistant and NLRP3 inflammasome-independent subtype of EAE with neuronal damage", Nature Neuroscience (2016); 19(12): 1599-1609.

Inoue, M., et al., "Interferon-β therapy against EAE is effective only when development of the disease depends on the NLRP3 inflammasome", Science Signaling (2012); 5(225): ra38; 9 pages.

Inoue, M., et al., "NLRP3 inflammasome induces chemotactic immune cell migration to the CNS in experimental autoimmune encephalomyelitis", Proceedings of the National Academy of Sciences (2012); 109(26): 10480-10485.

International Preliminary Report on Patentability for International Application No. PCT/US2017/068713 dated Jul. 2, 2019, 6 pages.

International Preliminary Report on Patentability for International Application No. PCT/US2018/051899 dated Mar. 24, 200, 9 pages.

International Preliminary Report on Patentability for International Application No. PCT/US2019/040635 dated Jan. 5, 2021, 7 pages.

International Preliminary Report on Patentability for International Application No. PCT/US2021/028847 dated Nov. 3, 2022, 8 pages.

International Search Report and Written Opinion of the International Searching Authority for International Application No. PCT/US2017/068713, dated Mar. 26, 2018, 9 pages.

International Search Report and Written Opinion of the International Searching Authority for International Application No. PCT/US2018/051899, dated Jan. 28, 2019; 14 pages.

Invitation to Pay Additional Fees issued in PCT/US2018/051899 dated Nov. 19, 2018, 3 pages.

Invitation to Pay Additional Fees issued in PCT/US2019/040635 dated Sep. 23, 2019, 2 pages.

Izquierdo-Useros, N., et al., "HIV and mature dendritic cells: Trojan exosomes riding the Trojan horse?", PLoS pathogens (2010); 6(3): e1000740; 9 pages.

Jarius, S., et al., "Aquaporin-4 antibodies (NMO-IgG) as a serological marker of neuromyelitis optica: a critical review of the literature", Brain Pathology (2013); 23(6): 661-683.

Ji, Q., et al., "Increased brain-specific MiR-9 and MiR-124 in the serum exosomes of acute ischemic stroke patients", PloS One (2016); 11(9): 1-14.

Katan, M., et al., "Inflammatory and neuroendocrine biomarkers of prognosis after ischemic stroke", Expert Review of Neurotherapeutics (2011); 11(2): 225-239.

Katsavos, S., et al., "Biomarkers in multiple sclerosis: an up-to-date overview", Multiple Sclerosis International (2013); 2013(Article ID 340508); 20 pages.

Kawana, N., et al., "Reactive astrocytes and perivascular macrophages express NLRP3 inflammasome in active demyelinating lesions of multiple sclerosis and necrotic lesions of neuromyelitis optica and cerebral infarction", Clinical and Experimental Neuroimmunology (Nov. 2013); 4: 296-304.

Keane, R. W., et al., "Inflammasome proteins as biomarkers of multiple sclerosis", Frontiers in Neurology (2018); 9(135); 9 pages.

Kourembanas, S., "Exosomes: vehicles of intercellular signaling, biomarkers, and vectors of cell therapy", Annual Review of Physiology (2015); 77: 13-27.

Kuhle, J., et al., "Conversion from clinically isolated syndrome to multiple sclerosis: a large multicentre study", Multiple Sclerosis Journal (2015); 21(8): 1013-1024.

Le Pecq, J., "Dexosomes as a therapeutic cancer vaccine: from bench to bedside", Blood Cells, Molecules, and Diseases (2005); 35(2): 129-135.

Li, L., et al., "Research progress on the role of NLRP3 inflammasome in the pathogenesis of multiple sclerosis", Guangdong Medical Journal (Feb. 2017); 38(03): 481-483; 8 pages with English machine translation.

Li, S., et al., "Study of the relationship of IL-18 expression and clinical multiple sclerosis", Journal of Neuroscience and Mental Health (2007); 7(6): 419-421.

Losy, J., et al., "IL-18 in patients with multiple sclerosis", Acta Neurologica Scandinavica (2001); 104(3): 171-173.

Lublin, F. D., "New multiple sclerosis phenotypic classification", European Neurology (2014); 72(Suppl. 1): 1-5.

Luga, V., et al., "Exosomes mediate stromal mobilization of autocrine Wnt-PCP signaling in breast cancer cell migration", Cell (2012); 151(7): 1542-1556.

Lévesque, S. A., et al., "Myeloid cell transmigration across the CNS vasculature triggers IL-1β-driven neuroinflammation during autoimmune encephalomyelitis in mice", Journal of Experimental Medicine (2016); 213(6): 929-949.

Ma, Q., et al., "NLRP3 inflammasome contributes to inflammation after intracerebral hemorrhage", Annals of Neurology (2014); 75(2): 209-219.

Maimone, D., et al., "Cytokine levels in the cerebrospinal fluid and serum of patients with multiple sclerosis", Journal of Neuroimmunology (1991); 32(1): 67-74.

Mathivanan, S., et al., "Exosomes: extracellular organelles important in intercellular communication", Journal of Proteomics (2010); 73(10): 1907-1920.

Mendis, S., et al., "Organizational update: the world health organization global status report on noncommunicable diseases 2014;

(56) References Cited

OTHER PUBLICATIONS one more landmark step in the combat against stroke and vascular disease", Stroke (2015); 46(5): e121-e122.
Milo, R., et al., "Revised diagnostic criteria of multiple sclerosis", Autoimmunity Reviews (2014); 13(4-5): 518-524.
Ming, X., et al., "Caspase-1 expression in multiple sclerosis plaques and cultured glial cells", Journal of the Neurological Sciences (2002); 197(1-2): 9-18.
Minkiewicz, J., et al., "Human astrocytes express a novel NLRP2 inflammasome", Glia (2013); 61(7): 1113-1121.
Neumann, S., et al., "Innate immunity and inflammation post-stroke: an α7-nicotinic agonist perspective", International Journal of Molecular Sciences (2015); 16(12): 29029-29046.
Oei, H. S., et al., "Lipoprotein-associated phospholipase A2 activity is associated with risk of coronary heart disease and ischemic stroke: the Rotterdam Study", Circulation (2005); 111(5): 570-575.
Rekker, K., et al., "Comparison of serum exosome isolation methods for microRNA profiling", Clinical Biochemistry (2014); 47(1-2): 135-138.
Rosenson, R. S., et al., "Modulation of oxidative stress, inflammation, and atherosclerosis by lipoprotein-associated phospholipase A2", Journal of Lipid Research (2012); 53(9): 1767-1782.
Stangel, M., et al., "The utility of cerebrospinal fluid analysis in patients with multiple sclerosis", Nature Reviews Neurology (2013); 9(5): 267-276.
Sun, X., et al., "NLRP2 is highly expressed in a mouse model of ischemic stroke", Biochemical and Biophysical Research Communications (2016); 479(4): 656-662.
Taylor, D. D., et al., "Exosome isolation for proteomic analyses and RNA profiling", Serum/Plasma Proteomics: Methods and Protocols (2011); 728: 235-246.
Teunissen, C. E., et al., "Body fluid biomarkers for multiple sclerosis—the long road to clinical application", Nature Reviews Neurology (2015); 11(10): 585-596.
Théry, C., et al., "Exosomes: composition, biogenesis and function", Nature Reviews Immunology (2002); 2(8): 569-579.
Théry, C., et al., "Membrane vesicles as conveyors of immune responses", Nature Reviews Immunology (2009); 9(8): 581-593.
Tintoré, M., et al., "Do oligoclonal bands add information to MRI in first attacks of multiple sclerosis?", Neurology (2008); 70(13 Part 2): 1079-1083.
Tsukada, N., et al., "Tumor necrosis factor and interleukin-1 in the CSF and sera of patients with multiple sclerosis", Journal of the Neurological Sciences (1991); 104(2): 230-234.
Turaj, W., et al., "Increased plasma fibrinogen predicts one-year mortality in patients with acute ischemic stroke", Journal of the Neurological Sciences (2006); 246(1-2): 13-19.
Vella, L. J., et al., "The role of exosomes in the processing of proteins associated with neurodegenerative diseases", European Biophysics Journal (2008); 37: 323-332.
Villar, L. M., et al., "Intrathecal IgM synthesis predicts the onset of new relapses and a worse disease course in MS", Neurology (2002); 59(4): 555-559.
Whiteley, W., et al., "Blood markers for the prognosis of ischemic stroke: a systematic review", Stroke (2009); 40(5): e380-e389.
Xia, J., et al., "Translational biomarker discovery in clinical metabolomics: an introductory tutorial", Metabolomics (2013); 9(2): 280-299.
Xu, X., et al., "The Yin and Yang of innate immunity in stroke", BioMed Research International (2014); 2014(Article ID 807978); 8 pages.
Zhang, L., et al., "Changes of IL-1β, IL-2 and Effects of Methylprednisolone Administration on Cytokines in Serum of Multiple Sclerosis Patients", Journal of Chengde Medical College (2005); 22(02): 93-96.
Zhang, L., et al., "Effect of Methylprednisolone Administration on Cytokines in Serum of Multiple Sclerosis Patients", Chinese Journal of Clinical Neurosciences (2003); 11(4): 391-393.

Zhang, N., et al., "Chrysophanol inhibits NALP3 inflammasome activation and ameliorates cerebral ischemia/reperfusion in mice", Mediators of Inflammation (2014); 2014: 370530;12 pages.
Zhang, Z. G., et al., "Exosomes in stroke pathogenesis and therapy", The Journal of Clinical Investigation (2016); 126(4): 1190-1197.
Adamczak et al., "Pyroptotic neuronal cell death mediated by the AIM2 inflammasome. Journal of cerebral blood flow and metabolism," Journal of Cerebral Blood Flow and Metabolism, (2014) 34, 621-629.
Al-Ansari et al., "Low-Molecular-Weight Heparin Inhibits Hypoxic Pulmonary Hypertension and Vascular Remodeling in Guinea Pigs," Chest, 2007, 132(6), 1898-1905.
Andersson et al., "Introduction: HMGB1 in inflammation and innate immunity," J Intern Med, (2011) 270(4):296-300.
Arend et al., "IL-1, IL-18, and IL-33 families of cytokines," Immunol Rev., Jun. 2008;223:20-38.
Assis-Nascimento et al., "A flow cytometric approach to analyzing mature and progenitor endothelial cells following traumatic brain injury," J Neurosci Methods, (2016) 263, 57-67.
Atkins et al., "Effects of early rolipram treatment on histopathological outcome after controlled cortical impact injury in mice," Neurosci Lett. Jan. 4, 2013;532: 1-6.
Baker et al., "Critical appraisal of animal models of multiple sclerosis," Multiple Sclerosis Journal (2011) 17(6):647-657.
Bayik et al., "Structure, mechanism and therapeutic utility of immunosuppressive oligonucleotides," Pharmacological Research (2016) 105: 216-225.
Behan et al., "The sad plight of multiple sclerosis research (low on fact, high on fiction): critical data to support it being a neurocristopathy," Inflammopharmacology (2010) 18:265-290.
Brambilla et al., "Astrocytes play a key role in EAE pathophysiology by orchestrating in the CNS the inflammatory response of resident and peripheral immune cells and by suppressing remyelination," GLIA, (2014) 62:452-467.
Butt et al., "Acute Lung Injury: A Clinical and Molecular Review," Archives of Pathology & Laboratory Medicine, Apr. 2016, 140(4):345-350.
Chen et al., "Severe Acute Respiratory Syndrome Coronavirus Viroporin 3a Activates the NLRP3 Inflammasome," Front. Microbial., Jan. 2019, 10:50, 9 pages.
Chi et al., "HMGB1 promotes the activation of NLRP3 and caspase-8 inflammasomes via NF-κB pathway in acute glaucoma," Journal of Neuroinflammation, Jul. 30, 2015; 12:137.
Compan et al., "Apoptosis-associated speck-like protein containing CARD forms specks but does not activate caspase-1 in the absence of NLRP3 during macrophage swelling," J Immunol., Feb. 1, 2015; 194(3): 1261-1273.
Couillin et al. IL-1R1/MyD88 Signaling Is Critical for Elastase-Induced Lung Inflammation and Emphysema, The Journal of Immunology, Dec. 2009, 183: 8195-8202.
Cross et al., "Biomarkers in Acute Lung Injury: Insights Into the Pathogenesis of Acute Lung Injury," Crit Care Clin, Apr. 2011; 27(2):355-377.
De Nardo et al., "New Insights into Mechanisms Controlling the NLRP3 Inflammasome and Its Role in Lung Disease," Am J Pathol 2014, 184: 42-54. (Year: 2014).
De Rivero Vaccari et al., "A Molecular Platform in Neurons Regulates Inflammation after Spinal Cord Injury," The Journal of Neuroscience, Mar. 26, 2008, 28(13):3404-3414.
De Rivero Vaccari et al., "Activation and regulation of cellular inflammasomes: gaps in our knowledge for central nervous system injury," Journal of Cerebral Blood Flow and Metabolism, (2014) 34(3):369-375.
De Rivero Vaccari et al., "Exosome-mediated inflammasome signaling after central nervous system injury," J Neurochem., Jan. 2016;136 Suppl 1:39-48.
De Rivero Vaccari et al., "Therapeutic neutralization of the NLRP1 inflammasome reduces the innate immune response and improves histopathology after traumatic brain injury," Journal of Cerebral Blood Flow and Metabolism, Jul. 2009;29(7):1251-1261.
Dolinay, et al. "Inflammasome-regulated Cytokines Are Critical Mediators of Acute Lung Injury," Am J Respir Crit Care Med, 185(11):1225-1234, Jun. 1, 2012.

(56) References Cited

OTHER PUBLICATIONS

Dos Santos et al., "The inflammasome in lung diseases," Am J Physiol Lung Cell Mol Physiol, 2012, 303: L627-L633.
Erickson et al., "Recent trends in acute lung injury mortality: 1996-2005," Crit Care Med, (2009) 37(5): 1574-1579.
Extended European Search Report for European Application No. 17888678.4 dated Dec. 8, 2020, 10 pages.
Faner et al., "The inflammasome pathway in stable COPD and acute exacerbations," ERJ Open Res 2016; 2: 00002-2016, 9 pages.
Fernandes-Alnemri et al., "Assembly, purification, and assay of the activity of the ASC pyroptosome," Methods Enzymol, (2008) 442:251-270.
Franklin et al., "ASC has extracellular and prionoid activities that propagate inflammation," Nat Immunol., Aug. 2014; 15(8): 727-737.
Gavrilin et al., "Inflammasome Adaptor ASC Is Highly Elevated in Lung Over Plasma and Relates to Inflammation and Lung Diffusion in the Absence of Speck Formation," Front. Immunol., Mar. 19, 2020, 11:461, 11 pages.
Gómez Vicente et al., "P04.07 Relapse in a paucisymptomatic form of multiple sclerosis in a patient treated with nivolumab," Neuro Oncol, Oct. 2016; 18(Suppl 4): iv25.
Guo et al., "Inflammasomes: Mechanism of Action, Role in Disease, and Therapeutics," Nature Medicine (2015) 21(7):677-687.
Hay et al., "Blood-Brain Barrier Disruption Is an Early Event That May Persist for Many Years After Traumatic Brain Injury in Humans," J Neuropathol Exp Neurol. (2015) 74(12):1147-1157.
Hendrickson et al., "The acute respiratory distress syndrome following isolated severe traumatic brain injury," J Trauma Acute Care Surg, Jun. 2016;80(6):989-997.
Hoesch et al. "Acute lung injury in critical neurological illness," Critical Care Medicine, 40(2):587-593, Feb. 2012.
Höftberger et al., "Autoimmune encephalitis in humans: how closely does it reflect multiple sclerosis?" Acta Neuropathologica Communications, 2015 3:80, 13 pages.
Holland et al., "The Development of Acute Lung Injury Is Associated with Worse Neurologic Outcome in Patients with Severe Traumatic Brain Injury," J Trauma., 2003; 55:106-111.
Hosseinian et al., "The role of the NLRP3 inflammasome in pulmonary diseases," Ther Adv Respir Dis. 2015, 9(4):188-197.
International Search Report and Written Opinion of the International Searching Authority for International Application No. PCT/US2019/040635, dated Dec. 5, 2019.
Invitation to Pay Additional Fees issued in PCT/US2021/028847 dated Aug. 12, 2021, 3 pages.
Hornung et al., "AIM2 recognizes cytosolic dsDNA and forms a caspase-1-activating inflammasome with ASC," Nature, Mar. 26, 2009; 458(7237):514-518.
Kadota et al., "Extracellular Vesicles in Chronic Obstructive Pulmonary Disease," Int. J. Mol. Sci. 2016, 17, 1801; 16 pages.
Kalsotra et al., "Brain Trauma Leads to Enhanced Lung Inflammation and Injury: Evidence for Role of P4504Fs in Resolution," Journal of Cerebral Blood Flow and Metabolism, (2007) 27(5):963-974.
Kerr et al., "Neural-respiratory inflammasome axis in traumatic brain injury," Experimental Neurology (2020) 323:113080, 8 pages.
Kong et al., "Involvement of NLRP3 inflammasome in rituximab-induced interstitial lung disease: a case report.," Journal of Clinical Pharmacy and Therapeutics, 2014, 39, 691-694 (Year: 2014).
Kovarova et al., "NLRP1-Dependent Pyroptosis Leads to Acute Lung Injury and Morbidity in Mice," J Immunol 2012; 189:2006-2016.
Kuipers et al., "Ventilator-induced Lung Injury Is Mediated by the NLRP3 Inflammasome," Anesthesiology, May 2012, vol. 116, No. 5, 1104-1115.
Kummer et al., "Inflammasome Components NALP 1 and 3 Show Distinct but Separate Expression Profiles in Human Tissues Suggesting a Site-specific Role in the Inflammatory Response," Journal of Histochemistry & Cytochemistry, 2007 55(5): 443-452.
Lam et al., "Time Course of Early and Late Changes in Plasma DNA in Trauma Patients," Clinical Chemistry, Aug. 2003; 49(8):1286-1291.
Lassmann, "Acute disseminated encephalomyelitis and multiple sclerosis," Brain, (Feb. 2010) 133: 317-319.
Lee et al., "Pulmonary Complications in Patients with Severe Brain Injury," Critical Care Research and Practice, 2012, vol. 2012, Article ID 207247, 8 pages.
Li et al., "Cutting Edge: Inflammasome activation by Alum and Alum's adjuvant effect are mediated by NLRP3," J Immunol., Jul. 1, 2008; 181(1): 17-21.
Li et al., "Enoxaparin ameliorates post-traumatic brain injury edema and neurologic recovery, reducing cerebral leukocyte endothelial interactions and vessel permeability in vivo," J Trauma Acute Care Surg, 2015, vol. 79, No. 7, pp. 78-84.
Liu et al., "HMGB1-DNA Complex-induced Autophagy Limits AIM2 Inflammasome Activation through RAGE," Biochem Biophys Res Commun, Jul. 18, 2014; 450(1):851-856.
Liu et al., "Inflammasome-activated gasdermin D causes pyroptosis by forming membrane pores," Nature, Jul. 7, 2016; 535(7610):153-158.
Lu et al., "Novel role of PKR in inflammasome activation and HMGB1 release," Nature, Aug. 30, 2012; 488(7413):670-674.
Luh et al., "Acute lung injury/acute respiratory distress syndrome (ALI/ARDS): the mechanism, present strategies and future perspectives of therapies," Journal of Zhejiang University Science B, 2007 8(1):60-69.
Man et al., "Converging roles of caspases in inflammasome activation, cell death and innate immunity," Nature reviews Immunology (2016) 16(1):7-21.
Man et al., "Regulation of inflammasome activation," Immunol Rev. May 2015; 265(1): 6-21.
Martinon et al., The Inflammasome: A Molecular Platform Triggering Activation of Inflammatory Caspases and Processing of proIL-β, Molecular Cell, vol. 10, 417-426, Aug. 2002.
Masumoto et al., "ASC, a Novel 22-kDa Protein, Aggregates during Apoptosis of Human Promyelocytic Leukemia HL-60 Cells," The Journal of Biological Chemistry, Nov. 26, 1999, vol. 274, No. 48, pp. 33835-33838.
Masumoto et al., "Expression of Apoptosis-associated Speck-like Protein Containing a Caspase Recruitment Domain, a Pyrin N-terminal Homology Domain-containing Protein, in Normal Human Tissues," The Journal of Histochemistry & Cytochemistry, 2001,49(10): 1269-1275.
Masumoto et al., "Murine Ortholog of ASC, a CARD-Containing Protein, Self-Associates and Exhibits Restricted Distribution in Developing Mouse Embryos," Experimental Cell Research (2001) 262, 128-133.
Matute-Bello, et al. "An Official American Thoracic Society Workshop Report: Features and Measurements of Experimental Acute Lung Injury in Animals," American Journal of Respiratory Cell and Molecular Biology, 44(5):725-738, 2011.
Matute-Bello et al., "Science review: apoptosis in acute lung injury," Critical Care (2003) 7(5):355-358.
Miao et al., "Caspase-1-induced pyroptotic cell death," Immunological Reviews, Sep. 2011; 243(1):206-214.
Monsel et al., "Mesenchymal Stem Cell Derived Secretome and Extracellular Vesicles for Acute Lung Injury and Other Inflammatory Lung Diseases," Expert Opinion on Biological Therapy, Jul. 2016; 16(7):859-871.
Müller et al., "Contribution of damage-associated molecular patterns to transfusion-related acute lung injury in cardiac surgery," Blood Transfusion, 2014; 12(3):368-375.
Nicolls et al., "Traumatic brain injury: lungs in a RAGE," Sci Transl Med, (2014) 6(252):252fs234.
Peltz et al., "HMGB1 is markedly elevated within 6 hours of mechanical trauma in humans," Shock, Jul. 2009; 32(1):17-22.
Pfeifer, et al. "Development of a standardized trauma-related lung injury model," J Surg Res, (2015) 196(2):388-394.
Pinkerton et al., "Inflammasomes in the Lung," Molecular Immunology (2017) 86: 44-55.

(56) References Cited

OTHER PUBLICATIONS

Primiano et al., "Efficacy and Pharmacology of the NLRP3 Inflammasome Inhibitor CP-456,773 (CRID3) in Murine Models of Dermal and Pulmonary Inflammation," The Journal of Immunology, 2016, 197: 2421-2433.

Qu et al., "Nonclassical IL-1 beta secretion stimulated by P2X7 receptors is dependent on inflammasome activation and correlated with exosome release in murine macrophages," J Immunol, (2007) 179(3):1913-1925.

Ragaller et al., "Acute lung injury and acute respiratory distress syndrome," Journal of Emergencies, Trauma, and Shock, Jan.-Mar. 2010; 3(1):43-51.

Ransohoff et al., "Animal models of multiple sclerosis: the good, the bad and the bottom line," Nature Neuroscience, Aug. 2012, vol. 15, No. 8, pp. 1074-1077.

Rincon et al., "Impact of acute lung injury and acute respiratory distress syndrome after traumatic brain injury in the United States," Neurosurgery, (2012) 71(4):795-803.

Robbins et al., "Regulation of immune responses by extracellular vesicles," Nature Reviews Immunology, Mar. 2014, vol. 14, pp. 195-208.

Sagulenko et al., "AIM2 and NLRP3 inflammasomes activate both apoptotic and pyroptotic death pathways via ASC," Cell Death and Differentiation (2013) 20, 1149-1160.

Shastri et al., "Non-Anticoagulant Fractions of Enoxaparin Suppress Inflammatory Cytokine Release from Peripheral Blood Mononuclear Cells of Allergic Asthmatic Individuals," PLoS One, Jun. 2015, 10(6): e0128803, 21 pages.

Sigma-Aldrich, "Anti-ASC Antibody, clone 2EI-7," Catalogue No. 04-147, 2020, 4 pages, retrieved from https://www.emdmillipore.com/US/en/product/Anti-ASC-Antibody-clone-2EI-7,MM_NF-04-147?bd=1.

Silverman et al., "The Pannexin 1 Channel Activates The Inflammasome In Neurons And Astrocytes," The Journal of Biological Chemistry (2009) 284(27):18143-18151.

Simbirtev, A. S., "Oytokines in the Pathogenesis of Infectious and Noninfectious Human Diseases," Medical Academic Journal, 2013, vol. 13, No. 3, pp. 18-41 (English abstract only).

Song et al., "Fluorofenidone attenuates pulmonary inflammation and fibrosis via inhibiting the activation of NALP3 inflammasome and IL-1β/IL-1R1/MyD88/NF-κB pathway," J Cell. Mol. Med., vol. 20, No. 11, 2016, pp. 2064-2077.

Stutzmann et al., "Neuroprotective Profile of Enoxaparin, a Low Molecular Weight Heparin, in In Vivo Models of Cerebral Ischemia or Traumatic Brain Injury in Rats: a Review," CNS Drug Reviews, 2002, vol. 8, No. 1, pp. 1-30.

Summers et al., "Traumatic brain injury in the United States: an epidemiologic overview," The Mount Sinai Journal of Medicine, (2009) 76(2):105-110.

't Hart et al., "Modelling of multiple sclerosis: lessons learned in a non-human primate," Lancet Neurology, 2004, 3:588-597.

Taylor et al., "Exosome platform for diagnosis and monitoring of traumatic brain injury," Philosophical Transactions of the Royal Society B, (2014) 369(1652).

Tomura et al., "Effects of therapeutic hypothermia on inflammasome signaling after traumatic brain injury," Journal of Cerebral Blood Flow and Metabolism, (2012) 32(10):1939-1947.

Villegas et al., "Superoxide Dismutase Mimetic, MnTE-2-PyP, Attenuates Chronic Hypoxia-Induced Pulmonary Hypertension, Pulmonary Vascular Remodeling, and Activation of the NALP3 Inflammasome," Antioxidants & Redox Signaling, 2013, 18(14):1753-1764.

Wang et al., "HMGB1 participates in LPS-induced acute lung injury by activating the AIM2 inflammasome in macrophages and inducing polarization of M1 macrophages via TLR2, TLR4, and RAGE/NF-κB signaling pathways," Int J Mol Med. 2020;45(1):61-80.

Ware et al., "The Acute Respiratory Distress Syndrome," New England Journal of Medicine, (2000) 342(18):1334-1349.

Weber, et al., "The HMGB1-RAGE axis mediates traumatic brain injury-induced pulmonary dysfunction in lung transplantation," Sci Transl Med, (2014) 6(252):252ra124.

Wekerle et al., "Animal models of multiple sclerosis," Drug Discovery Today: Disease Models, 2006,3(4):359-367.

Wiklander et al., "Extracellular vesicle in vivo biodistribution is determined by cell source, route of administration and targeting," J Extracell Vesicles, Apr. 20, 2015; 4, 26316.

Woodcock et al., "The role of markers of inflammation in traumatic brain injury," Frontiers in Neurology, (2013) 4:18, 18 pages.

Wu et al., "A novel pathway of cellular activation mediated by antiphospholipid antibody-induced extracellular vesicles," Journal of Thrombosis and Haemostasis, 2015, 13: 1928-1940.

Wu et al., "Activation of NLRP3 inflammasome in alveolar macrophages contributes to mechanical stretch-induced lung inflammationand injury," J Immunol., Apr. 1, 2013; 190(7): 3590-3599.

Wu et al., "Conditional Overexpression of Connective Tissue Growth Factor Disrupts Postnatal Lung Development," American Journal of Respiratory Cell and Molecular Biology, May 2010;42(5):552-563.

Yáñez-Mo, et al. "Biological properties of extracellular vesicles and their physiological functions," J Extracell Vesicles, (2015) 4:27066, 60 pages.

Yasui et al., "Early coagulation events induce acute lung injury in a rat model of blunt traumatic brain injury," American Journal of Physiology Lung Cellular and Molecular Physiology, (2016) 311(1):L74-86.

Zhang et al., "AIM2 Inflammasome Is Critical for Influenza-Induced Lung Injury and Mortality," J Immunol 2017; 198:4383-4393.

Župan et al., "Effects of enoxaparin in the rat hippocampus following traumatic brain injury," Progress in Neuro-Psychopharmacology & Biological Psychiatry (2011) 35: 1846-1850.

Zygun et al., "Non-neurologic organ dysfunction in severe traumatic brain injury," Critical Care Medicine, 33(3):654-660, Mar. 2005.

Atai et al., "Heparin blocks transfer of extracellular vesicles between donor and recipient cells," J Neurooncol. Dec. 2013; 115(3):343-351, 13 pages.

Freeman et al., "The pathogenic role of the inflammasome in neurodegenerative diseases," Journal of Neurochemistry, 136 (Suppl. 1) (2015), 29-38.

International Search Report and Written Opinion of the International Searching Authority for International Application No. PCT/US2021/028847, dated Oct. 29, 2021.

Jiang et al., "Dopamine D1 receptor agonist A-68930 inhibits NLRP3 inflammasome activation and protects rats from spinal cord," Spinal Cord (2016) 54, 951-956.

Kolliputi et al., "The Inflammasome Mediates Hyperoxia-Induced Alveolar Cell Permeability," The Journal of Immunology, 2010, 184: 5819-5826.

Li et al., "Does enoxaparin interfere with HMGB1 signaling after TBI? A potential mechanism for reduced cerebral edema neurologic recovery," J. Trauma Cute Care Surg, 2015, vol. 80, No. 3 pp. 381-389.

Li et al., "Low-molecular-weight heparin reduces hyperoxia-augmented ventilator-induced lung injury via serine/threonine kinase-protein kinase B," Respiratory Research 2011, 12:90, 12 pages.

Luan et al., "Treatment of Low Molecular Weight Heparin Inhibits Systemic Inflammation and Prevents Endotoxin-Induced Acute Lung Injury in Rats," Inflammation, Jun. 2014, vol. 37, No. 3, pp. 924-932.

Mascia, "Acute Lung Injury in Patients with Severe Brain Injury: A Double Hit Model," Neurocrit Care (2009) 11:417-426.

\* cited by examiner

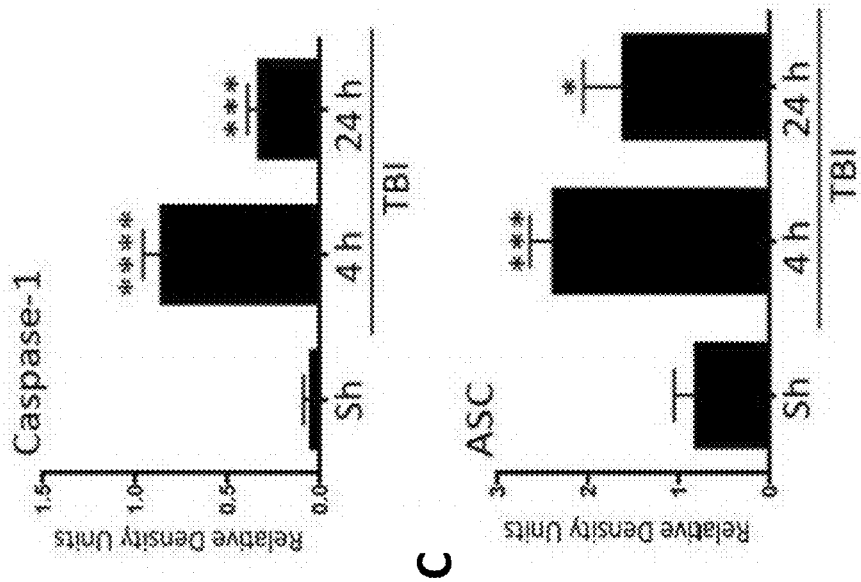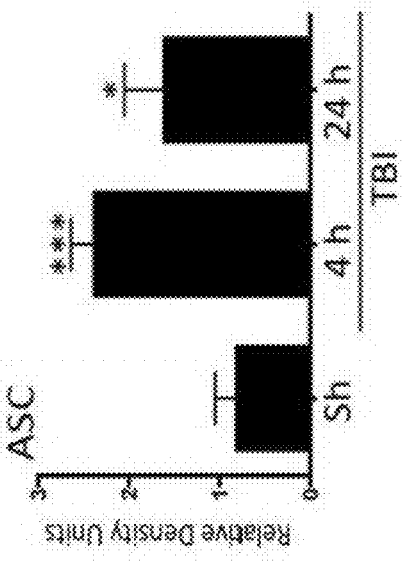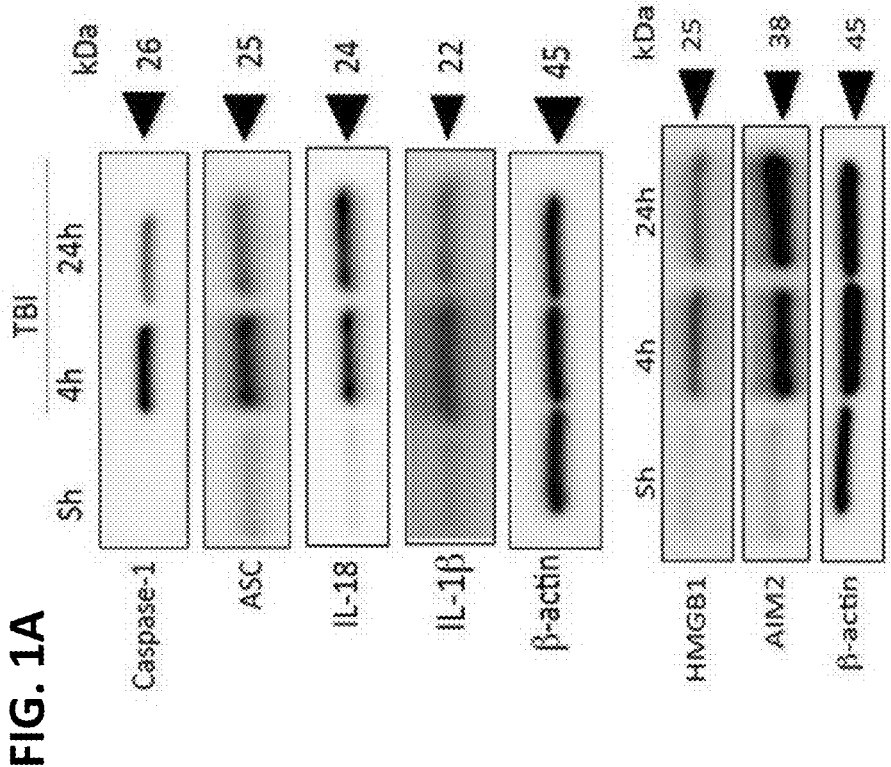

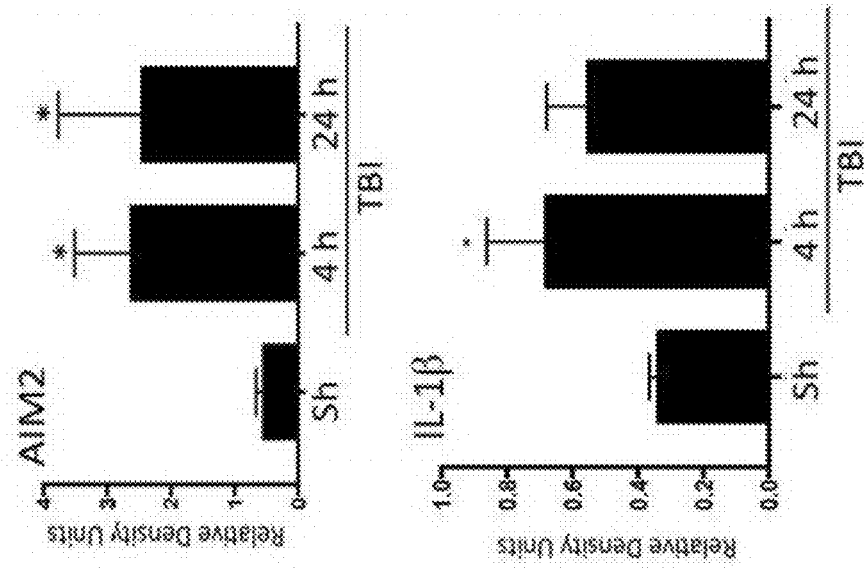
FIG. 1F
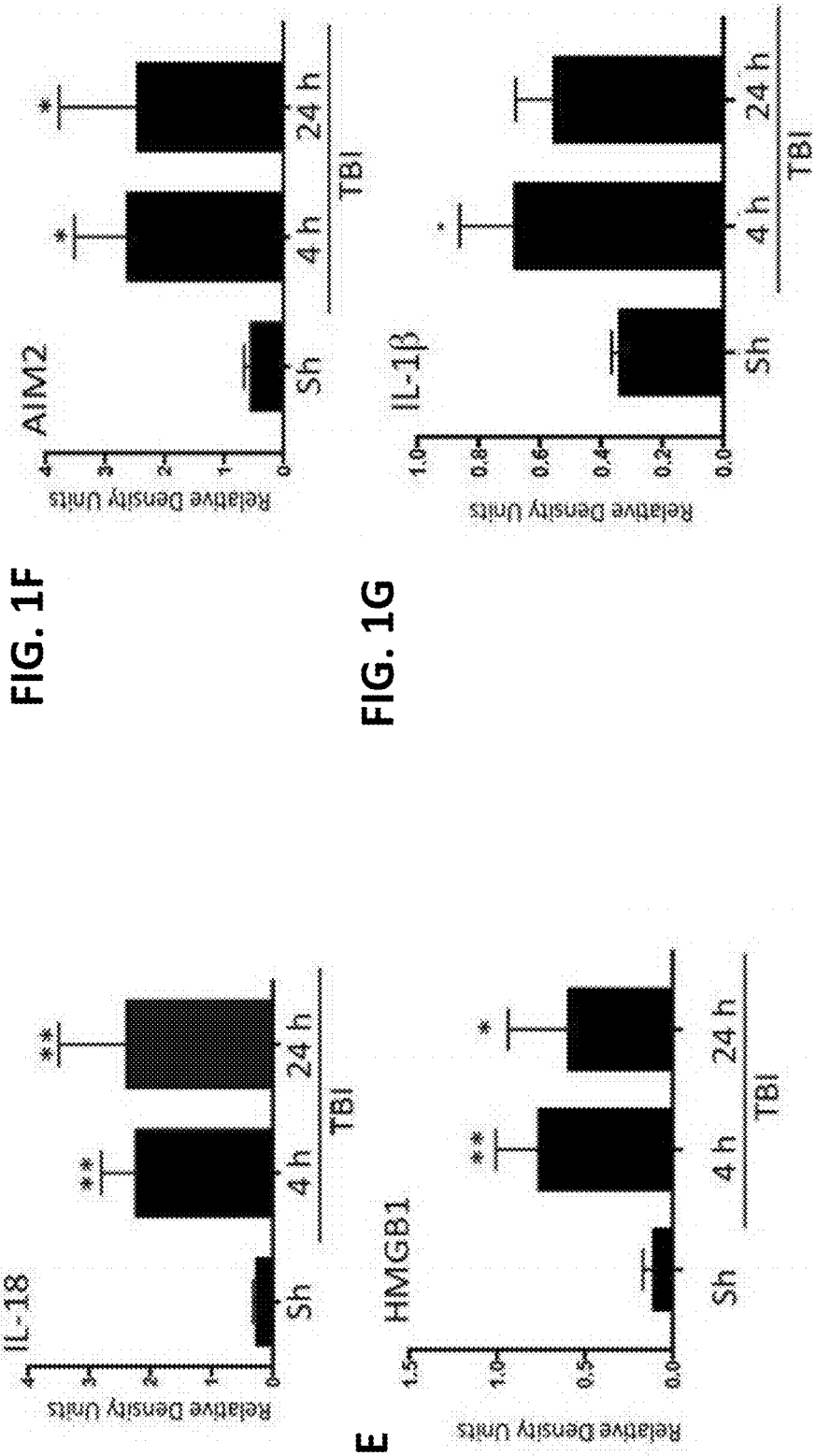
FIG. 1G
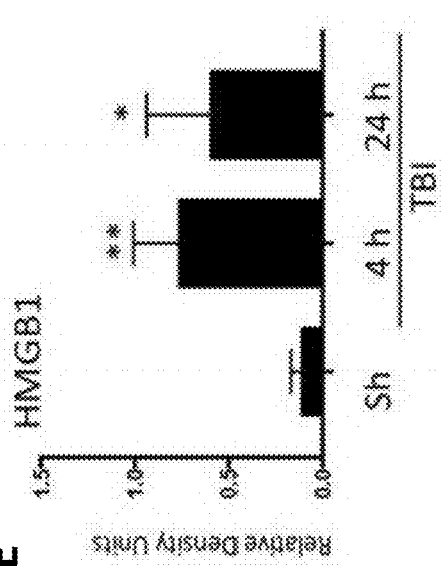
FIG. 1D
FIG. 1E

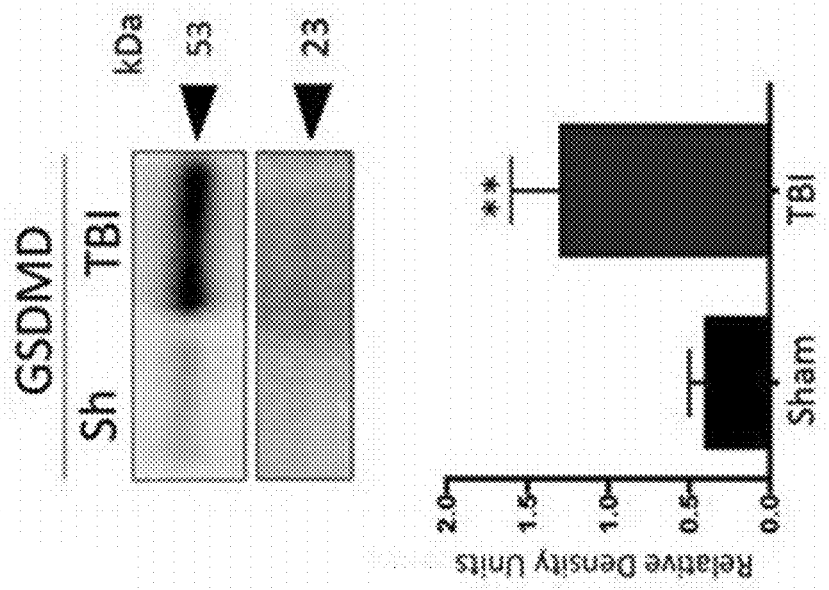
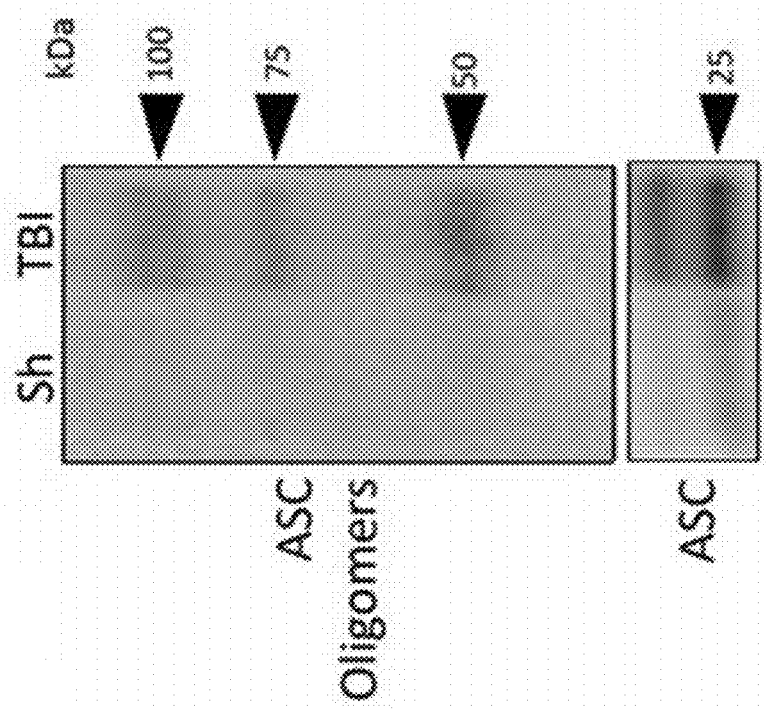
FIG. 4B  FIG. 4C  FIG. 4A

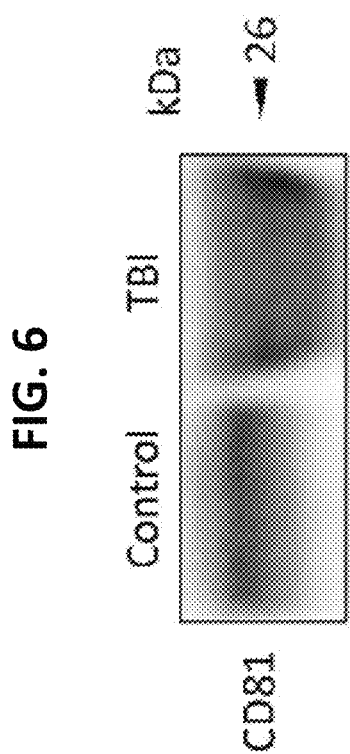

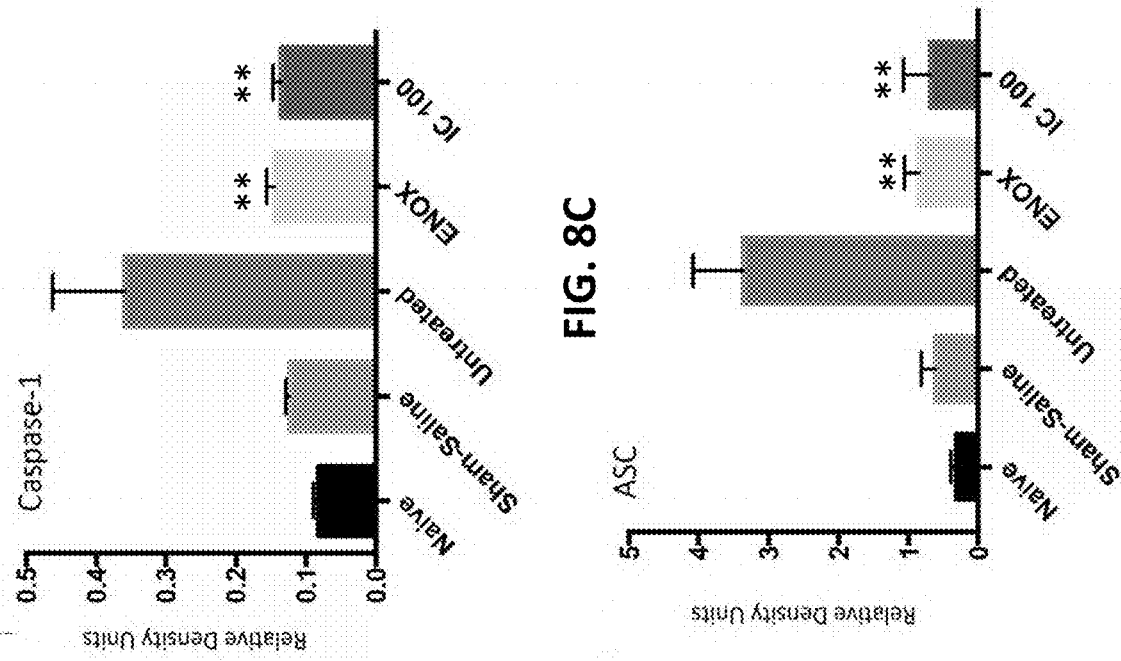
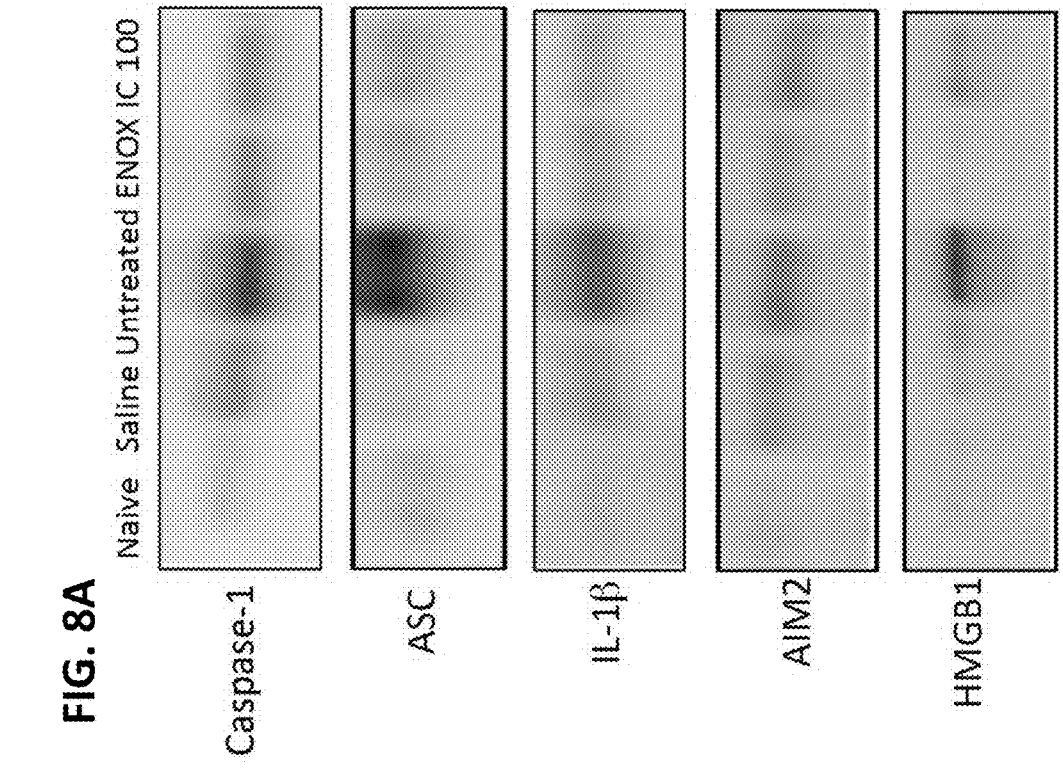

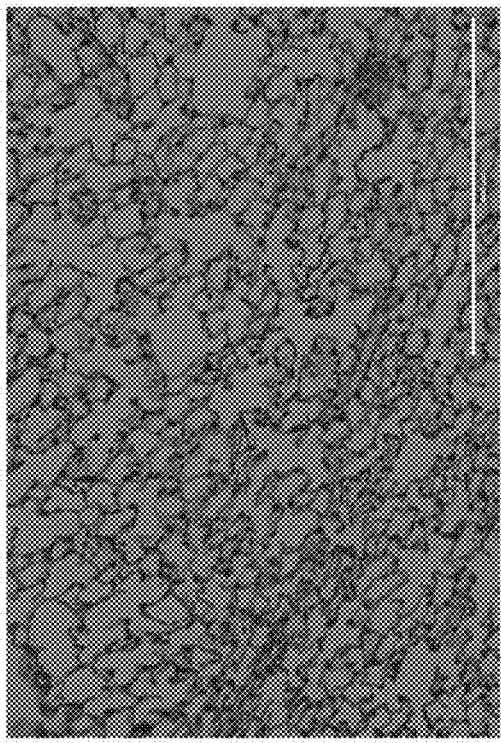
FIG. 9B Untreated
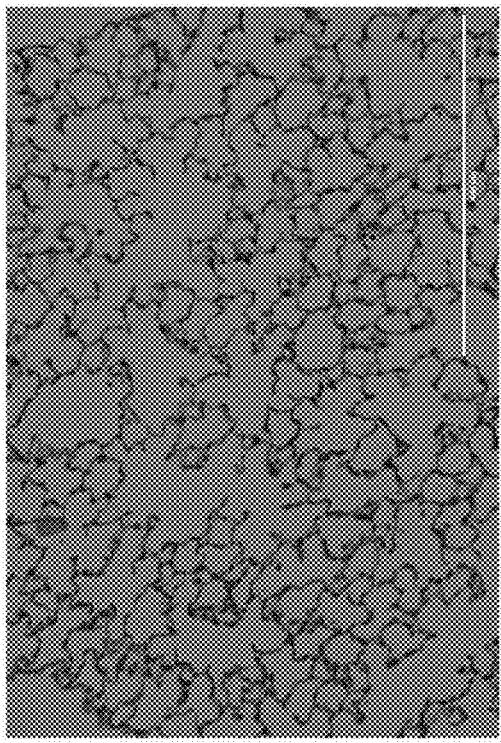
FIG. 9D ANTI-ASC
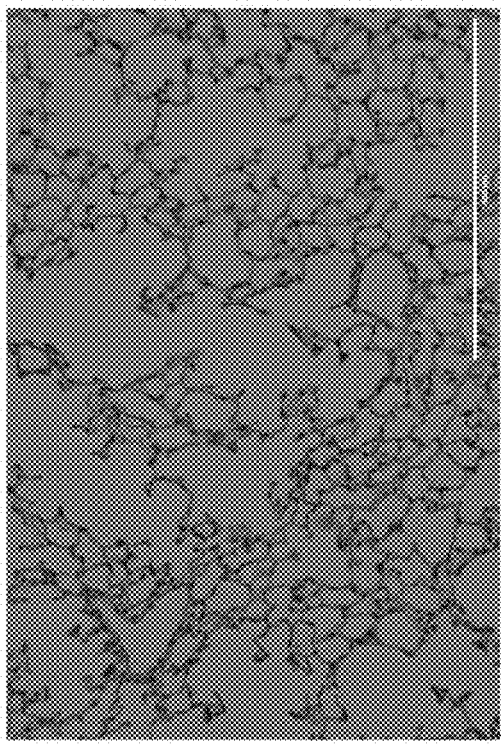
FIG. 9A Sham Vehicle
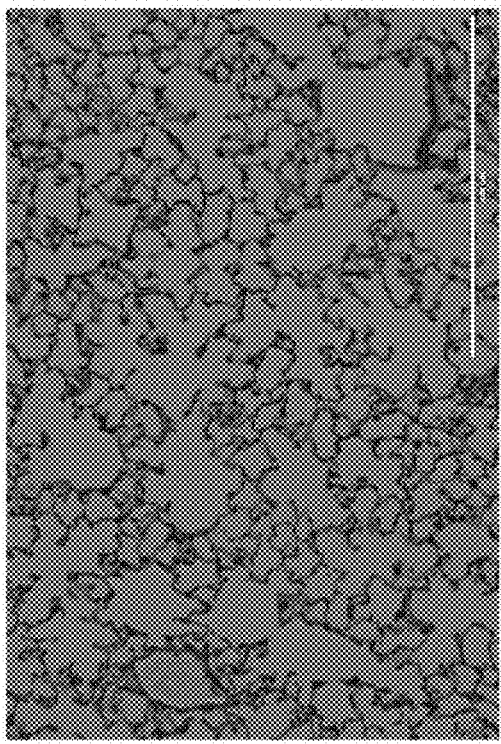
FIG. 9C ENOX

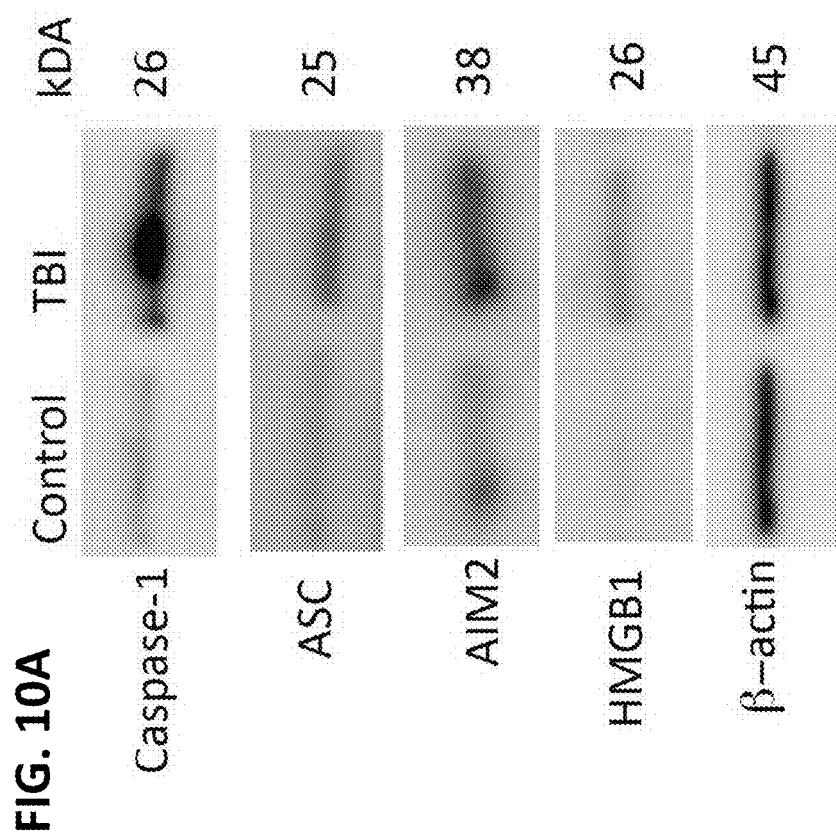
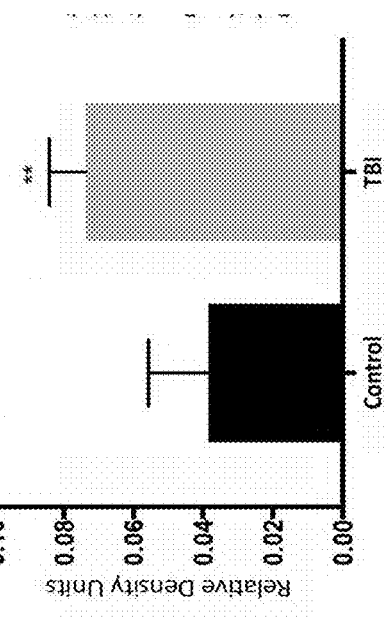
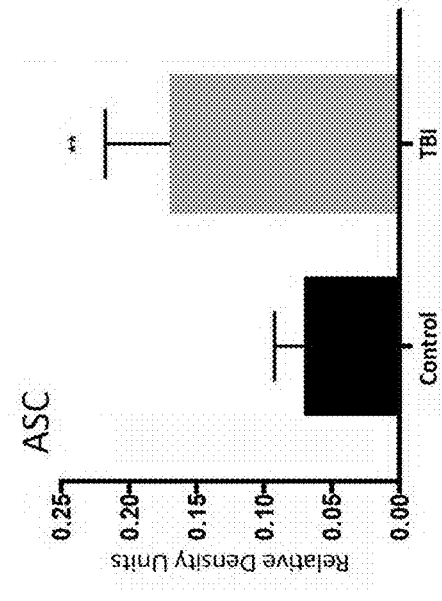
FIG. 10A
FIG. 10B
FIG. 10C

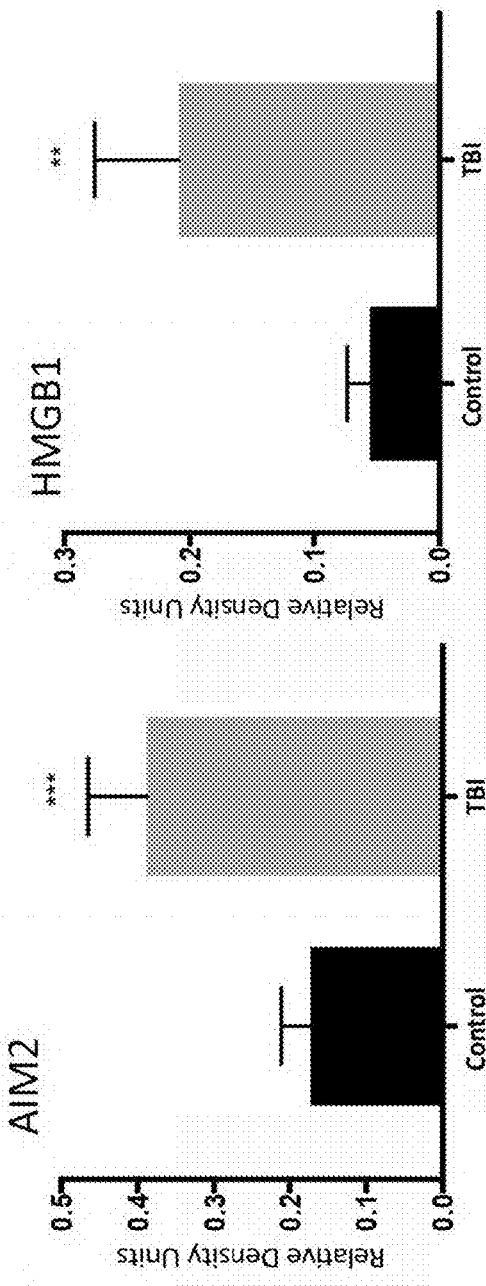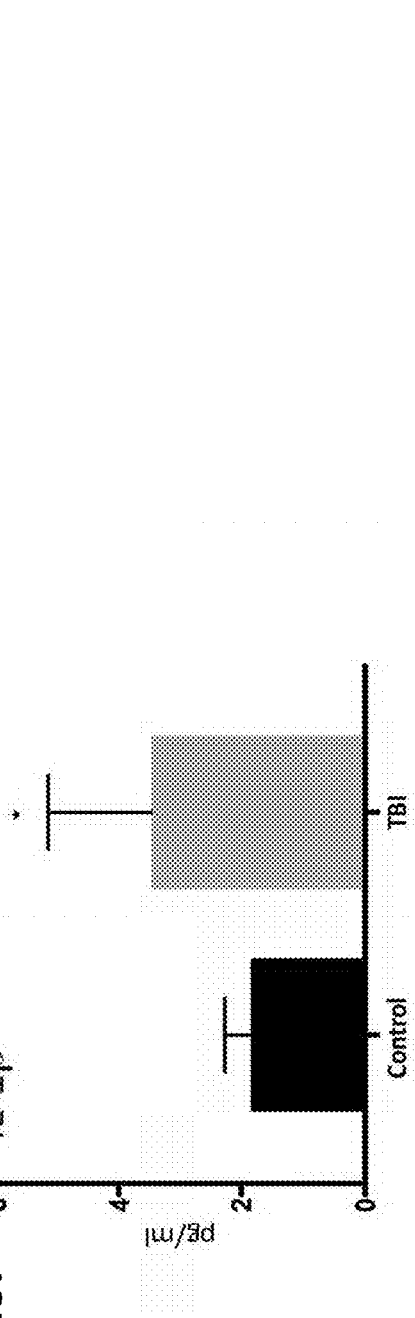
FIG. 10D
FIG. 10E
FIG. 10F

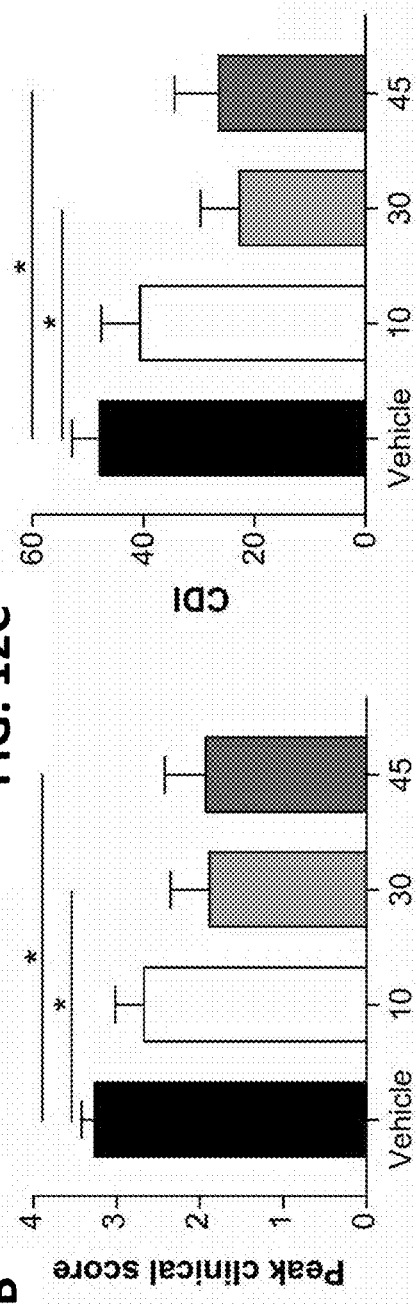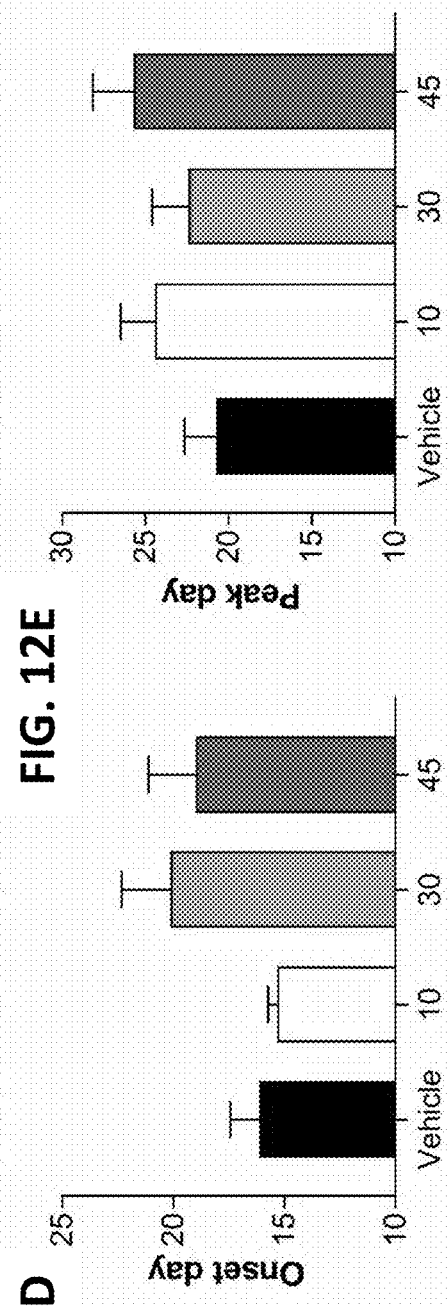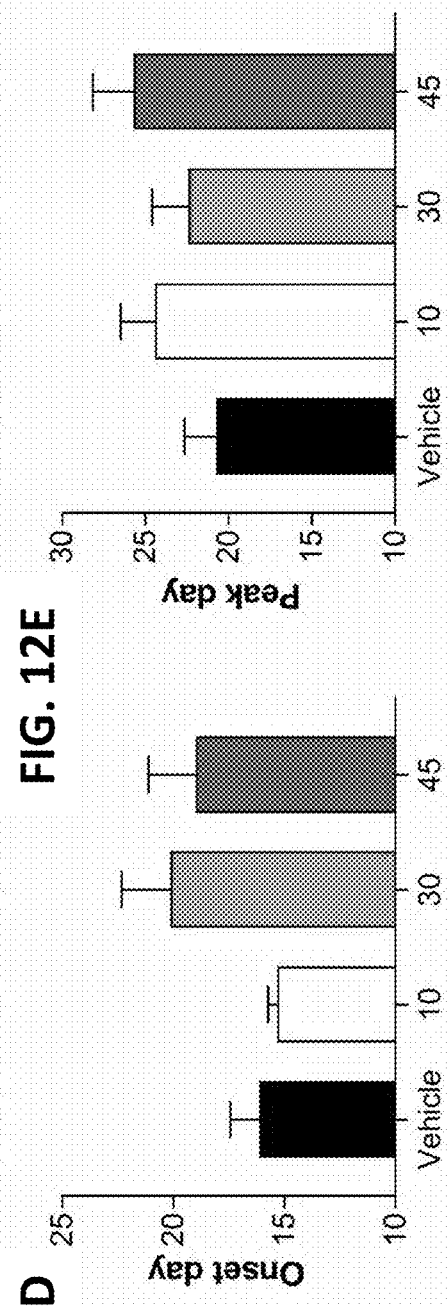
FIG. 12B FIG. 12C FIG. 12D FIG. 12E

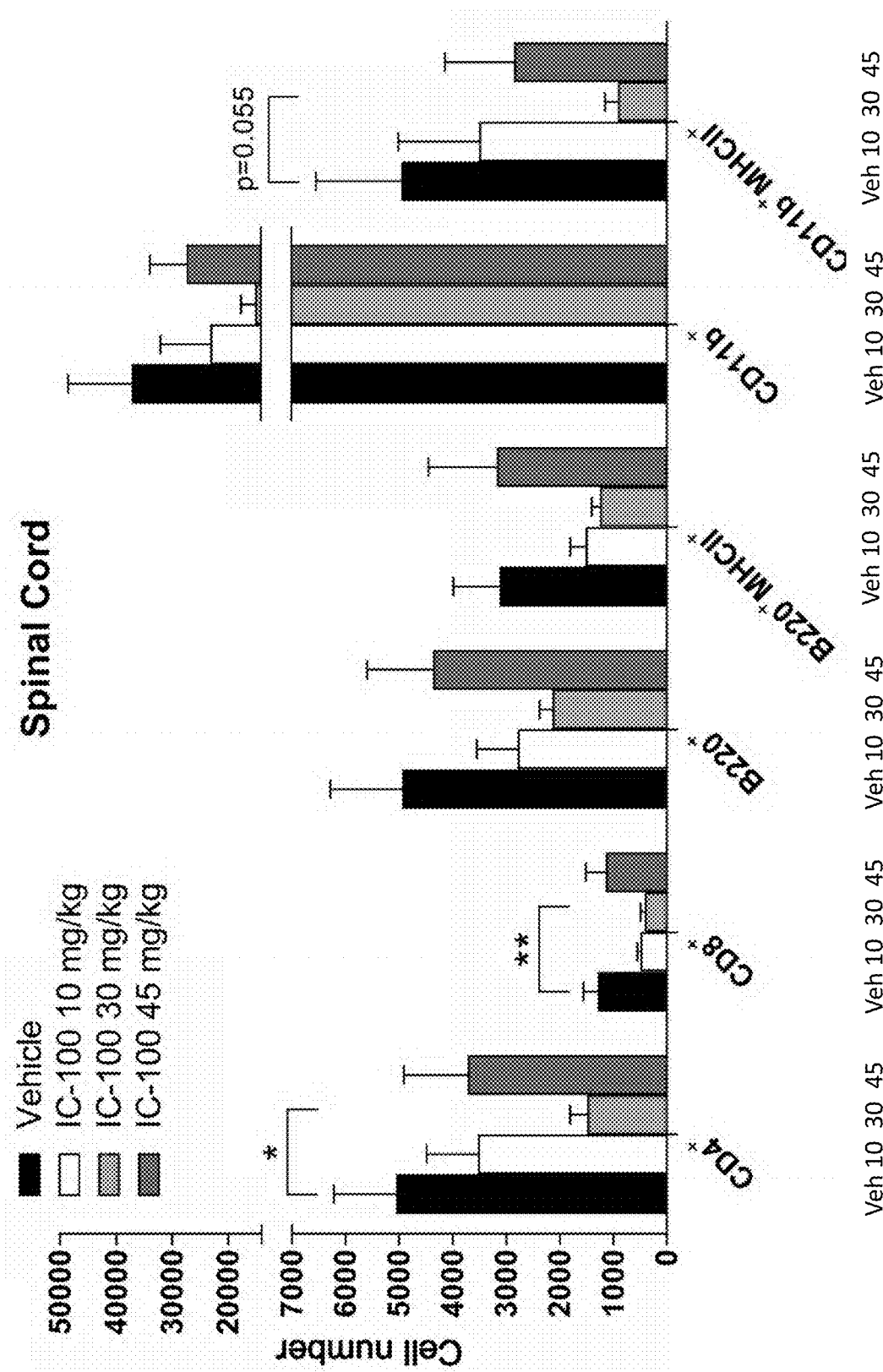

SEQUENCE LISTING

```
<160> NUMBER OF SEQ ID NOS: 35

<210> SEQ ID NO 1
<211> LENGTH: 16
<212> TYPE: PRT
<213> ORGANISM: Rattus norvegicus

<400> SEQUENCE: 1

Ala Leu Arg Gln Thr Gln Pro Tyr Leu Val Thr Asp Leu Glu Gln Ser
1               5                   10                  15

<210> SEQ ID NO 2
<211> LENGTH: 14
<212> TYPE: PRT
<213> ORGANISM: Homo sapiens

<400> SEQUENCE: 2

Arg Glu Ser Gln Ser Tyr Leu Val Glu Asp Leu Glu Arg Ser
1               5                   10

<210> SEQ ID NO 3
<211> LENGTH: 19
<212> TYPE: PRT
<213> ORGANISM: Homo sapiens

<400> SEQUENCE: 3

Cys Glu Tyr Tyr Thr Glu Ile Arg Glu Arg Glu Arg Glu Lys Ser Glu
1               5                   10                  15

Lys Gly Arg

<210> SEQ ID NO 4
<211> LENGTH: 15
<212> TYPE: PRT
<213> ORGANISM: Rattus norvegicus

<400> SEQUENCE: 4

Met Glu Glu Ser Gln Ser Lys Glu Glu Ser Asn Thr Glu Gly Cys
1               5                   10                  15

<210> SEQ ID NO 5
<211> LENGTH: 21
<212> TYPE: PRT
<213> ORGANISM: Artificial Sequence
<220> FEATURE:
<223> OTHER INFORMATION: antigenic fragment of caspase activating
      recruitment domain (ASC)

<400> SEQUENCE: 5
```

Lys Phe Lys Leu Lys Leu Leu Ser Val Pro Leu Arg Glu Gly Tyr
1               5                   10                  15

Gly Arg Ile Pro Arg
            20

<210> SEQ ID NO 6
<211> LENGTH: 7
<212> TYPE: PRT
<213> ORGANISM: Artificial Sequence
<220> FEATURE:
<223> OTHER INFORMATION: Heavy Chain CDR1 Amino Acid Sequence

<400> SEQUENCE: 6

Thr Ser Gly Met Gly Val Ser
1               5

<210> SEQ ID NO 7
<211> LENGTH: 16
<212> TYPE: PRT
<213> ORGANISM: Artificial Sequence
<220> FEATURE:
<223> OTHER INFORMATION: Heavy Chain CDR2 Amino Acid Sequence

<400> SEQUENCE: 7

His Ile Tyr Trp Asp Asp Asp Lys Arg Tyr Asn Pro Ser Leu Lys Ser
1               5                   10                  15

<210> SEQ ID NO 8
<211> LENGTH: 11
<212> TYPE: PRT
<213> ORGANISM: Artificial Sequence
<220> FEATURE:
<223> OTHER INFORMATION: Heavy Chain CDR3 Amino Acid Sequence

<400> SEQUENCE: 8

Ser Thr Pro Ile Val Ala Asn Ala Met Asp Tyr
1               5                   10

<210> SEQ ID NO 9
<211> LENGTH: 21
<212> TYPE: DNA
<213> ORGANISM: Artificial Sequence
<220> FEATURE:
<223> OTHER INFORMATION: Heavy Chain CDR1 Nucleic Acid Sequence

<400> SEQUENCE: 9
actagtggaa tgggtgtgag c                                         21

<210> SEQ ID NO 10
<211> LENGTH: 48
<212> TYPE: DNA
<213> ORGANISM: Artificial Sequence
<220> FEATURE:
<223> OTHER INFORMATION: Heavy Chain CDR2 Nucleic Acid Sequence

<400> SEQUENCE: 10
cacatttatt gggatgatga taagcgctac aacccatctc tgaagagc             48

<210> SEQ ID NO 11
<211> LENGTH: 33
<212> TYPE: DNA
<213> ORGANISM: Artificial Sequence
<220> FEATURE:
<223> OTHER INFORMATION: Heavy Chain CDR3 Nucleic Acid Sequence

<400> SEQUENCE: 11

```
agcaccccca tcgtggccaa cgccatggac tac                                    33
```

```
<210> SEQ ID NO 12
<211> LENGTH: 15
<212> TYPE: PRT
<213> ORGANISM: Artificial Sequence
<220> FEATURE:
<223> OTHER INFORMATION: Light (Kappa) Chain CDR1 Amino Acid Sequence

<400> SEQUENCE: 12

Lys Ala Ser Gln Ser Val Asp Tyr Asp Gly Asp Ser Tyr Met Asn
1               5                   10                  15
```

```
<210> SEQ ID NO 13
<211> LENGTH: 7
<212> TYPE: PRT
<213> ORGANISM: Artificial Sequence
<220> FEATURE:
<223> OTHER INFORMATION: Light (Kappa) Chain CDR2 Amino Acid Sequence

<400> SEQUENCE: 13

Ala Ala Ser Asn Leu Glu Ser
1               5
```

```
<210> SEQ ID NO 14
<211> LENGTH: 9
<212> TYPE: PRT
<213> ORGANISM: Artificial Sequence
<220> FEATURE:
<223> OTHER INFORMATION: Light (Kappa) Chain CDR3 Amino Acid Sequence

<400> SEQUENCE: 14

Gln Gln Ser Asn Glu Asp Pro Tyr Thr
1               5
```

```
<210> SEQ ID NO 15
<211> LENGTH: 45
<212> TYPE: DNA
<213> ORGANISM: Artificial Sequence
<220> FEATURE:
<223> OTHER INFORMATION: Light (Kappa) Chain CDR1 Nucleic Acid Sequence

<400> SEQUENCE: 15
aaggccagcc agagtgttga ctacgacggc gacagttaca tgaat                       45
```

```
<210> SEQ ID NO 16
<211> LENGTH: 21
<212> TYPE: DNA
<213> ORGANISM: Artificial Sequence
<220> FEATURE:
<223> OTHER INFORMATION: Light (Kappa) Chain CDR2 Nucleic Acid Sequence

<400> SEQUENCE: 16
gccgcatcta acctggaatc c                                                 21
```

```
<210> SEQ ID NO 17
<211> LENGTH: 27
<212> TYPE: DNA
<213> ORGANISM: Artificial Sequence
<220> FEATURE:
<223> OTHER INFORMATION: Light (Kappa) Chain CDR3 Nucleic Acid Sequence

<400> SEQUENCE: 17
cagcaatcta atgaggaccc ttacact                                           27
```

```
<210> SEQ ID NO 18
<211> LENGTH: 121
<212> TYPE: PRT
<213> ORGANISM: Artificial Sequence
<220> FEATURE:
<223> OTHER INFORMATION: VH1 Heavy Chain Sequence

<400> SEQUENCE: 18

Gln Val Thr Leu Lys Glu Ser Gly Pro Ala Ile Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ser Ser Lys Asn Gln Val
65                  70                  75                  80

Val Leu Lys Ile Thr Ser Val Asp Pro Val Asp Thr Ala Thr Tyr Ser
                85                  90                  95

Cys Ala Arg Ser Thr Pro Ile Val Ala Asn Ala Met Asp Tyr Trp Gly
            100                 105                 110

Gln Gly Thr Ser Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: VH2 Heavy Chain Sequence

<400> SEQUENCE: 19

Gln Val Thr Leu Lys Glu Ser Gly Pro Ala Leu Val Lys Pro Thr Gln
1               5                   10                  15

Thr Leu Thr Leu Thr Cys Ser Phe Ser Gly Phe Ser Leu Ser Thr Ser
            20                  25                  30

Gly Met Gly Val Ser Trp Ile Arg Gln Pro Ala Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ser Ser Lys Asn Gln Val
65                  70                  75                  80

Val Leu Thr Met Thr Asn Met Asp Pro Val Asp Thr Ala Thr Tyr Ser
                85                  90                  95

Cys Ala Arg Ser Thr Pro Ile Val Ala Asn Ala Met Asp Tyr Trp Gly
            100                 105                 110

Gln Gly Thr Leu Val Thr Val Ser Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: VH3 Heavy Chain Sequence

<400> SEQUENCE: 20

Gln Val Thr Leu Lys Glu Ser Gly Pro Ala Leu Val Lys Pro Thr Gln
1               5                   10                  15
```

```
Thr Leu Thr Leu Thr Cys Ser Phe Ser Gly Phe Ser Leu Ser Thr Ser
            20                  25                  30

Gly Met Gly Val Ser Trp Ile Arg Gln Pro Ala Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ser Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Thr Pro Ile Val Ala Asn Ala Met Asp Tyr Trp Gly
            100                 105                 110

Gln Gly Thr Leu Val Thr Val Ser Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: VH4 Heavy Chain Sequence

<400> SEQUENCE: 21

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Ala Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ser Thr Pro Ile Val Ala Asn Ala Met Asp Tyr Trp Gly
            100                 105                 110

Gln Gly Thr Leu Val Thr Val Ser Ser
        115                 120

<210> SEQ ID NO 22
<211> LENGTH: 121
<212> TYPE: PRT
<213> ORGANISM: Artificial Sequence
<220> FEATURE:
<223> OTHER INFORMATION: VH0 (Chimeric) Heavy Chain

<400> SEQUENCE: 22

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ser Ser Ser Asn Gln Val
```

```
                65                  70                  75                  80
            Phe Leu Lys Ile Thr Ser Val Asp Thr Ala Asp Thr Ala Thr Tyr Ser
                                85                  90                  95
            Cys Ala Arg Ser Thr Pro Ile Val Ala Asn Ala Met Asp Tyr Trp Gly
                        100                 105                 110
            Gln Gly Thr Ser Val Thr Val Ser Ser
                        115                 120

<210> SEQ ID NO 23
<211> LENGTH: 363
<212> TYPE: DNA
<213> ORGANISM: Artificial Sequence
<220> FEATURE:
<223> OTHER INFORMATION: VH1 Heavy Chain Sequence

<400> SEQUENCE: 23
caggtcacct tgaaggagtc tggtcctgcc atcgtgaaac ccacacagac cctcacgctg      60
acctgcagct tctctgggtt ctcactcagc actagtggaa tgggtgtgag ctggatccgt     120
cagccctcag aaagggcct  ggagtggctt gcacacattt attgggatga tgataagcgc     180
tacaacccat ctctgaagag caggctcacc atctccaagg acagctccaa aaaccaggtg     240
gtccttaaaa tcaccagcgt ggaccctgtg acacagcca  catattcctg tgcacggagc     300
acccccatcg tggccaacgc catggactac tggggccaag gaaccagcgt caccgtctcc     360
tca                                                                  363

<210> SEQ ID NO 24
<211> LENGTH: 363
<212> TYPE: DNA
<213> ORGANISM: Artificial Sequence
<220> FEATURE:
<223> OTHER INFORMATION: VH2 Heavy Chain Sequence

<400> SEQUENCE: 24
caggtcacct tgaaggagtc tggtcctgcc ctggtgaaac ccacacagac cctcacgctg      60
acctgcagct tctctgggtt ctcactcagc actagtggaa tgggtgtgag ctggatccgt     120
cagcccgccg aaagggcct  ggagtggctt gcacacattt attgggatga tgataagcgc     180
tacaacccat ctctgaagag caggctcacc atctccaagg acagctccaa aaaccaggtg     240
gtccttacaa tgaccaacat ggaccctgtg acacagcca  catattcctg tgcacggagc     300
acccccatcg tggccaacgc catggactac tggggccaag gaaccctggt caccgtctcc     360
tca                                                                  363

<210> SEQ ID NO 25
<211> LENGTH: 363
<212> TYPE: DNA
<213> ORGANISM: Artificial Sequence
<220> FEATURE:
<223> OTHER INFORMATION: VH3 Heavy Chain Sequence

<400> SEQUENCE: 25
caggtcacct tgaaggagtc tggtcctgcc ctggtgaaac ccacacagac cctcacgctg      60
acctgcagct tctctgggtt ctcactcagc actagtggaa tgggtgtgag ctggatccgt     120
cagcccgccg aaagggcct  ggagtggctt gcacacattt attgggatga tgataagcgc     180
tacaacccat ctctgaagag caggctcacc atctccaagg acagctccaa aaaccaggtg     240
gtccttacaa tgaccaacat ggaccctgtg acacagcca  catattactg tgcacggagc     300
```

```
accccccatcg tggccaacgc catggactac tggggccaag gaaccctggt caccgtctcc    360
tca                                                                    363

<210> SEQ ID NO 26
<211> LENGTH: 363
<212> TYPE: DNA
<213> ORGANISM: Artificial Sequence
<220> FEATURE:
<223> OTHER INFORMATION: VH4 Heavy Chain Sequence

<400> SEQUENCE: 26
caggtcacct tgaaggagtc tggtcctgcc ctggtgaaac ccacacagac cctcacgctg     60
acctgcacct tctctgggtt ctcactcagc actagtggaa tgggtgtgag ctggatccgt    120
cagcccgccg aaagggcct ggagtggctt gcacacattt attgggatga tgataagcgc    180
tacaacccat ctctgaagag caggctcacc atctccaagg acacctccaa aaaccaggtg    240
gtccttacaa tgaccaacat ggaccctgtg acacagcca catattactg tgcacggagc    300 accccccatcg tggccaacgc catggactac tggggccaag gaaccctggt caccgtctcc    360
tca                                                                    363

<210> SEQ ID NO 27
<211> LENGTH: 363
<212> TYPE: DNA
<213> ORGANISM: Artificial Sequence
<220> FEATURE:
<223> OTHER INFORMATION: VH0 (Chimeric) Heavy Chain

<400> SEQUENCE: 27
caggttactc tgaaagagtc tggccctggg atattgcagc cctcccagac cctcagtctg     60
acttgttctt tctctgggtt ttcactgagc acttctggta tgggtgtgag ctggattcgt    120
cagccttcag gaaagggtct ggagtggctg gcacacattt actgggatga tgacaagcgc    180
tataacccat ccctgaagag ccggctcaca atctccaagg attcctccag caaccaggtc    240
ttcctcaaga tcaccagtgt ggacactgca gatactgcca catactcctg tgctcgaagt    300
actccgattg tagctaatgc tatggactac tggggtcaag gaacctcagt caccgtctcc    360
tca                                                                    363

<210> SEQ ID NO 28
<211> LENGTH: 111
<212> TYPE: PRT
<213> ORGANISM: Artificial Sequence
<220> FEATURE:
<223> OTHER INFORMATION: VL1 Light Chain Sequence

<400> SEQUENCE: 28

Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Glu Glu Asp Val Ala Thr Tyr Tyr Cys Gln Gln Ser Asn
                85                  90                  95
```

```
Glu Asp Pro Tyr Thr Phe Gly Gln Gly Thr Lys Leu Glu Ile Lys
            100                 105                 110
```

<210> SEQ ID NO 29
<211> LENGTH: 111
<212> TYPE: PRT
<213> ORGANISM: Artificial Sequence
<220> FEATURE:
<223> OTHER INFORMATION: VL2 Light Chain Sequence

<400> SEQUENCE: 29

```
Asp Ile Val Leu Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110
```

<210> SEQ ID NO 30
<211> LENGTH: 111
<212> TYPE: PRT
<213> ORGANISM: Artificial Sequence
<220> FEATURE:
<223> OTHER INFORMATION: VL3 Light Chain Sequence

<400> SEQUENCE: 30

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Gln Pro Glu Asp Val Ala Thr Tyr Tyr Cys Gln Gln Ser Asn
                85                  90                  95

Glu Asp Pro Tyr Thr Phe Gly Gln Gly Thr Lys Leu Glu Ile Lys
            100                 105                 110
```

<210> SEQ ID NO 31
<211> LENGTH: 111
<212> TYPE: PRT
<213> ORGANISM: Artificial Sequence
<220> FEATURE:
<223> OTHER INFORMATION: VL0 Chimeric Light Chain Sequence

<400> SEQUENCE: 31

```
Asp Ile Val Leu Thr Gln Ser Pro Ala Ser Leu Ala Val Ser Leu Gly
1               5                   10                  15
```

```
Gln Arg Ala Thr Ile Ser Cys Lys Ala Ser Gln Ser Val Asp Tyr Asp
                20                  25                  30

Gly Asp Ser Tyr Met Asn Trp Tyr Gln Gln Lys Pro Gly Gln Pro Pro
            35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

<210> SEQ ID NO 32
<211> LENGTH: 333
<212> TYPE: DNA
<213> ORGANISM: Artificial Sequence
<220> FEATURE:
<223> OTHER INFORMATION: VL1 Light Chain Sequence

<400> SEQUENCE: 32

```
gacatcgtgc tgacccagtc tccagactcc ctggctgtgt ctctgggcga gagggccacc    60
atcaactgca aggccagcca gagtgttgac tacgacggcg acagttacat gaattggtac   120
cagcagaaac caggacagcc tcctaagctg ctcatttacg ccgcatctaa cctggaatcc   180
ggcatccctg cccgattcag tggcagcggg tctgggacag atttcactct caccatcagc   240
agcctgcagg aggaagatgt ggcaacttat tactgtcagc aatctaatga ggacccttac   300
acttttggcc aggggaccaa gctggagatc aaa                                 333
```

<210> SEQ ID NO 33
<211> LENGTH: 333
<212> TYPE: DNA
<213> ORGANISM: Artificial Sequence
<220> FEATURE:
<223> OTHER INFORMATION: VL2 Light Chain Sequence

<400> SEQUENCE: 33

```
gacatcgtgc tgacccagtc tccagactcc ctggctgtgt ctctgggcga gagggccacc    60
atcaactgca aggccagcca gagtgttgac tacgacggcg acagttacat gaattggtac   120
cagcagaaac caggacagcc tcctaagctg ctcatttacg ccgcatctaa cctggaatcc   180
ggcatccctg cccgattcag tggcagcggg tctgggacag atttcactct caccatcagc   240
agcctgcagc ctgaagatgt ggcaacttat tactgtcagc aatctaatga ggacccttac   300
acttttggcc aggggaccaa gctggagatc aaa                                 333
```

<210> SEQ ID NO 34
<211> LENGTH: 333
<212> TYPE: DNA
<213> ORGANISM: Artificial Sequence
<220> FEATURE:
<223> OTHER INFORMATION: VL3 Light Chain Sequence

<400> SEQUENCE: 34

```
gacatcgtga tgacccagtc tccagactcc ctggctgtgt ctctgggcga gagggccacc    60
atcaactgca aggccagcca gagtgttgac tacgacggcg acagttacat gaattggtac   120
cagcagaaac caggacagcc tcctaagctg ctcatttacg ccgcatctaa cctggaatcc   180
ggcatccctg cccgattcag tggcagcggg tctgggacag atttcactct caccatcagc   240
```

```
agcctgcagc ctgaagatgt ggcaacttat tactgtcagc aatctaatga ggacccttac    300
acttttggcc aggggaccaa gctggagatc aaa                                 333

<210> SEQ ID NO 35
<211> LENGTH: 333
<212> TYPE: DNA
<213> ORGANISM: Artificial Sequence
<220> FEATURE:
<223> OTHER INFORMATION: VLO Chimeric Light Chain Sequence

<400> SEQUENCE: 35
gacattgtgc tgacccaatc tccagcttct ttggctgtgt ctctagggca gagggccacc     60
atctcctgca aggccagcca aagtgttgat tatgatggtg atagttatat gaactggtac    120
caacagaaac caggacagcc acccaaactc ctcatctatg ctgcatccaa tctagaatct    180
ggcatcccag ccaggtttag tggcagtggg tctgggacag acttcaccct caacatccat    240
cctgtggagg aggaggatgc tgcaacctat tactgtcagc aaagtaatga ggacccgtac    300
acgttcggag gggggaccaa gctggaaata aaa                                 333
```

US 11,840,565 B2

METHODS AND COMPOSITIONS FOR TREATING VIRUS-ASSOCIATED INFLAMMATION

CROSS REFERENCE TO RELATED APPLICATIONS

This application claims priority to and is a continuation of U.S. application Ser. No. 16/856,407, filed Apr. 23, 2020, which is a continuation-in-part of U.S. application Ser. No. 16/026,482, filed Jul. 3, 2018 (issued as U.S. Pat. No. 10,703,811), which is a continuation-in-part of International Application No. PCT/US17/68713, filed Dec. 28, 2017, which claims priority from U.S. Provisional Application Ser. No. 62/440,180, filed Dec. 29, 2016, which is herein incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: UNMI_010_07US_SeqList_ST25.txt, date recorded: Nov. 11, 2021, file size 19,983 bytes).

FIELD

The invention relates generally to the fields of virology, immunology and medicine. More particularly, the invention relates to compositions and methods for modulating ASC (Apoptosis-associated Speck-like protein containing a Caspase Activating Recruitment Domain (CARD)) activity and Absent in Melanoma 2 (AIM2) inflammasome activity in the Central Nervous System (CNS) and/or lungs of a mammal as treatments for reducing inflammation in response to viral infections, injuries or conditions that produce inflammation in the CNS and/or lungs. The invention also relates to monoclonal antibodies or fragments thereof that specifically bind ASC.

BACKGROUND

Severe acute respiratory syndrome coronavirus (SARS-CoV) is an enveloped virus with a single stranded positive-sense RNA genome (30 kb) that causes dangerous and potentially fatal conditions such as acute respiratory distress syndrome (ARDS) and acute lung injury (ALI). ARDS/ALI is a major public health problem, and in spite of significant advances in understanding of the pathophysiology of the disease, mortality and morbidity remain high. The fatality rate of SARS-CoV from November 2002 to July 2003 was 9.6% according to the World Health Organization. The fatality rate for CoV-2 is yet to be accurately determined, but it is anticipated that coronaviruses will occur cyclically, like the flu. Thus, there is a need to identify new therapies and vaccines to solve current and future healthcare needs in the patient population.

Systemic inflammatory factors may lead to pulmonary dysfunction and lung injury. A flood of secreted inflammatory mediators, including cytokines, chemokines, and danger-associated molecular patterns (DAMPs) are released by injured cells and contribute to inflammation in the lungs. Moreover, interleukin (IL)-1β is significantly elevated in bronchoalveolar lavage (BAL) fluid from patients with ALI, and cytokine-activated neutrophils, including IL-1β, adhere to the pulmonary endothelial surface of capillaries and migrate into the interstitial and alveolar spaces. These findings suggest a role of the inflammasome in ALI. In addition, the NLRP3 inflammasome has been implicated in sensing cell damage induced by viroporins upon RNA viral infection (Nieto-Torres, Verdia-Baguena et al. 2015). A recent study that systematically mapped the interaction landscape between SARS-CoV-2 proteins and human proteins revealed that SARS-CoV-2 interacts with multiple innate immune pathways, including members of the inflammasome pathway (Gordon et al., 2020). The inflammasome is a multiprotein complex involved in the activation of the pro-inflammatory cytokines IL-1β60 and IL-18. This multiprotein complex is comprised of a receptor protein such as NOD-like receptor (NLR) or absent in melanoma (AIM) proteins, an adaptor protein known as apoptosis-associated speck-like protein containing a caspase-recruitment domain (ASC) and caspase-1. Inflammasomes are named after their receptor proteins such as NLRP1, NLRP3 or AIM2.

In severe COVID-19 cases, patients may experience a hyperinflammatory response that is referred to as cytokine storm syndrome. Cytokine storm syndrome is a secondary haemophagocytic lymphohistocytosis (sHLH) characterized by fulminant hypercytokemia that results in multiorgan failure (Mehta, McAuley et al. 2020). A study looking at 150 confirmed cases of COVID-19 in Wuhan China revealed that patients presented elevated levels of Ferritin and IL-6, both signs of hyperinflammation (Ruan, Yang et al. 2020). Accordingly, there is an urgent need not only for elucidating the pathomechanisms of lung inflammation caused by SARS-CoV-2 as well as other viruses, but also the development of therapeutic compositions and uses thereof for treating and/or preventing lung inflammation.

SUMMARY

In one aspect, provided herein is a monoclonal antibody or an antibody fragment thereof that binds to Apoptosis-associated Speck-like protein containing a Caspase Activating Recruitment Domain (ASC), wherein the antibody or the antibody fragment binds specifically to an epitope of ASC, wherein the epitope comprises or consists of the amino acid sequence of SEQ ID NO: 5 or 5-10, 10-15 or 15-20 amino acids of SEQ ID NO: 5.

In another aspect, provided herein is a monoclonal antibody or an antibody fragment thereof that binds specifically to ASC, wherein the antibody or the antibody fragment comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3. In some cases, the VH region amino acid sequence comprises SEQ ID NO: 18, 19, 20, 21, 22, or an amino acid sequence that is at least 95%, 96%, 97%, 98% or 99% identical to the amino acid sequence of SEQ ID NO: 18, 19, 20, 21, or 22. In some cases, the ASC is human ASC protein. In some cases, the antibody fragment is an Fab, an F(ab')$_2$, an Fab', an scFv, a single domain antibody, a diabody or a single chain camelid antibody or a shark antibody. In some cases, the monoclonal antibody or the antibody fragment thereof is human, humanized or chimeric. In some cases, provided herein is an isolated nucleic acid molecule encoding the monoclonal antibody or the antibody fragment thereof. In some cases, provided herein is an expression vector comprising the nucleic acid molecule. In some cases, provided herein is the nucleic acid molecule is operatively linked to regulatory sequences suitable for expression of the nucleic acid segment in a host cell. In some cases, provided herein is a recombinant host cell comprising the expression vector. In another aspect, provided herein is a method for producing an antibody or an antibody fragment that binds specifically to ASC, the method comprising: culturing a recombinant host cell comprising the expression vector under conditions whereby the nucleic acid molecule is expressed, thereby producing the monoclonal antibody or the antibody fragment thereof that binds specifically to ASC. In some cases, provided herein is a pharmaceutical composition comprising the monoclonal antibody or the antibody fragment thereof, and a pharmaceutically acceptable carrier, diluent or excipient. In some cases, provided herein is a method of treating inflammation in a subject, the method comprises administering to the subject a therapeutically effective amount of the monoclonal antibody or the antibody fragment thereof, thereby treating the inflammation in the subject. In some cases, the administering the monoclonal antibody or the antibody fragment thereof reduces levels of at least inflammatory cytokine. In some cases, the inflammation is an inflammasome-related inflammation. In some cases, the inflammasome-related inflammation is associated with a viral infection, a central nervous system (CNS) injury, an autoimmune or neurodegenerative disease. In some cases, the viral infection is caused by coronaviruses, such as SARS-CoV-2, MERS (Middle East Respiratory Virus) coronavirus, as well as an influenza virus, such as influenza A H5N1 (avian influenza) and influenza A H1N1 (swine flu). In some cases, the CNS injury selected from the group consisting of traumatic brain injury (TBI), stroke and spinal cord injury (SCI). In some cases, the autoimmune or neurodegenerative disease is amyotrophic lateral sclerosis (ALS), Alzheimer's disease, Parkinson's disease, muscular dystrophy (MD) or multiple sclerosis (MS).

In some cases, the administration of the monoclonal antibody or the antibody fragment thereof results in inhibition of inflammasome activation in the subject. In some cases, the administration of the monoclonal antibody or the antibody fragment thereof results in a reduction in the activity of ASC as compared to a control. In some cases, the control is an untreated subject. In some cases, the administration is intracerebroventricularly, intraperitoneally, intravenously, intranasally or by inhalation. In some cases, provided herein is a method of treating virus-associated lung inflammation in a subject, including acute respiratory distress syndrome (ARDS), the method comprising administering to the subject a therapeutically effective amount of the monoclonal antibody or the antibody fragment thereof, thereby treating lung inflammation in the subject. In some cases, the administering the monoclonal antibody or the antibody fragment thereof reduces levels of at least inflammatory cytokine. In some cases, the administration of the monoclonal antibody or the antibody fragment thereof results in inhibition of inflammasome activation in the subject. In some cases, the administration of the monoclonal antibody or the antibody fragment thereof results in a reduction in the activity of ASC as compared to a control. In some cases, the control is an untreated subject. In some cases, the administration is intracerebroventricularly, intraperitoneally, intravenously, intranasally or by inhalation.

In yet another aspect, provided herein is a monoclonal antibody or an antibody fragment thereof that binds specifically to ASC, wherein the antibody or the antibody fragment comprises a light chain variable (VL) region and a heavy chain variable (VH) region, wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3. In some cases, the VL region amino acid sequence comprises SEQ ID NO: 28, 29, 30, 31, or an amino acid sequence that is at least 95%, 96%, 97%, 98% or 99% identical to the amino acid sequence of SEQ ID NO: 28, 29, 30 or 31. In some cases, the ASC is human ASC protein. In some cases, the antibody fragment is an Fab, an F(ab')$_2$, an Fab', an scFv, a single domain antibody, a diabody or a single chain camelid antibody. In some cases, the monoclonal antibody or the antibody fragment thereof is human, humanized or chimeric. In some cases, provided herein is an isolated nucleic acid molecule encoding the monoclonal antibody or the antibody fragment thereof. In some cases, provided herein is an expression vector comprising the nucleic acid molecule. In some cases, provided herein is the nucleic acid molecule is operatively linked to regulatory sequences suitable for expression of the nucleic acid segment in a host cell. In some cases, provided herein is a recombinant host cell comprising the expression vector. In another aspect, provided herein is a method for producing an antibody or an antibody fragment that binds specifically to ASC, the method comprising: culturing a recombinant host cell comprising the expression vector under conditions whereby the nucleic acid molecule is expressed, thereby producing the monoclonal antibody or the antibody fragment thereof that binds specifically to ASC. In some cases, provided herein is a pharmaceutical composition comprising the monoclonal antibody or the antibody fragment thereof, and a pharmaceutically acceptable carrier, diluent or excipient. In some cases, provided herein is a method of treating inflammation in a subject, the method comprises administering to the subject a therapeutically effective amount of the monoclonal antibody or the antibody fragment thereof, thereby treating the inflammation in the subject. In some cases, the administering the monoclonal antibody or the antibody fragment thereof reduces levels of at least inflammatory cytokine. In some cases, the inflammation is an inflammasome-related inflammation. In some cases, the inflammasome-related inflammation is associated with a central nervous system (CNS) injury, an autoimmune or neurodegenerative disease. In some cases, the CNS injury selected from the group consisting of traumatic brain injury (TBI), stroke and spinal cord injury (SCI). In some cases, the autoimmune or neurodegenerative disease is amyotrophic lateral sclerosis (ALS), Alzheimer's disease, Parkinson's disease, muscular dystrophy (MD) or multiple sclerosis (MS). In some cases, the administration of the monoclonal antibody or the antibody fragment thereof results in inhibition of inflammasome activation in the subject. In some cases, the administration of the monoclonal antibody or the antibody fragment thereof results in a reduction in the activity of ASC as compared to a control. In some cases, the control is an untreated subject. In some cases, the administration is intracerebroventricularly, intraperitoneally, intravenously, intranasally or by inhalation. In some cases, provided herein is a method of treating virus-associated lung inflammation in a subject, including ARDS, the method comprising administering to the subject a therapeutically effective amount of the monoclonal antibody or the antibody fragment thereof, thereby treating MS in the subject. In some cases, the administering the monoclonal antibody or the antibody fragment thereof reduces levels of at least inflammatory cytokine. In some cases, the administration of the monoclonal antibody or the antibody fragment thereof results in inhibition of inflammasome activation in the subject. In some cases, the administration of the monoclonal antibody or the antibody fragment thereof results in a reduction in the activity of ASC as compared to a control. In some cases, the control is an untreated subject. In some cases, the administration is intracerebroventricularly, intraperitoneally, intravenously, intranasally or by inhalation.

In still another aspect, provided herein is a monoclonal antibody or an antibody fragment thereof that binds specifically to ASC, wherein the antibody or the antibody fragment comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3; and wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3. In some cases, the VH region amino acid sequence comprises SEQ ID NO: 18, 19, 20, 21, 22, or an amino acid sequence that is at least 95%, 96%, 97%, 98% or 99% identical to the amino acid sequence of SEQ ID NO: 18, 19, 20, 21 or 22; and wherein the VL region amino acid sequence comprises SEQ ID NO: 28, 29, 30, 31, or an amino acid sequence that is at least 95%, 96%, 97%, 98% or 99% identical to the amino acid sequence of SEQ ID NO: 28, 29, 30 or 31. In some cases, the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 28 or an amino acid sequence that is at least 95%, 96%, 97%, 98% or 99% identical to the amino acid sequence of SEQ ID NO: 28. In some cases, the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 29 or an amino acid sequence that is at least 95%, 96%, 97%, 98% or 99% identical to the amino acid sequence of SEQ ID NO: 29. In some cases, the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 30 or an amino acid sequence that is at least 95%, 96%, 97%, 98% or 99% identical to the amino acid sequence of SEQ ID NO: 30. In some cases, the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 31 or an amino acid sequence that is at least 95%, 96%, 97%, 98% or 99% identical to the amino acid sequence of SEQ ID NO: 31. In some cases, the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 28 or an amino acid sequence that is at least 95%, 96%, 97%, 98% or 99% identical to the amino acid sequence of SEQ ID NO: 28. In some cases, the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 29 or an amino acid sequence that is at least 95%, 96%, 97%, 98% or 99% identical to the amino acid sequence of SEQ ID NO: 29. In some cases, the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 30 or an amino acid sequence that is at least 95%, 96%, 97%, 98% or 99% identical to the amino acid sequence of SEQ ID NO: 30. In some cases, the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 31 or an amino acid sequence that is at least 95%, 96%, 97%, 98% or 99% identical to the amino acid sequence of SEQ ID NO: 31. In some cases, the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 28 or an amino acid sequence that is at least 95%, 96%, 97%, 98% or 99% identical to the amino acid sequence of SEQ ID NO: 28. In some cases, the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 29 or an amino acid sequence that is at least 95%, 96%, 97%, 98% or 99% identical to the amino acid sequence of SEQ ID NO: 29. In some cases, the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 30 or an amino acid sequence that is at least 95%, 96%, 97%, 98% or 99% identical to the amino acid sequence of SEQ ID NO: 30. In some cases, the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 31 or an amino acid sequence that is at least 95%, 96%, 97%, 98% or 99% identical to the amino acid sequence of SEQ ID NO: 31. In some cases, the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 28 or an amino acid sequence that is at least 95%, 96%, 97%, 98% or 99% identical to the amino acid sequence of SEQ ID NO: 28. In some cases, the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 29 or an amino acid sequence that is at least 95%, 96%, 97%, 98% or 99% identical to the amino acid sequence of SEQ ID NO: 29. In some cases, the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 30 or an amino acid sequence that is at least 95%, 96%, 97%, 98% or 99% identical to the amino acid sequence of SEQ ID NO: 30. In some cases, the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 31 or an amino acid sequence that is at least 95%, 96%, 97%, 98% or 99% identical to the amino acid sequence of SEQ ID NO: 31. In some cases, the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 28 or an amino acid sequence that is at least 95%, 96%, 97%, 98% or 99% identical to the amino acid sequence of SEQ ID NO: 28. In some cases, the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 29 or an amino acid sequence that is at least 95%, 96%, 97%, 98% or 99% identical to the amino acid sequence of SEQ ID NO: 29. In some cases, the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 30 or an amino acid sequence that is at least 95%, 96%, 97%, 98% or 99% identical to the amino acid sequence of SEQ ID NO: 30. In some cases, the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 31 or an amino acid sequence that is at least 95%, 96%, 97%, 98% or 99% identical to the amino acid sequence of SEQ ID NO: 31. In some cases, the ASC is human ASC protein. In some cases, the antibody fragment is an Fab, an F(ab')$_2$, an Fab', an scFv, a single domain antibody, a diabody or a single chain camelid antibody. In some cases, the monoclonal antibody or the antibody fragment thereof is human, humanized or chimeric. In some cases, provided herein is an isolated nucleic acid molecule encoding the monoclonal antibody or the antibody fragment thereof. In some cases, provided herein is an expression vector comprising the nucleic acid molecule. In some cases, provided herein is the nucleic acid molecule is operatively linked to regulatory sequences suitable for expression of the nucleic acid segment in a host cell. In some cases, provided herein is a recombinant host cell comprising the expression vector. In another aspect, provided herein is a method for producing an antibody or an antibody fragment that binds specifically to ASC, the method comprising: culturing a recombinant host cell comprising the expression vector under conditions whereby the nucleic acid molecule is expressed, thereby producing the monoclonal antibody or the antibody fragment thereof that binds specifically to ASC. In some cases, provided herein is a pharmaceutical composition comprising the monoclonal antibody or the antibody fragment thereof, and a pharmaceutically acceptable carrier, diluent or excipient. In some cases, provided herein is a method of treating inflammation in a subject, the method comprises administering to the subject a therapeutically effective amount of the monoclonal antibody or the antibody fragment thereof, thereby treating the inflammation in the subject. In some cases, the administering the monoclonal antibody or the antibody fragment thereof reduces levels of at least inflammatory cytokine. In some cases, the inflammation is an inflammasome-related inflammation. In some cases, the inflammasome-related inflammation is associated with a viral infection, a central nervous system (CNS) injury, an autoimmune or neurodegenerative disease. In some cases, the viral infection is caused by a coronavirus, such as SARS-CoV-2, or an influenza virus, such as influenza A H5N1 (avian influenza) and influenza A H1N1 (swine flu). In some cases, the CNS injury selected from the group consisting of traumatic brain injury (TBI), stroke and spinal cord injury (SCI). In some cases, the autoimmune or neurodegenerative disease is amyotrophic lateral sclerosis (ALS), Alzheimer's disease, Parkinson's disease, muscular dystrophy (MD) or multiple sclerosis (MS). In some cases, the administration of the monoclonal antibody or the antibody fragment thereof results in inhibition of inflammasome activation in the subject. In some cases, the administration of the monoclonal antibody or the antibody fragment thereof results in a reduction in the activity of ASC as compared to a control. In some cases, the control is an untreated subject. In some cases, the administration is intracerebroventricularly, intraperitoneally, intravenously, intranasally or by inhalation. In some cases, provided herein is a method of treating multiple sclerosis (MS) in a subject, the method comprises administering to the subject a therapeutically effective amount of the monoclonal antibody or the antibody fragment thereof, thereby treating MS in the subject. In some cases, the administering the monoclonal antibody or the antibody fragment thereof reduces levels of at least inflammatory cytokine. In some cases, the administration of the monoclonal antibody or the antibody fragment thereof results in inhibition of inflammasome activation in the subject. In some cases, the administration of the monoclonal antibody or the antibody fragment thereof results in a reduction in the activity of ASC as compared to a control. In some cases, the control is an untreated subject. In some cases, the administration is intracerebroventricularly, intraperitoneally, intravenously, intranasally or by inhalation.

BRIEF DESCRIPTION OF THE DRAWINGS

FIG. 1A shows a representative immunoblot of active caspase-1, ASC, IL-18, IL-β, HMGB1, and AIM2 after TBI. Active caspase-1 (FIG. 1B), ASC (FIG. 1C), IL-18 (FIG. 1D), HMGB1 (FIG. 1E), AIM 2 (FIG. 1F), and IL-β, (FIG. 1G), are significantly elevated in cortical tissue at 4 and 24 h post-TBI. Data presented as mean+/−SEM; **$p<0.001$, *$p<0.01$, **$p<0.01$, *$p<0.05$ compared to sham. N=4-5 per group.

FIG. 2A shows AIM2, FIG. 2B shows active Caspase-1 and FIG. 2C shows ASC immunoreactivity increases in lung tissue after CCI (4, 24 h) when compared to mice. Confocal images of AIM2, caspase-1, and ASC (green) and type II epithelial cells (surfactant protein C, red).

FIG. 3A shows representative immunoblot of nuclear HMGB1 after TBI. FIG. 3B shows nuclear HMGB1 is significantly elevated in 4 hour injured animals compared to sham. FIG. 3C shows representative immunoblot of cytoplasmic HMGB1 after TBI. FIG. 3D shows cytoplasmic HMGB1 is significantly elevated in 4 hour injured animals compared to sham. Data presented as mean+/−SEM; *p<0.05 compared to sham. N=4-5 per group. FIG. 3E shows HMGB1 immunoreactivity increased in lung tissue after CCI when compared to sham mice. Confocal images of HMGB1 and type II epithelial cells (surfactant protein C, red)

FIG. 4A-4C illustrates Pyroptosome formation in mice lungs 4 hours post-TBI. FIG. 4A shows TBI induces laddering of ASC in lung tissue, indicating formation of the pyroptosome, an oligomerization of ASC dimers that leads to activation of caspase-1 and pyroptosis. FIG. 4B shows representative immunoblot and FIG. 4C shows quantification of gasdermin. Gasdermin-D is significantly elevated in lung tissue post-TBI. Data presented as mean+/−SEM. N=4-5 per group, **p<0.01 compared to sham.

FIG. 5A shows H&E staining of lung sections from sham and injured animals at 4 h and 24 h. Sections show evidence of neutrophil infiltration (arrow heads), changes in morphology of alveolar capillary membranes (asterisk, *), interstitial edema (short arrows), and evidence of thickening of the interstitium and the alveolar septum (pound, #). FIG. 5B shows acute lung injury scoring is significantly increased in injured animals when compared to sham at 4 h and 24 h. Data presented as mean+/−SEM. N=4-5 per group, *p<0.05 compared to sham.

FIG. 6 illustrates expression of CD81 in serum-derived EV from control and TBI-injured mice. Representative immunoblot of CD81 in serum-derived EV from sham control and TBI-injured mice.

FIG. 7A illustrates a representative immunoblot showing that caspase-1 (FIG. 7B), ASC (FIG. 7C), IL-18 (FIG. 7D), AIM2 (FIG. 7E), HMGB1 (FIG. 7F) are elevated in the lungs of animals that received EV isolated from TBI mice when compared to EV from sham animals. Data presented as mean+/−SEM; *p<0.0.05 compared to sham. N=3 per group. EV from TBI mice induced alveolar morphological changes (decreased alveolar size) and infiltration of inflammatory cells as determined by H&E staining (FIG. 7G). ALI score is significantly increased in EV delivered from injured mice compared to uninjured mice (FIG. 7G). Data presented as mean+/−SEM; **p<0.01, *p<0.0.05 compared to uninjured group.

FIG. 8A-8F illustrates treatment with Enoxaparin (3 mg/kg) and IC 100 (5 mg/kg) reduces inflammasome expression in lungs of animals delivered EV from injured mice. FIG. 8A illustrates a representative immunoblot showing that caspase-1 (FIG. 8B), ASC (FIG. 8C), IL-1β (FIG. 8D), AIM2 (FIG. 8E), HMGB1 (FIG. 8F) are reduced in the lungs of animals that were treated with Enoxaparin and IC 100 when compared to untreated positive control animals. Data presented as mean+/−SEM; **p<0.001, *p<0.01, **p<0.01, *p<0.05 compared to sham. N=4 per group.

FIG. 9A-9E illustrates treatment with Enoxaparin (3 mg/kg) and IC 100 (5 mg/kg) reduces ALI score in lungs of animals delivered EV from injured mice. FIG. 9A-9D illustrates H&E staining of lung sections from saline (FIG. 9A), untreated (FIG. 9B), Enoxaparin (FIG. 9C) and IC 100 (Anti-ASC; FIG. 9D) treated mice lungs delivered EV from injured animals. Sections show evidence of neutrophil infiltration, changes in morphology of alveolar capillary membranes, interstitial edema, and evidence of thickening of the interstitium and the alveolar septum. FIG. 9E illustrates that acute lung injury scoring is significantly decreased in animals treated with Enoxaparin, IC 100 when compared to untreated animals. Data presented as mean+/−SEM. N=4 per group, ****p<0.01, *p<0.05.

FIG. 10A-10F illustrates delivery of serum-derived EV from TBI patients results in increased inflammasome protein expression in pulmonary endothelial cells. FIG. 10A shows western blot representation of caspase-1, ASC, AIM2, HMGB1 in PMVEC after incubation with TBI-EV and control-EV for 4 hours. FIG. 10B-10E) shows quantification of western blots, n=3 filters per group, n=6 patients, t-test, **p<0.001, *p<0.01, **p<0.01, *p<0.05. FIG. 10F shows immunoassay results of a significant increase in IL-1β expression using Ella simple plex assay n=3 filters per group, n=6 patients, t-test, **p<0.001, *p<0.01, **p<0.01, *p<0.05.

FIG. 11A shows co-localization of Caspase-1 FLICA and PI staining and PMVEC incubated with TBI-EV for 4 hours. FIG. 11B shows caspsae-1 FLICA and PI staining in PMVEC incubated with control-EV for 4 hours. FIG. 11C shows fluorescent plate reader analysis of PMVEC incubated with TBI and control-EV for 4 hours. n=6, ***p<0.05.

FIG. 12A-12E illustrates that treatment with a humanized anti-ASC monoclonal antibody (i.e., IC-100) improves functional outcome in EAE. FIG. 12A shows the clinical course of $MOG_{35-55}$-induced EAE in C57BL/6 mice treated with vehicle or increasing doses of IC-100. Administration of IC-100 (10, 30 and 45 mg/Kg i.p. every 4 days) was initiated at day 8, before the mice showed signs of paralysis. Results are expressed as daily mean clinical score±SEM of 9-10 mice/group. The 30 and 45 mg/Kg curves are significantly different the vehicle curve; **p≤0.001 Mann-Whitney test. FIG. 12B shows a comparison of peak clinical scores (the highest disease score reached by a mouse) among groups; *p≤0.05, Student's t test. FIG. 12C shows a comparison of the Cumulative Disease Index (CDI) among groups. The CDI equals to the sum of all scores from day of onset for each animal and is a measure of EAE severity; *p<0.05, Student's t test. FIG. 12D shows a comparison of the onset day among groups. Day of onset is considered as the day a mouse showed the first EAE symptoms. FIG. 12E shows a comparison of the peak disease day among groups. Peak disease day is the day a mouse reached the highest disease score. Day of onset is considered as the day a mouse showed the first EAE symptoms.

FIG. 13A-13B illustrates that IC-100 treatment reduces peripheral immune cell infiltration into the spinal cord following EAE. Flow cytometric quantification of the leukocyte populations infiltrating into the spinal cord (FIG. 13A) or present in the spleen (FIG. 13B) at 35 dpi after EAE. Results are expressed as average±SEM of 5 mice/group, *p<0.05, **p<0.001, Student's t test.

DETAILED DESCRIPTION

Definitions

Figure 1I:
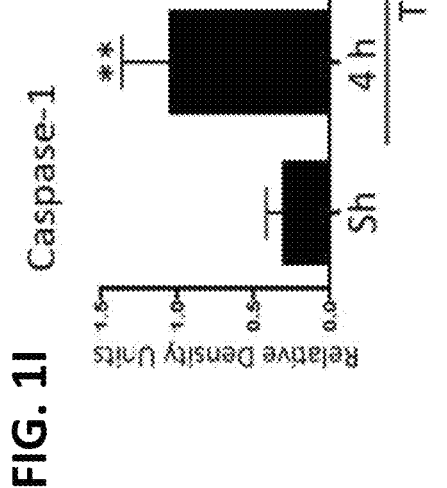
FIG. 1A-1N illustrate inflammasome activation in C57/BL6 mouse cortical and lung tissue post-TBI.
FIG. 1H shows a representative immunoblot of active caspase-1, ASC, IL-18, IL-β, HMGB1, and AIM2 in lung tissue. I, J, K, L, M, N) Active caspase-1 (FIG. 1I), ASC (FIG. 1J), IL-18 (FIG. 1K), HMGB1 (FIG. 1L), AIM 2 (FIG. 1M), and IL-β, (FIG. 1N) are significantly elevated in lung tissue 4 and 24 h after TBI. Data presented as mean+/−SEM. N=4-5 per group, **$p<0.001$, *$p<0.01$, **$p<0.01$, *$p<0.05$ compared to sham.
Figure 1J:
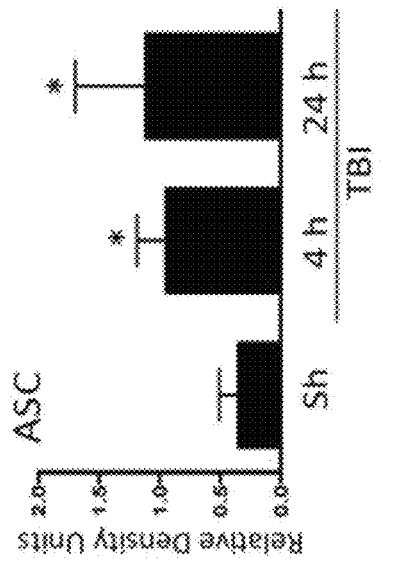
Figure 1H:
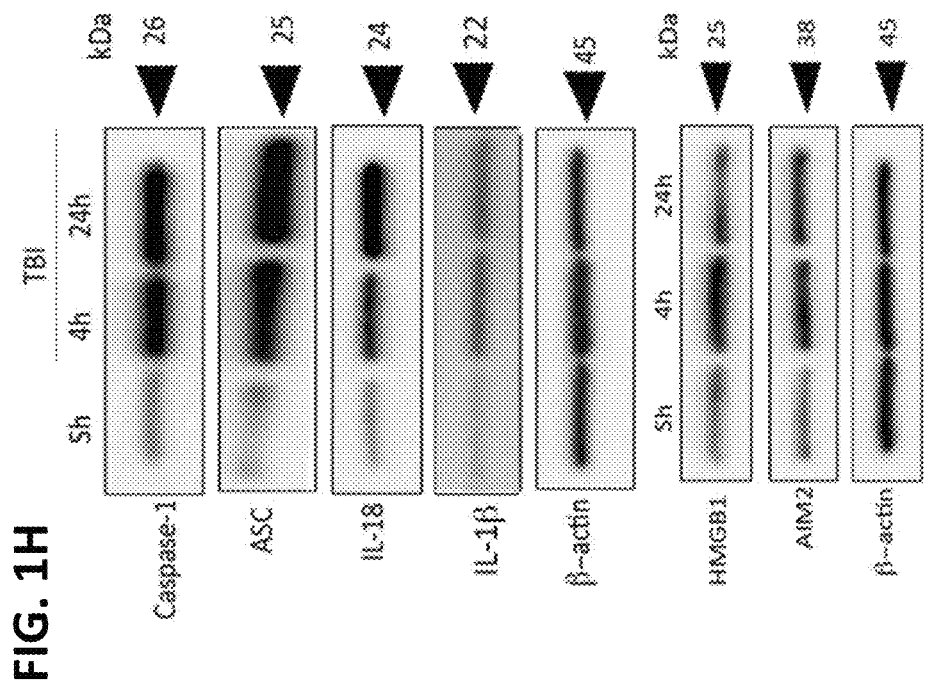
Figure 1K:
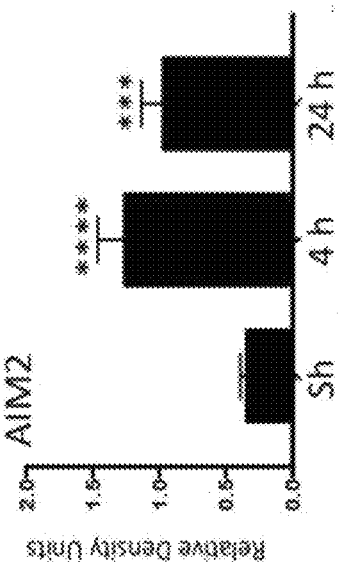
Figure 1M:
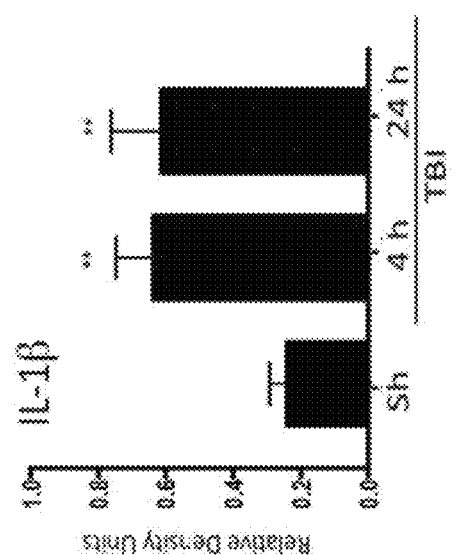
Figure 1L:
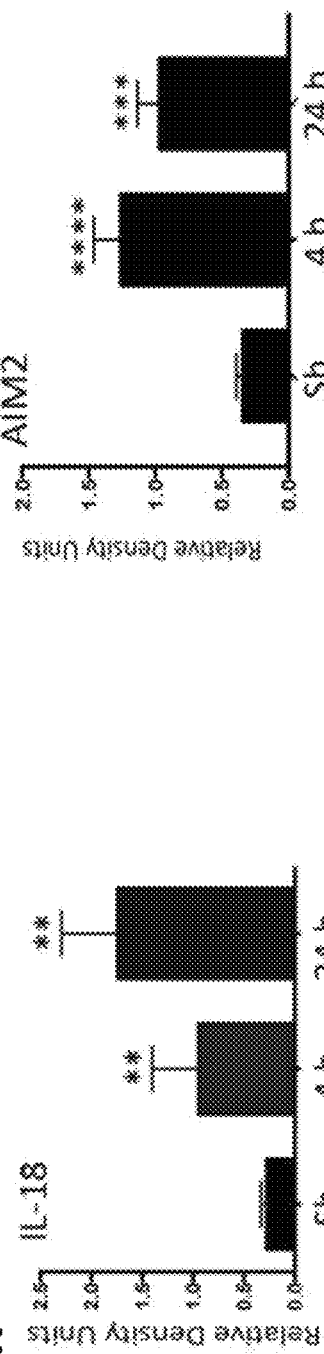
Figure 1N:
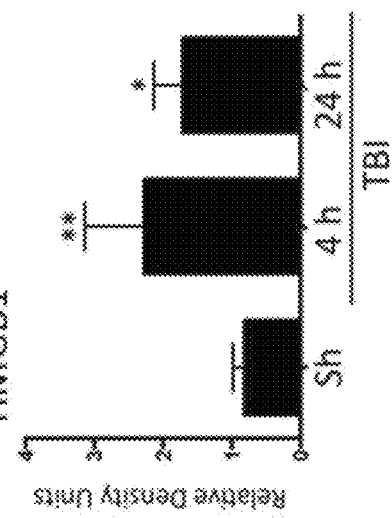

Unless otherwise defined, all technical terms used herein have the same meaning as commonly understood by one of ordinary skill in the art to which this invention belongs.

The section headings used herein are for organizational purposes only and are not to be construed as limiting the subject matter described. All documents, or portions of documents, cited herein, including but not limited to patents, patent applications, articles, books, and treatises, are hereby expressly incorporated by reference in their entirety for any purpose. In the event that one or more of the incorporated documents or portions of documents define a term that contradicts that term's definition in the application, the definition that appears in this application controls. However, mention of any reference, article, publication, patent, patent publication, and patent application cited herein is not, and should not be taken as an acknowledgment, or any form of suggestion, that they constitute valid prior art or form part of the common general knowledge in any country in the world.

The term "a" or "an" refers to one or more of that entity, i.e. can refer to a plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Unless the context requires otherwise, throughout the present specification and claims, the word "comprise" and variations thereof, such as, "comprises" and "comprising" are to be construed in an open, inclusive sense that is as "including, but not limited to". The use of the alternative (e.g., "or") should be understood to mean either one, both, or any combination thereof of the alternatives. As used herein, the terms "about" and "consisting essentially of" mean+/−20% of the indicated range, value, or structure, unless otherwise indicated.

Reference throughout this specification to "one embodiment" or "an embodiment" means that a particular feature, structure or characteristic described in connection with the embodiment may be included in at least one embodiment of the present disclosure. Thus, the appearances of the phrases "in one embodiment" or "in an embodiment" in various places throughout this specification may not necessarily all referring to the same embodiment. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

Throughout this disclosure, various aspects of the methods and compositions provided herein can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, "protein" and "polypeptide" are used synonymously to mean any peptide-linked chain of amino acids, regardless of length or post-translational modification, e.g., glycosylation or phosphorylation.

As used herein, the term "antibody" refers generally and broadly to immunoglobulins (Ig) molecules and immunologically active portions or fragments of immunoglobulin molecules, i.e., molecules that contain an antigen binding site that specifically binds (immunoreacts with) an antigen (e.g., ASC, NLRP1, AIM2, etc.). The antibodies provided herein can be polyclonal antibodies, monoclonal antibodies (mAbs), chimeric antibodies, humanized antibodies, anti-idiotypic (anti-Id) antibodies to antibodies that can be labeled in soluble or bound form, as well as active fragments, regions or derivatives thereof. The antibodies for use herein may be chimeric, humanized, or human.

By "specifically binds" or "immunoreacts with" is meant that the antibody reacts with one or more antigenic determinants of the desired antigen and does not react with other polypeptides. In certain embodiments, an antibody is said to specifically bind an antigen when it preferentially recognizes its target antigen in a complex mixture of proteins and/or macromolecules. The term "antibody" broadly refers to an immunoglobulin (Ig) molecule, generally comprising four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Such anti-ASC and anti-NLRP1 antibodies of the present invention are capable of binding portions of ASC and NLRP1, respectively, which interfere with caspase-1 activation.

As used herein, the term "humanized antibody" refers to an antibody in which minimal portions of a non-human antibody are introduced into an otherwise human antibody.

As used herein, the term "human antibody" refers to an antibody in which substantially every part of the protein is substantially non-immunogenic in humans, with only minor sequence changes or variations.

In a full-length antibody, each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG3, IgG4, IgA1 and IgA2) or subclass. IgG, IgD, and IgE antibodies generally contain two identical heavy chains and two identical light chains and two antigen combining domains, each composed of a heavy chain variable region (VH) and a light chain variable region (VL). Generally IgA antibodies are composed of two monomers, each monomer composed of two heavy chains and two light chains (as for IgG, IgD, and IgE antibodies); in this way the IgA molecule has four antigen binding domains, each again composed of a VH and a VL. Certain IgA antibodies are monomeric in that they are composed of two heavy chains and two light chains. Secreted IgM antibodies are generally composed of five monomers, each monomer composed of two heavy chains and two light chains (as for IgG and IgE antibodies); in this way the IgM molecule has ten antigen binding domains, each again composed of a VH and a VL. A cell surface form of IgM also exists and this has two heavy chain/two light chain structure similar to IgG, IgD, and IgE antibodies.

The term "antigen binding fragment" or "antigen binding portion" or "antigen binding site" or "binding domain" or "binding region", as used herein, can refer to the domain, region, portion, or site of a protein, polypeptide, oligopeptide, or peptide or antibody or binding domain derived from an antibody that retains the ability to specifically bind to an antigen (e.g., ASC protein). Exemplary binding domains include single-chain antibody variable regions (e.g., domain antibodies, sFv, scFv, scFab), fusion proteins comprising an antibody portion (e.g., a domain antibody), receptor ectodomains, and ligands (e.g., cytokines, chemokines). In one embodiment, the fusion protein comprises one or more CDR(s). In another embodiment, the fusion protein comprises CDR H3 (VH CDR3) and/or CDR L3 (VL CDR3). For purposes of this invention, a fusion protein contains one or more antibodies and additional amino acid sequence such as for example, a heterologous sequence or a homologous sequence from another region, attached to the N- or C-terminus of the antibody or antibody fragment thereof. Exemplary heterologous sequences include, but are not limited to a "tag" such as a FLAG tag or a 6His tag or an enzyme or a polypeptide which increases the half-life of the antibody in the blood. Tags are well known in the art. The additional amino acid sequence, which can include amino- and/or carboxyl-terminal fusions can range in length from one residue to polypeptides containing a hundred or more residues, as well as intra-sequence insertions of single or multiple amino acid residues.

An antigen binding site can be generally formed by the heavy chain variable region (VH) and the light chain variable region (VL) immunoglobulin domains, with the antigen-binding interface formed by six surface polypeptide loops, termed complimentarity determining regions (CDRs). There are three CDRs each in VH (HCDR1, HCDR2, HCDR3) and VL (LCDR1, LCDR2, LCDR3), together with framework regions (FRs). In certain embodiments, the binding domain comprises or consists of an antigen binding site (e.g., comprising a variable heavy chain sequence and variable light chain sequence or three light chain complementary determining regions (CDRs) and three heavy chain CDRs from an antibody placed into alternative framework regions (FRs) (e.g., human FRs optionally comprising one or more amino acid substitutions).

The term "CDR region" or "CDR" can be mean the hypervariable regions of the heavy or light chains of the immunoglobulin as defined by Kabat et al., 1991 (Kabat, E. A. et al., (1991) Sequences of Proteins of Immunological Interest, 5th Edition. US Department of Health and Human Services, Public Service, NIH, Washington), and later editions. An antibody typically contains 3 heavy chain CDRs and 3 light chain CDRs.

It has been shown that the antigen binding function of an antibody can be performed by fragments of a full-length antibody. Antibody and antibody fragment embodiments may also be bispecific, trispecific, dual specific, or multispecific formats; specifically binding to two or more different antigens. Examples of binding fragments encompassed within the term "antigen binding fragment" of an antibody include: (i) an Fab fragment consisting of VL, VH, CL and CH1 domains (Ward, E. S. et al., (1989) Nature 341, 544-546); (ii) an Fd fragment consisting of the VH and CH1 domains (McCafferty et al., (1990) Nature, 348, 552-554); (iii) an Fv fragment consisting of the VL and VH domains of a single antibody (Holt et al., (2003) Trends in Biotechnology 21, 484-490); (iv) a dAb fragment (Ward, E. S. et al., Nature 341, 544-546 (1989), McCafferty et al., (1990) Nature, 348, 552-554, Holt et al., (2003) Trends in Biotechnology 21, 484-490], which consists of a VH or a VL domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., (1988) Science, 242, 423-426, Huston et al., (1988) PNAS USA, 85, 5879-5883). The invention also encompasses an Fab' fragment. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv). Such single chain antibodies are also intended to be encompassed within the term "antigen binding fragment" of an antibody. In certain embodiments of the invention, scFv molecules may be incorporated into a fusion protein. In some embodiments, the invention includes a single chain camelid antibody; (viii) bispecific single chain Fv dimers (PCT/U.S. Pat. No. 92,109,965) and (ix) "diabodies", multivalent or multispecific fragments constructed by gene fusion (WO94/13804; Holliger, P. (1993) et al., Proc. Natl. Acad. Sci. USA 90 6444-6448). Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). Such antibody binding fragments are known in the art (Kontermann and Dubel eds., Antibody Engineering (2001) Springer-Verlag. New York. 790 pp.). In some aspects, the invention includes a single domain antibody. In general, the term "antibody" when used herein encompasses an "antibody fragment". An antibody fragment generally retains the antigen-binding properties of a full length antibody.

Fv, scFv or diabody molecules may be stabilized by incorporation of disulfide bridges linking the VH and VL domains (Reiter, Y. et al., Nature Biotech, 14, 1239-1245, 1996). Minibodies comprising a scFv joined to a CH3 domain may also be made (Hu, S. et al., (1996) Cancer Res., 56, 3055-3061). Other examples of binding fragments can be Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

"Fv" when used herein can refer to the minimum fragment of an antibody that retains both antigen-recognition and antigen-binding sites. "Fab" when used herein can refer to a fragment of an antibody that comprises the constant domain of the light chain and the CH1 domain of the heavy chain. The term "mAb" refers to monoclonal antibody.

"Fc region" or "Fc domain" refers to a polypeptide sequence corresponding to or derived from the portion of a source antibody that is responsible for binding to antibody receptors on cells and the C1q component of complement. Fc stands for "fragment crystalline," the fragment of an antibody that will readily form a protein crystal. Distinct protein fragments, which were originally described by proteolytic digestion, can define the overall general structure of an immunoglobulin protein. As originally defined in the literature, the Fc fragment consists of the disulfide-linked heavy chain hinge regions, CH2, and CH3 domains. However, more recently the term has been applied to a single chain consisting of CH3, CH2, and at least a portion of the hinge sufficient to form a disulfide-linked dimer with a second such chain. For a review of immunoglobulin structure and function, see Putnam, The Plasma Proteins, Vol. V (Academic Press, Inc., 1987), pp. 49-140; and Padlan, Mol. Immunol. 31:169-217, 1994. As used herein, the term Fc includes variants of naturally occurring sequences. In one embodiment, the antibodies or antibody fragments derived therefrom provided herein (e.g., the anti-ASC monoclonal antibodies or antibody fragments thereof) have a modified Fc region or domain. In some cases, the modified Fc region or domain can confer increased thermal stability to the resultant antibody or antibody fragment derived therefrom. The increased thermal stability can result in increased serum half-life. The Fc region or domain can be modified as described in US20160193295, the contents of which are herein incorporated by reference. As described in US20160193295, the Fc region or domain can be modified to possess a deletion of one or more cysteine residues in the hinge region and substitution with a sulfhydryl-containing residue of one or more CH3-interface amino acids. In another embodiment, the Fc region or domain of the antibodies or antibody fragments derived therefrom provided herein (e.g., the anti-ASC monoclonal antibodies or antibody fragments thereof) can be stabilized by engineering the Fc region to possess intradomain disulfide bonds as described in Wozniak-Knopp G, Stadlmann J, Rüker F (2012) Stabilisation of the Fc Fragment of Human IgG1 by Engineered Intradomain Disulfide Bonds. PLoS ONE 7(1): e30083, the contents of which are herein incorporated by reference. In yet another embodiment, the antibodies have Fc regions modified as described in WO 99/58572, which is herein incorporated by reference. In still other embodiments, the Fc region or domain can be modified as described in U.S. Pat. No. 9,574,010, the contents of which are herein incorporated by reference.

By the terms "Apoptosis-associated Speck-like protein containing a Caspase Activating Recruitment Domain (CARD)" and "ASC" is meant an expression product of an ASC gene or isoforms thereof, or a protein that shares at least 65%, 75%, 80%, 85%, 90%, 95%, 96%, 97%, 98%, or 99%) amino acid sequence identity with ASC (e.g., NP_037390 (Q9ULZ3-1), NP_660183 (Q9ULZ3-2) or Q9ULZ3-3 in human, NP_075747 in mouse or NP_758825 (BAC43754) in rat) and displays a functional activity of ASC. A "functional activity" of a protein is any activity associated with the physiological function of the protein. Functional activities of ASC include, for example, recruitment of proteins for activation of caspase-1 and initiation of cell death.

By the term "ASC gene," or "ASC nucleic acid" is meant a native ASC-encoding nucleic acid sequence, genomic sequences from which ASC cDNA can be transcribed, and/or allelic variants and homologues of the foregoing. The terms encompass double-stranded DNA, single-stranded DNA, and RNA.

As used herein, the term "inflammasome" means a multi-protein (e.g., at least two proteins) complex that activates caspase-1. Further, the term "inflammasome" can refer to a multi-protein complex that activates caspase-1 activity, which in turn regulates IL-1β, IL-18 and IL-33 processing and activation. See Arend et al. 2008; Li et al. 2008; and Martinon et al. 2002, each of which is incorporated by reference in their entireties. The terms "NLRP1 inflammasome", "NALP1 inflammasome", "NLRP2 inflammasome", "NALP2 inflammasome", "NLRP3 inflammasome", "NALP3 inflammasome", "NLRC4 inflammasome", "IPAF inflammasome" or "AIM2 inflammasome" mean a protein complex of at least caspase-1 and one adaptor protein, e.g., ASC. For example, the terms "NLRP1 inflammasome" and "NALP1 inflammasome" can mean a multiprotein complex containing NLRP1, ASC, caspase-1, caspase-11, XIAP, and pannexin-1 for activation of caspase-1 and processing of interleukin-1β, interleukin-18 and interleukin-33. The terms "NLRP2 inflammasome" and "NALP2 inflammasome" can mean a multiprotein complex containing NLRP2 (aka NALP2), ASC and caspase-1, while the terms "NLRP3 inflammasome" and "NALP3 inflammasome" can mean a multiprotein complex containing NLRP3 (aka NALP3), ASC and the terms "NLRC4 inflammasome" and "IPAF inflammasome" can mean a multiprotein complex containing NLRC4 (aka IPAF), ASC and caspase-1. Additionally, the term "AIM2 Inflammasome" can mean a multiprotein complex comprising AIM2, ASC and caspase-1.

As used herein, the phrase "sequence identity" means the percentage of identical subunits at corresponding positions in two sequences (e.g., nucleic acid sequences, amino acid sequences) when the two sequences are aligned to maximize subunit matching, i.e., taking into account gaps and insertions. Sequence identity can be measured using sequence analysis software (e.g., Sequence Analysis Software Package from Accelrys CGC, San Diego, CA).

By the phrases "therapeutically effective amount" and "effective dosage" is meant an amount sufficient to produce a therapeutically (e.g., clinically) desirable result; the exact nature of the result will vary depending on the nature of the disorder being treated. For example, where the disorder to be treated is SCI, the result can be an improvement in motor skills and locomotor function, a decreased spinal cord lesion, etc. The compositions described herein can be administered from one or more times per day to one or more times per week. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

As used herein, the term "treatment" is defined as the application or administration of a therapeutic agent described herein, or identified by a method described herein, to a patient, or application or administration of the therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease, or the predisposition toward disease.

The terms "patient" "subject" and "individual" are used interchangeably herein, and mean a mammalian subject to be treated. In one embodiment, the mammalian patient is human. In some cases, the methods of the invention find use in experimental animals, in veterinary applications, and in the development of animal models for disease, including, but not limited to, rodents including mice, rats, and hamsters, as well as primates.

As interchangeably used herein, "Absent in Melanoma 2" and "AIM2" can mean an expression product of an AIM2 gene or isoforms; or a protein that shares at least 65%, 75%, 80%, 85%, 90%, 95%, 96%, 97%, 98%, or 99% amino acid sequence identity with AIM2 (e.g., accession number(s) NX_014862, NP004824, XP016858337, XP005245673, AAB81613, BAF84731, AAH10940) and displays a functional activity of AIM2.

As interchangeably used herein, "NACHT, LRR and PYD domains-containing protein 1", "NALP1" and "NLRP1" mean an expression product of an NALP1 or NLRP1 gene or isoforms; or a protein that shares at least 65%, 75%, 80%, 85%, 90%, 95%, 96%, 97%, 98%, or 99% amino acid sequence identity with NALP1 (e.g., accession number(s) AAH51787, NP_001028225, NP_127500, NP_127499, NP_127497, NP055737) and displays a functional activity of NALP1.

As interchangeably used herein, "NALP2" and "NLRP2" mean an expression product of an NALP2 or NLRP2 gene or isoforms; or a protein that shares at least 65%, 75%, 80%, 85%, 90%, 95%, 96%, 97%, 98%, or 99% amino acid sequence identity with NALP2 (e.g., accession number(s) NP_001167552, NP_001167553, NP_001167554 or NP_060322) and displays a functional activity of NALP2.

As interchangeably used herein, "NALP3" and "NLRP3" mean an expression product of an NALP3 or NLRP3 gene or isoforms; or a protein that shares at least 65%, 75%, 80%, 85%, 90%, 95%, 96%, 97%, 98%, or 99% amino acid sequence identity with NALP3 (e.g., accession number(s) NP_001073289, NP_001120933, NP_001120934, NP_001230062, NP_004886, NP_899632, XP_011542350, XP_016855670, XP_016855671, XP_016855672 or XP_016855673) and displays a functional activity of NALP3.

As interchangeably used herein, "NLRC4" and "IPAF" mean an expression product of an NLRC4 or IPAF gene or isoforms; or a protein that shares at least 65%, 75%, 80%, 85%, 90%, 95%, 96%, 97%, 98%, or 99% amino acid sequence identity with NLRC4 (e.g., accession number(s) NP_001186067, NP001186068, NP_001289433 or NP_067032) and displays a functional activity of NLRC4.

By the terms "stroke" and "ischemic stroke" is meant when blood flow is interrupted to part of the brain or spinal cord.

By "traumatic injury to the CNS" is meant any insult to the CNS from an external mechanical force, possibly leading to permanent or temporary impairments of CNS function.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Immunology techniques are generally known in the art and are described in detail in methodology treatises such as Advances in Immunology, volume 93, ed. Frederick W. Alt, Academic Press, Burlington, MA, 2007; Making and Using Antibodies: A Practical Handbook, eds. Gary C. Howard and Matthew R. Kaser, CRC Press, Boca Raton, FL, 2006; Medical Immunology, 6$^{th}$ ed., edited by Gabriel Virella, Informa Healthcare Press, London, England, 2007; and Harlow and Lane ANTIBODIES: A Laboratory Manual, Cold Spring Harbor Laboratory Press, Cold Spring Harbor, NY, 1988.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

Overview

Provided herein are monoclonal antibodies or an antibody fragments thereof that bind specifically to Apoptosis-associated Speck-like protein containing a Caspase Activating Recruitment Domain (ASC). The monoclonal antibodies or fragments thereof can bind specifically to an antigenic fragment of ASC that comprises, consists of or consists essentially of an amino acid sequence of SEQ ID NO. 5. Further to this embodiment, the invention contemplates use of the monoclonal antibodies or antibody fragments thereof in a method for treating inflammation in a subject. The inflammation can be an innate immune inflammation. The inflammation can be an inflammasome-related inflammation. In one embodiment, the monoclonal antibodies or antibody fragments thereof provided herein can be used in a method for reducing inflammation in a mammal as described in U.S. Pat. No. 8,685,400, the contents of which are herein incorporated by reference in their entirety. The inflammation can be in the lungs and/or the central nervous system (CNS). The inflammation in the lungs and/or the CNS can be the result of an infection (viral or bacterial), an injury (e.g., traumatic brain injury (TBI) or spinal cord injury (SCI)) or disease, condition or affliction of the CNS or affecting the CNS. The viral infection can be caused by a coronavirus, such as SARS-CoV-2, or an influenza virus, such as influenza A H5N1 (avian influenza) and influenza A H1N1 (swine flu). As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). The monoclonal antibodies and fragments thereof described herein may be used prophylactically, in methods of preventing inflammation associated with any of the disorders disclosed herein.

The patients to be treated by the methods of the invention may be experiencing a hyperinflammatory response also known as cytokine storm syndrome. Cytokine storm syndrome is a secondary haemophagocytic lymphohistocytosis (sHLH) characterized by fulminant hypercytokemia that results in multiorgan failure (Mehta, McAuley et al. 2020). The antibodies, antibody fragments and methods of the invention may be used to treat or prevent hyperinflammation or cytokine storm syndrome associated with a viral infection, including hyperinflammation and cytokine storms associated with SARS-CoV-2 infections.

Figure 15:
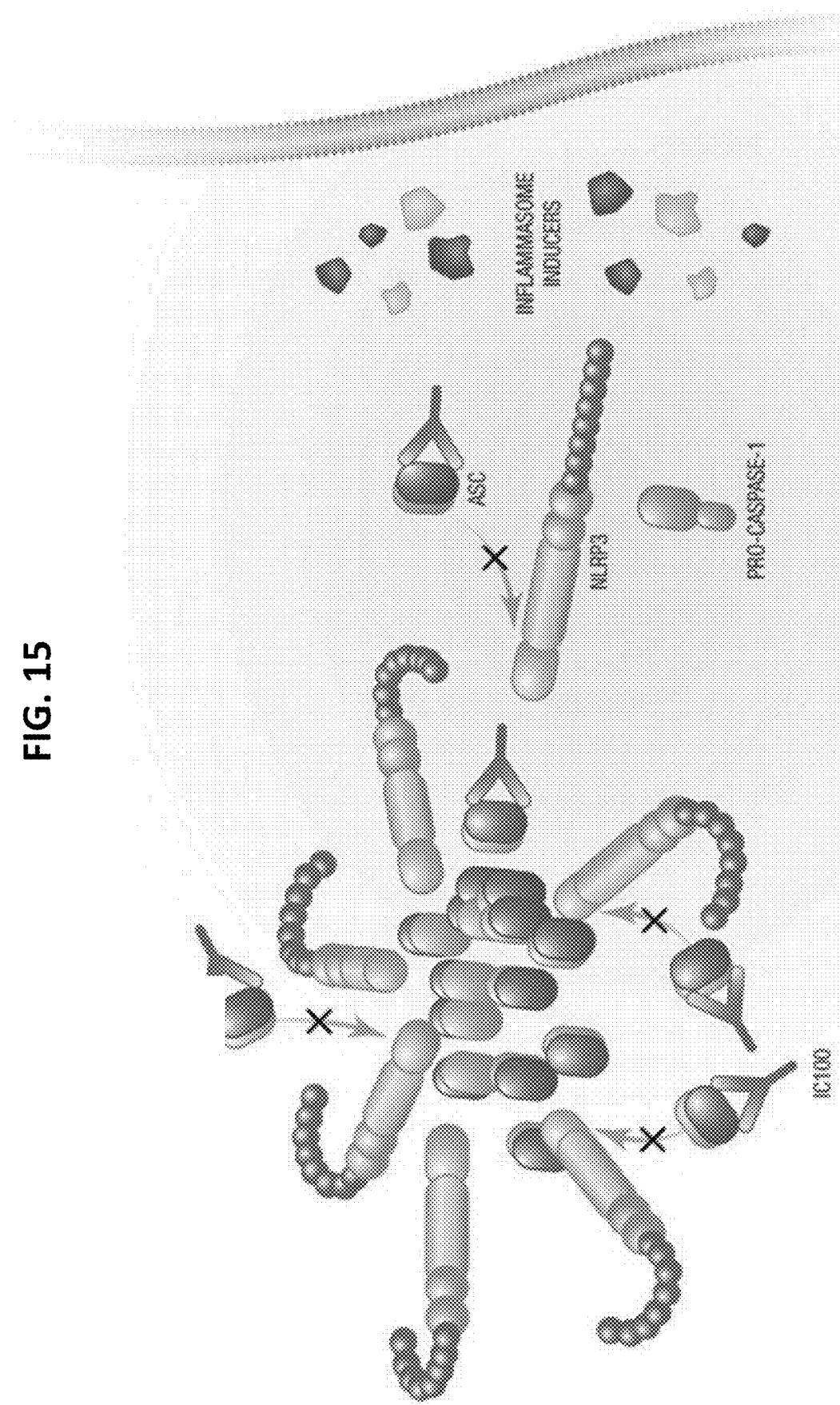
FIG. 15 illustrates how IC-100 inhibits inflammasome formation, blocking initiation of the immune response.
Figure 16:
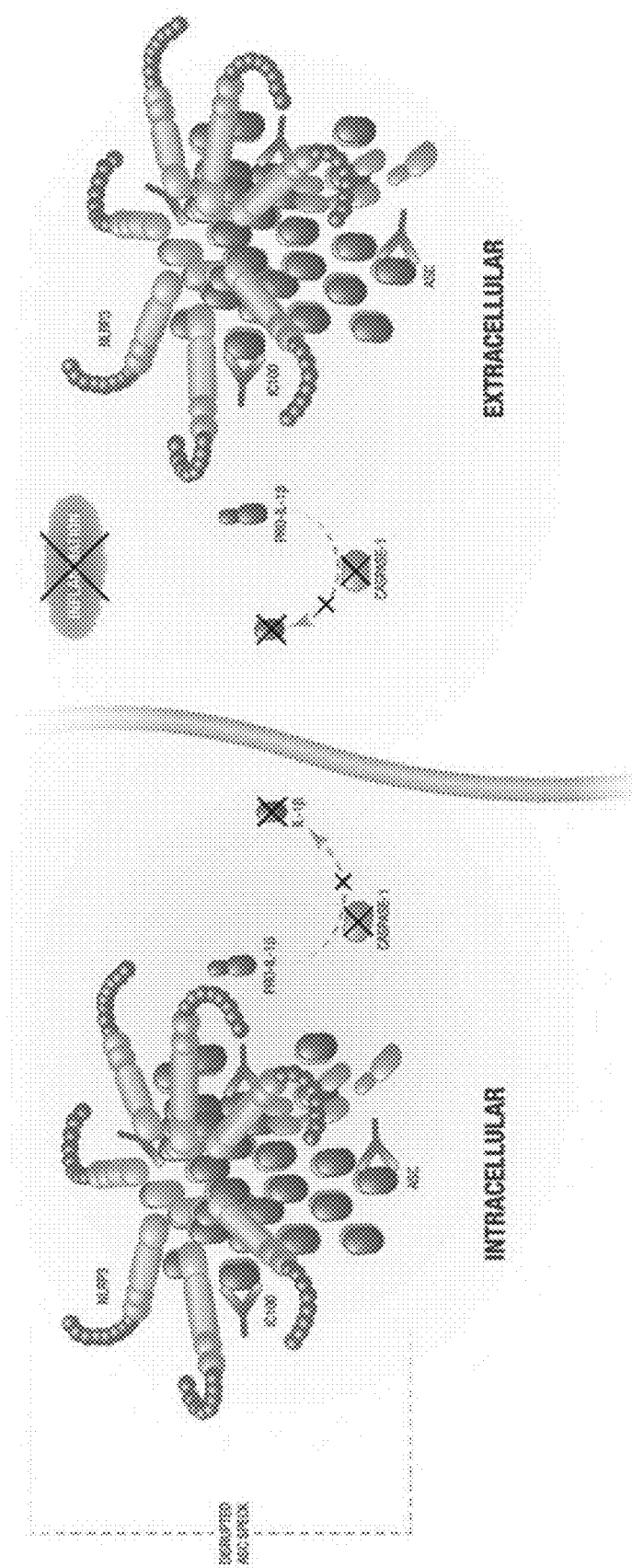
FIG. 16 illustrates how IC 100 inhibits ASC in ASC specks, preventing perpetuation of inflammation.

Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In some embodiments, the antibodies and fragments thereof employed in the methods described herein bind to and inhibit the ASC part of the inflammasome, thus preventing assembly of the multi-protein inflammasome required for initiation of the inflammatory response (FIG. 15). The antibodies and fragments thereof may also bind to and inhibit ASC in ASC specks or ASC monomers, both intracellulary and extracellularly. This inhibits propagation of the large filamentous signaling platform, preventing perpetuation of inflammation associated with chronic inflammatory diseases mediated by ASC-dependent inflammasomes (FIG. 16).

In one embodiment, the monoclonal antibody or antibody fragment derived therefrom is used to treat lung inflammation associated with a viral infection by administering the monoclonal antibody or antibody fragment derived therefrom to a patient suffering from or suspected of suffering from viral-associated lung inflammation, including ARDS and/or ALI. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NLRP1, NLRP3, AIM2, etc.). In some cases, the other agents can be those having possible utility in treating viral infections or the body's hyper-response to viral infections, including hydroxychloroquine, chloroquine, and immunosuppressive drugs including but not limited to steroids, selective cytokine blockade (eg, anakinra or tocilizumab), JAK inhibitors, interleukin inhibitors, including IL-1β and IL-6 inhibitors, TNF inhibitors, and CSF inhibitors, as well as anti-coagulants such as low molecular weight heparin, tissue plasminogen activator or Enoxaparin.

In one embodiment, the monoclonal antibody or antibody fragment derived therefrom is used to treat MS by administering the monoclonal antibody or antibody fragment derived therefrom to a patient suffering from or suspected of suffering from MS. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NALP1, AIM2, etc.).

The invention also encompasses monoclonal antibodies or antibody fragments thereof that binds specifically to ASC, wherein the antibody or the antibody fragment comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3. Further to this embodiment, the invention contemplates use of the monoclonal antibody or antibody fragment thereof in a method for treating inflammation in a subject. The inflammation can be an innate immune inflammation. The inflammation can be an inflammasome-related inflammation. In one embodiment, the monoclonal antibodies or antibody fragments thereof provided herein can be used in a method for reducing inflammation in a mammal as described in U.S. Pat. No. 8,685,400, the contents of which are herein incorporated by reference in their entirety. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. Use of the monoclonal antibody or antibody fragment thereof in a method for treating inflammation can reduce innate immune or inflammasome-related inflammation in the patient. The reduction can be as compared to a control (e.g., untreated patient and/or patient prior to treatment). In one embodiment, the monoclonal antibody or antibody fragment derived therefrom is used to treat lung inflammation associated with a viral infection by administering the monoclonal antibody or antibody fragment derived therefrom to a patient suffering from or suspected of suffering from viral-associated lung inflammation, including ARDS and/or ALI. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NLRP1, NLRP3, AIM2, etc.). In some cases, the other agents can be those having possible utility in treating viral infections or the body's hyper-response to viral infections, including hydroxychloroquine, chloroquine, and immunosuppressive drugs including but not limited to steroids, selective cytokine blockade (eg, anakinra or tocilizumab), JAK inhibitors, interleukin inhibitors, including IL-1β and IL-6 inhibitors, TNF inhibitors, and CSF inhibitors as well as anti-coagulants such as low molecular weight heparin, tissue plasminogen activator or Enoxaparin. In one embodiment, the monoclonal antibody or antibody fragment derived therefrom is used to treat MS by administering the monoclonal antibody or antibody fragment derived therefrom to a patient suffering from or suspected of suffering from MS. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NALP1, AIM2, etc.).

In some embodiments, the invention provides monoclonal antibodies or an antibody fragments thereof that binds specifically to ASC, wherein the antibody or the antibody fragment comprises a light chain variable (VL) region and a heavy chain variable (VH) region, wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3. Further to this embodiment, the invention contemplates use of the monoclonal antibody or antibody fragment thereof in a method for treating inflammation in a subject. The inflammation can be an innate immune inflammation. The inflammation can be an inflammasome-related inflammation. In one embodiment, the monoclonal antibodies or antibody fragments thereof provided herein can be used in a method for reducing inflammation in a mammal as described in U.S. Pat. No. 8,685,400, the contents of which are herein incorporated by reference in their entirety. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. Use of the monoclonal antibody or antibody fragment thereof in a method for treating inflammation can reduce innate immune or inflammasome-related inflammation in the patient. The reduction can be as compared to a control (e.g., untreated patient and/or patient prior to treatment). In one embodiment, the monoclonal antibody or antibody fragment derived therefrom is used to treat lung inflammation associated with a viral infection by administering the monoclonal antibody or antibody fragment derived therefrom to a patient suffering from or suspected of suffering from viral-associated lung inflammation, including ARDS and/or ALI. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NALP1, AIM2, etc.). In some cases, the other agents can be those having possible utility in treating viral infections or the body's hyper-response to viral infections, including hydroxychloroquine, chloroquine, and immunosuppressive drugs including but not limited to steroids, selective cytokine blockade (eg, anakinra or tocilizumab), JAK inhibitors, interleukin inhibitors, including IL-1β and IL-6 inhibitors, TNF inhibitors, and CSF inhibitors as well as anti-coagulants such as low molecular weight heparin, tissue plasminogen activator or Enoxaparin. In one embodiment, the monoclonal antibody or antibody fragment derived therefrom is used to treat MS by administering the monoclonal antibody or antibody fragment derived therefrom to a patient suffering from or suspected of suffering from MS. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NALP1, AIM2, etc.).

In other embodiments, the invention also provides monoclonal antibodies or an antibody fragments thereof that binds specifically to ASC, wherein the antibody or the antibody fragment comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3; and wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3. Further to this embodiment, the invention contemplates use of the monoclonal antibody or antibody fragment thereof in a method for treating inflammation in a subject. The inflammation can be an innate immune inflammation. The inflammation can be an inflammasome-related inflammation. In one embodiment, the monoclonal antibodies or antibody fragments thereof provided herein can be used in a method for reducing inflammation in a mammal as described in U.S. Pat. No. 8,685,400, the contents of which are herein incorporated by reference in their entirety. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. Use of the monoclonal antibody or antibody fragment thereof in a method for treating inflammation can reduce innate immune or inflammasome-related inflammation in the patient. The reduction can be as compared to a control (e.g., untreated patient and/or patient prior to treatment). In one embodiment, the monoclonal antibody or antibody fragment derived therefrom is used to treat lung inflammation associated with a viral infection by administering the monoclonal antibody or antibody fragment derived therefrom to a patient suffering from or suspected of suffering from viral-associated lung inflammation, including ARDS and/or ALI. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NLRP1, NLRP3, AIM2, etc.). In some cases, the other agents can be those having possible utility in treating viral infections or the body's hyper-response to viral infections, including hydroxychloroquine, chloroquine, and immunosuppressive drugs including but not limited to steroids, selective cytokine blockade (eg, anakinra or tocilizumab), JAK inhibitors, interleukin inhibitors, including IL-1β and IL-6 inhibitors, TNF inhibitors, and CSF inhibitors as well as anti-coagulants such as low molecular weight heparin, tissue plasminogen activator or Enoxaparin. In one embodiment, the monoclonal antibody or antibody fragment derived therefrom is used to treat MS by administering the monoclonal antibody or antibody fragment derived therefrom to a patient suffering from or suspected of suffering from MS. The monoclonal antibody or antibody fragment thereof of this embodiment can be present in a composition such as, for example, a pharmaceutical composition as provided herein. In some cases, the monoclonal antibody or fragment thereof is used in combination with one or more other agents in the methods of treatment provided herein. The other agents can be any agent provided herein (e.g., EV uptake inhibitors) and/or antibodies or antibody fragments directed against other inflammasome components (e.g., IL-18, caspase-1, NALP1, AIM2, etc.).

Provided herein are compositions and methods for reducing innate immune or inflammasome-related inflammation. In some cases, the inflammasome-related inflammation is in the CNS of a mammal that has been subjected to or is afflicted by a condition that results in or causes innate immune or inflammasome-related inflammation. The compositions and methods described herein can include antibodies or active fragments thereof as provided herein that specifically bind to at least one component (e.g., ASC) of a mammalian inflammasome and/or compounds that modulate (e.g., inhibit or reduce) extracellular vesicle (EV) uptake and have use as treatments for CNS inflammation in a mammal. Examples of conditions that can lead to inflammation in the CNS include a viral infection, a CNS injury (e.g., spinal cord injury (SCI), traumatic brain injury (TBI) or stroke), a neurodegenerative disease, an autoimmune disease (e.g., MS), asthma, chronic obstructive pulmonary disease (COPD), cystic fibrosis, interstitial lung disease or acute respiratory distress syndrome. The composition can be administered in a therapeutically effective amount. The therapeutically effective amount can be a dose as provided herein. The agent can be an extracellular vesicle (EV) uptake inhibitor and/or an antibody or an active fragment thereof as provided herein that binds to a component of an inflammasome or a combination thereof. The composition can be administered by any suitable route, e.g., by inhalation, intravenously, intraperitoneally, intranasally or intracerebroventricularly. The composition can further include at least one pharmaceutically acceptable carrier or diluent.

Provided herein are compositions and methods for treating a viral infection or lung inflammation in a subject that is suffering from or is suspected of suffering from a viral infection, including ARDS. The methods for treating viral-associated lung inflammation provided herein can entail administering a composition (e.g., a pharmaceutical composition) comprising an agent to the subject suffering from or suspected of suffering from lung inflammation. The subject can present with clinical symptoms consistent with viral infection. The subject can be diagnosed with any type of virus known in the art. The virus can be a coronavirus, such as SARS-CoV-2, MERS coronavirus, Herpes viruses, such as herpes simplex virus (HSV) and cytomegalovirus (CMV), or an influenza virus, such as influenza A H5N1 (avian influenza) and influenza A H1N1 (swine flu).

Provided herein are compositions and methods for treating Multiple Sclerosis (MS) in a subject that is suffering from or is suspected of suffering from MS. The methods for treating MS provided herein can entail administering a composition (e.g., a pharmaceutical composition) comprising an agent to the subject suffering from or suspected of suffering from MS. Multiple sclerosis (MS) is an autoimmune disease that affects the brain and spinal cord. The subject can present with clinical symptoms consistent with MS. The subject can be diagnosed with any type of MS known in the art. The MS can be relapsing-remitting MS (RRMS), secondary-progressive MS (SPMS), primary-progressive MS (PPMS), or progressive-relapsing MS (PRMS). The MS diagnosis can be or can have been determined using any method known in the art. In one embodiment, the subject has been diagnosed as having MS using the methods detail in U.S. 62/560,963, filed Sep. 20, 2017, the contents of which are herein incorporated by reference in their entirety.

The agent can be a standard of care treatment known in the art for MS or viral infections, an EV uptake inhibitor (e.g., any EV uptake inhibitor from Table 1), an antibody or antibody fragment thereof as provided herein that binds to a component of an inflammasome (e.g., an anti-ASC monoclonal antibody or antibody fragment thereof) or any combination thereof. The composition can be administered by any suitable route, e.g., by inhalation, intravenously, intraperitoneally, intranasally or intracerebroventricularly. The composition can further include at least one pharmaceutically acceptable carrier or diluent. The standard of care treatment can be selected from therapies directed towards modifying disease outcome, managing relapses, managing symptoms or any combination thereof. The therapies directed toward modifying disease outcome can be selected from beta-interferons, glatiramer acetate, fingolimod, teriflunomide, dimethyl fumarate, mitoxanthrone, ocrelizumab, alemtuzumab, daclizumab and natalizumab.

Provided herein are compositions and methods for reducing inflammation in the lungs of a mammal that has been subjected to or is afflicted by a condition that results in or causes lung inflammation. The compositions and methods described herein can include antibodies or active fragments thereof as provided herein that specifically bind to at least one component (e.g., ASC) of a mammalian inflammasome and/or compounds that modulate (e.g., inhibit or reduce) extracellular vesicle (EV) uptake and have use as treatments for lung inflammation in a mammal.

Described herein are methods for reducing inflammation in the lungs of a mammal having a condition that results in and/or causes an inflammatory response in the lungs. In one embodiment, the method of treating inflammation in the lungs of a mammal comprises administering to the mammal a composition comprising an agent that inhibits inflammasome signaling. The mammal can be a patient or subject as provided herein. Examples of conditions that can lead to inflammation in the lungs include a central nervous system (CNS) injury (e.g., spinal cord injury (SCI), traumatic brain injury (TBI) or stroke), a neurodegenerative disease, an autoimmune disease (e.g., MS), asthma, chronic obstructive pulmonary disease (COPD), cystic fibrosis, interstitial lung disease or acute respiratory distress syndrome. The composition can be administered in a therapeutically effective amount. The therapeutically effective amount can be a dose as provided herein. The agent can be an extracellular vesicle (EV) uptake inhibitor, an antibody or an active fragment thereof as provided herein that binds to a component of an inflammasome or a combination thereof. The composition can be administered by any suitable route, e.g., by inhalation, intravenously, intraperitoneally, intranasally, or intracerebroventricularly. The composition can further include at least one pharmaceutically acceptable carrier or diluent.

In one embodiment, administration of an agent (e.g., antibody or antibody fragment derived therefrom alone or in combination, for example, with an EV uptake inhibitor) in the methods provided herein can result in a reduction in the activity and/or expression level of a component of a mammalian inflammasome in the CNS or lungs of the subject. The reduction can be in cells of the lung such as, for example, Type II alveolar cells. The reduction can be in comparison to a control. The control can be the subject prior to administration of the agent. The control can be the activity and/or expression level of the inflammasome component(s) in a subject not administered the agent. In one embodiment, administration of the agent results in the reduction of caspase-1 activation in at least the CNS or CNS cells of the subject. In one embodiment, administration of the agent results in the reduction of caspase-1 activation in at least the lungs or lung cells of the subject. In one embodiment, administration of the agent results in the reduction of the expression level of one or more inflammasome components (e.g., ASC, AIM2, NALP1, NALP2, NALP2, NALP3 or NLRC4) in at least the CNS or CNS cells of the subject. In one embodiment, administration of the agent results in the reduction of the expression level of one or more inflammasome components (e.g., ASC, AIM2, NALP1, NALP2, NALP2, NALP3 or NLRC4) in at least the lungs or lung cells of the subject.

In another embodiment, administration of the agent (e.g., antibody or antibody fragment derived therefrom alone or in combination, for example, with an EV uptake inhibitor) can result in a reduction in or elimination of acute lung injury (ALI). In one embodiment, the reduction in ALI is evidenced by a reduction in neutrophil infiltration into alveolar and/or interstitial space, reduced or absent alveolar septal thickening or a combination thereof. The reduction can be in comparison to a control. The control can be ALI in the subject prior to administration of the agent. The control can be ALI in a subject suffering from ALI not administered the agent.

In still another embodiment, administration of the agent (e.g., antibody or antibody fragment derived therefrom alone or in combination, for example, with an EV uptake inhibitor) can result in a reduction in or elimination of pyroptosis in the CNS or lungs of the subject. Pyroptosis is a proinflammatory form of cell death that involves activation of caspase-1. Pyroptosis can be triggered by the caspase-1 mediated cleavage of gasdermin D (GSDMD). In one embodiment, the reduction in pyroptosis is evidenced by a reduction in or lack of cleavage of GSDMD in the lungs or lung cells (e.g., Type II alveolar cells) of the subject. The reduction or elimination of pyroptosis can be in comparison to a control. The reduction in or lack of cleavage of GSDMD can be in comparison to a control. The control can be the level of pyroptosis in the subject prior to administration of the agent. The control can be the level of pyroptosis in a subject suffering from pyroptosis not administered the agent.

The success of, or response to, a method of treatment provided herein (e.g., treating MS, innate immune or inflammasome-related inflammation, CNS inflammation and/or lung inflammation) can be monitored by measuring the levels of at least one inflammasome protein. Accordingly, in some embodiments, the methods of treating provided herein further comprise measuring the level of at least one inflammasome protein in a biological sample obtained from the subject following treatment, preparing a treatment inflammasome protein signature associated with a positive response to the treatment, wherein the treatment protein signature comprises a reduced level of at least one inflammasome protein, and identifying subjects exhibiting the presence of the treatment protein signature as responding positively to the treatment. A reduction in the level, abundance, or concentration of one or more inflammasome proteins (e.g. ASC, IL-18 or caspase-1) is indicative of the efficacy of the treatment in the subject. The one or more inflammasome proteins measured in the sample obtained following treatment may be the same as or different than the inflammasome proteins measured in a sample obtained prior to treatment. The inflammasome protein levels may also be used to adjust dosage or frequency of a treatment. The inflammasome protein levels can be ascertained using the methods and techniques provided herein or as found in US WO 2019/060516, filed Sep. 20, 2018.

In one embodiment, the agent to be administered in the method of treatments provided herein is an EV uptake inhibitor. The EV uptake inhibitor can be a compound, antisense RNA, siRNA, peptide, antibody or an active fragment thereof as provided herein or a combination thereof. The compound or peptide can be one or more compounds selected from heparin, α-difluoromethylornithine (DFMO), Enoxaparin, Asialofetuin, Human receptor-associated protein (RAP), RGD (Arg-Gly-Asp) peptide, Cytochalasin D, Cytochalasin B, Ethylenediaminetetra acetic acid (EDTA), Latrunculin A, Latrunculin B, NSC23766, Dynasore, Chlorpromazine, 5-(N-Ethyl-N-isopropyl) amiloride (EIPA), Amiloride, Bafilomycin A Monensin and Chloroquine, Annexin-V, Wortmannin, LY294002, Methyl-β-cyclodextrin (MPCD), Filipin, Simvastatin, Fumonisin B1 and N-butyldeoxynojirimycin hydrochloride, U0126 or a proton pump inhibitor. The EV uptake inhibitor antibody or an active fragment thereof as provided herein can be one or more antibodies or active fragments thereof directed against protein targets listed in Table 1. A composition for treating and/or reducing inflammation in the CNS or lungs of a mammal using an EV uptake inhibitor can further include at least one pharmaceutically acceptable carrier or diluent.

TABLE 1

Exemplary targets and corresponding antibodies for use in blocking EV uptake.

| Gene Symbol | Gene Name | Exemplary Antibodies |
| --- | --- | --- |
| ICAM-1 | Intercellular Adhesion Molecule 1 | Invitrogen ICAM-1 antibody (Life Technologies, 07-5403); CD54 (ICAM-1) Monoclonal Antibody (R6.5), eBioscience ™ |
| LFA-1 | Lymphocyte function-associated antigen 1 | Abbiotec LFA-1 antibody (Abbiotec, 250944); Developmental Studies Hybridoma Bank LFA-1 antibody (Developmental Studies Hybridoma Bank, MHM24) |

TABLE 1-continued

Exemplary targets and corresponding antibodies for use in blocking EV uptake.

| Gene Symbol | Gene Name | Exemplary Antibodies |
| --- | --- | --- |
| TIM-4 | T-cell membrane protein 4 | BioLegend TIMD4 antibody (BioLegend, 354004); LifeSpan Biosciences TIMD4 antibody (Lifespan Biosciences, LS-B1413) |
| MFG-E8 | Milk Fat Globule-EGF Factor 8 Protein | MBL International MFGE8 antibody (MBL, D199-3); Santa Cruz Biotechnology MFGE8 antibody (Santa Cruz, sc-8029); MBL International MFGE8 antibody (MBL, 18A2-G10) |
| DC-SIGN | Dendritic Cell-Specific Intercellular adhesion molecule-3-Grabbing Non-integrin | Invitrogen DC SIGN antibody (eBioscience, eB-h209, 17-2099-41); BD Biosciences DC SIGN antibody (BD, DCN46, 551186) |
| DEC205 | cluster of differentiation 205 | EMD Millipore LY75 antibody (Millipore, HD30); BioLegend LY75 antibody (BioLegend, 342203) |
| H-2Kb | MHC Class I (H-2Kd) | BioLegend H2-K1 antibody (BioLegend, 28-8-6, 114603); BioLegend H2-K1 antibody (BioLegend, 28-14-8, 14-5999-85) |
| Tspan8 | Tetraspanin-8 | R and D Systems TSPAN8 antibody (R&D Systems, MAB4734) |
| Tspan29 | Tetraspanin-29 | Santa Cruz Biotechnology CD9 antibody (Santa Cruz, sc-59140); Invitrogen CD9 antibody (eBioscience, eBioSN4; BD Biosciences CD9 antibody (BD Pharmingen, 555370) |
| ITGAL | Integrin subunit alpha L | TS1/22.1.1.13.3; M17/4.4.11.9 |
| ITGAM | Integrin subunit alpha M | CD11b Monoclonal Antibody (VIM12)(CD11B00); BD Biosciences CD11b antibody (BD Pharmingen, ICRF44; 555385) |
| ITGAX | Integrin subunit alpha X | Anti-Integrin αX Antibody, clone N418 (MAB1399Z); BD Biosciences CD11c antibody (BD Bioscience, B-ly6; 560369) |
| CD44 | Cluster of differentiation 44 | Invitrogen CD44 antibody (eBioscience, VFF-7; MA1-82392); Invitrogen CD44 antibody (eBioscience, IM7; MA1-10225); Invitrogen CD44 antibody (eBioscience, 5F12; MA5-12394); BD Biosciences CD44 antibody (BD Biosciences, 515; 550990 OR 550988) |
| ITGA3 | Integrin subunit alpha 3 | EMD Millipore integrin alpha3 antibody (Millipore, P1B5; MAB1952Z OR MAB1952P) |
| ITGA4 | Integrin subunit alpha 4 | Bio X Cell ITGA4 antibody (BioXcell, PS/2) (BE0071-5MG); BD Biosciences ITGA4 antibody (BD Biosciences, 561892); BD Biosciences ITGA4 antibody (BD, 340976); EMD Millipore ITGA4 antibody (Millipore, P4C2; MAB1955) |
| ITGAV | Integrin subunit alpha V | Abcam integrin alpha v antibody (Abcam, ab77906); Abcam integrin alpha v antibody (Abcam, ab78289); Abcam integrin alpha v antibody (Abcam, ab16821); Invitrogen integrin alpha v antibody (Thermo Fisher Scientific, 272-17E6, MA1-91669); R & D Systems integrin alpha v antibody (R&D Systems, MAB2528) |
| ITGB3 | Integrin subunit beta 3 | Abcam integrin beta3 antibody (Abcam, ab78289); Abnova integrin beta3 antibody (Abnova, MHF4, MAB7098) |
| SELL | Selectin L | BioLegend CD62L antibody (Biolegend, 304804); BioLegend CD62L antibody (Biolegend, 304810) |
| CD81 | CD81 molecule | BD Biosciences CD81 antibody (BD Pharmingen, 555675); R and D Systems CD81 antibody (R&D Systems, MAB4615) |

TABLE 1-continued

Exemplary targets and corresponding antibodies for use in blocking EV uptake.

| Gene Symbol | Gene Name | Exemplary Antibodies |
| --- | --- | --- |
| LRP1 | LDL receptor related protein 1 | Invitrogen LRP1 antibody (Life Technologies, 37-7600); Invitrogen LRP1 antibody (Thermo Fisher, MA1-27198) |
| VCAM1 | vascular cell adhesion molecule 1 | Invitrogen VCAM-1 antibody (Caltag, IG11B1; MA5-16429); Immunotech anti-VCAM-1 antibody |
| CD151 | CD151 molecule (Raph blood group) | BD Biosciences CD151 antibody (Becton Dickinson, 556056); Epitomics CD151 antibody (Epitomics, 5901-1) |

In one embodiment, the agent to be administered is an antibody or an active fragment thereof as provided herein directed against a component of a mammalian inflammasome or an antigen or epitope derived therefrom. In another embodiment, the agent to be administered is an antisense RNA or siRNA directed against a component of a mammalian inflammasome. The inflammasome component can be a component of any inflammasome known in the art, such as, for example, the NAPL1, NALP2, NALP3, NLRC4 or AIM2 inflammasome. In a typical embodiment, the antibody specifically binds to ASC or an antigen or epitope derived therefrom. However, an antibody against any other component of a mammalian inflammasome (e.g., the NALP1, NALP2, NALP3, NLRC4 or AIM2 inflammasome) may be used.

An antibody as described herein can be a monoclonal or polyclonal antibody or active fragments thereof. Said antibodies or active fragments can be chimeric, human or humanized as described herein.

Any suitable antibody or an active fragment thereof as provided herein that specifically binds ASC can be used, e.g., an antibody that inhibits ASC activity in the CNS (e.g., CNS cells) or lung cells (e.g., Type II alveolar cells) of the subject. In one embodiment, the antibody specifically binds to an amino acid sequence having at least 85% sequence identity with amino acid sequence SEQ ID NO:1 or SEQ ID NO:2. In another embodiment, the antibody or fragment thereof binds to an amino acid sequence having at least 85%, 86%, 87%, 88%, 89%, 90%, 91%, 92%, 93%, 94%, 95%, 96%, 97%, 98%, 99% or 100% sequence identity with amino acid sequence KKFKLKLLSVPLREGYGRIPR (SEQ ID NO: 5). In yet another embodiment, the antibody or fragment thereof binds to an amino acid sequence KKFKLKLLSVPLREGYGRIPR (SEQ ID NO: 5) or 2, 3, 4, 5, 6, 7, 8, 9, 10, 11, 12, 13, 14, 15, 16, 17, 18, 19 or 20 amino acids of SEQ ID NO: 5. In a still further embodiment, the antibody or fragment thereof binds to 2-5, 5-10, 10-15 or 15-20 amino acids of SEQ ID NO: 5. In some embodiments, an epitope of ASC (e.g., epitope with amino acid SEQ ID NO: 5) bound by an antibody or antibody fragment is continuous. In some embodiments, an epitope of ASC (e.g., epitope with amino acid SEQ ID NO: 5) bound by an antibody or antibody fragment is discontinuous. In some cases, the monoclonal antibody or the antibody fragment thereof provided herein inhibits or reduces the activity of ASC.

As used herein, the term "epitope" includes any protein determinant capable of specific binding to an immunoglobulin or an immunoglobulin fragment. Epitopic determinants usually consist of chemically active surface groupings of molecules such as amino acids or sugar side chains and usually have specific three dimensional structural characteristics, as well as specific charge characteristics. The term "epitope" also refers to a unit of structure conventionally bound by an immunoglobulin heavy chain variable (VH) region and a light chain variable (VL) region pair. An epitope may define the minimum binding site for an antibody, and thus represent the target of specificity of an antibody.

Similarly, in another embodiment, the inflammasome is the NALP1 inflammasome, and the at least one component is NALP1 (i.e., NLRP1). In this embodiment, the antibody or an active fragment thereof as provided herein specifically binds to an amino acid sequence having at least 85% sequence identity with amino acid sequence SEQ ID NO: 3 or SEQ ID NO: 4.

In yet another embodiment, the agent is one or more EV uptake inhibitors in combination with one or more antibodies or active fragments thereof as provided herein that bind a component of an inflammasome. The EV uptake inhibitor can be any EV uptake inhibitor as provided herein. The antibody that binds a component of an inflammasome can any antibody that binds any inflammasome component as provided herein. In one embodiment, the agent administered to a subject suffering from CNS or lung inflammation comprises a heparin (e.g., Enoxaparin) in combination with an antibody that binds a component of the AIM2 inflammasome (e.g., ASC).

In one embodiment, the method comprises: providing a therapeutically effective amount of a composition including an antibody or an active fragment thereof as provided herein that specifically binds to at least one component (e.g., ASC) of a mammalian inflammasome (e.g., AIM2 inflammasome); and administering the composition to the mammal suffering from CNS or lung inflammation or a viral infection or MS, wherein administering the composition to the mammal results in a reduction of caspase-1 activation in the CNS or lungs of the mammal. In another embodiment, the method comprises: providing a therapeutically effective amount of a composition including an antibody that specifically binds to at least one component (e.g., ASC) of a mammalian inflammasome (e.g., AIM2 inflammasome); and administering the composition to the mammal suffering from CNS or lung inflammation or MS, wherein administering the composition to the mammal results in a reduction in the levels of one or more inflammasome components (e.g., ASC). In yet another embodiment, the method comprises: providing a therapeutically effective amount of a composition including an antibody that specifically binds to at least one component (e.g., ASC) of a mammalian inflammasome (e.g., AIM2 inflammasome); and administering the composition to the mammal suffering from CNS or lung inflammation or MS, wherein administering the composition to the mammal results in a reduction ALI. The CNS or lung inflammation can be the result of a CNS injury (e.g., SCI or TBI), asthma, chronic obstructive pulmonary disorder (COPD), a neurodegenerative disease, or an autoimmune disease with an inflammatory component. In one embodiment, the lung inflammation is caused by a CNS injury such as TBI or SCI. In another embodiment, the lung inflammation occurs as a result of viral infection, for example infection by a coronavirus or an influenza virus.

In one embodiment, the methods provided herein further entail detecting a level or activity of one or more components of a mammalian inflammasome in a sample from a subject suspected of suffering from CNS or lung inflammation or MS. The method of detecting the level or activity entails measuring the level of at least one inflammasome protein (e.g., ASC or AIM2) in the sample obtained from the subject; determining the presence or absence of an elevated level or activity of said at least one inflammasome protein (e.g., ASC or AIM2). The level or activity of said at least one inflammasome protein can be enhanced relative to the level of said at least one inflammasome protein in a control sample. The level or activity of said at least one inflammasome protein in the protein signature can be enhanced relative to a pre-determined reference value or range of reference values. The at least one inflammasome protein can be nucleotide-binding leucine-rich repeat pyrin domain containing protein 1 (NLRP1), NLRP2, NLRP3, NLRC4, AIM2, apoptosis-associated speck-like protein containing a caspase recruitment domain (ASC), caspase-1, or combinations thereof. The sample can be cerebrospinal fluid (CSF), saliva, blood, serum, plasma, urine or a lung aspirate.

Antibodies that Bind Specifically to at Least One Component of a Mammalian Inflammasome The methods described herein for reducing inflammation in the CNS and/or lungs of a mammal include compositions including an antibody or an active fragment thereof as provided herein that specifically binds to at least one component (e.g., ASC, AIM2) of a mammalian inflammasome (e.g., the AIM2 inflammasome). A composition for treating and/or reducing inflammation in the CNS and/or lungs of a mammal can further include at least one pharmaceutically acceptable carrier or diluent. Exemplary antibodies directed against components of a mammalian inflammasome for use in the methods herein can be those found in U.S. Pat. No. 8,685,400, the contents of which are herein incorporated by reference in its entirety. Exemplary monoclonal antibodies or antibody fragments are also provided herein, such as, for example, the monoclonal antibody or antibody fragment comprising a VH region such that the VH region amino acid sequence comprises HCDR1 of SEQ ID NO: 6, HCDR2 of SEQ ID NO: 7 and HCDR3 of SEQ ID NO: 8, and a VL region such that the VL region amino acid sequence comprises LCDR1 of SEQ ID NO: 12, LCDR2 of SEQ ID NO: 13 and LCDR3 of SEQ ID NO: 14.

In one embodiment, a composition for treating and/or reducing inflammation in the CNS or lungs of a mammal includes an antibody or an active fragment thereof as provided herein that specifically binds to a domain or portion thereof of a mammalian ASC protein such as, for example, a human, mouse or rat ASC protein. Any suitable anti-ASC antibody can be used, and several are commercially available. Examples of anti-ASC antibodies for use in the methods herein can be those found in U.S. Pat. No. 8,685,400, the contents of which are herein incorporated by reference in its entirety. Examples of commercially available anti-ASC antibodies for use in the methods provided herein include, but are not limited to 04-147 Anti-ASC, clone 2EI-7 mouse monoclonal antibody from MilliporeSigma, AB3607—Anti-ASC Antibody from Millipore Sigma, orb194021 Anti-ASC from Biorbyt, LS-C331318-50 Anti-ASC from LifeSpan Biosciences, AF3805 Anti-ASC from R & D Systems, NBP1-78977 Anti-ASC from Novus Biologicals, 600-401-Y67 Anti-ASC from Rockland Immunochemicals, D086-3 Anti-ASC from MBL International, AL177 anti-ASC from Adipogen, monoclonal anti-ASC (clone o93E9) antibody, anti-ASC antibody (F-9) from Santa Cruz Biotechnology, anti-ASC antibody (B-3) from Santa Cruz Biotechnology, ASC polyclonal antibody—ADI-905-173 from Enzo Life Sciences, or A161 Anti-Human ASC—Leinco Technologies. The human ASC protein can be accession number NP_037390.2 (Q9ULZ3-1), NP_660183 (Q9ULZ3-2) or Q9ULZ3-3. The rat ASC protein can be accession number NP_758825 (BAC43754). The mouse ASC protein can be accession number NP_075747.3. In one embodiment, the antibody binds to a PYRIN-PAAD-DAPIN domain (PYD) or a portion or fragment thereof of a mammalian ASC protein (e.g. human, mouse or rat ASC). In this embodiment, an antibody as described herein specifically binds to an amino acid sequence having at least 65% (e.g., 65, 70, 75, 80, 85%) sequence identity with a PYD domain or fragment thereof of human, mouse or rat ASC. In one embodiment, the antibody binds to a C-terminal caspase-recruitment domain (CARD) or a portion or fragment thereof of a mammalian ASC protein (e.g. human, mouse or rat ASC). In this embodiment, an antibody as described herein specifically binds to an amino acid sequence having at least 65% (e.g., 65, 70, 75, 80, 85%) sequence identity with a CARD domain or fragment thereof of human, mouse or rat ASC. In still another embodiment, the antibody binds to a portion or fragment thereof of a mammalian ASC protein sequence (e.g. human, mouse or rat ASC) located between the PYD and CARD domains. In another embodiment, a composition for treating and/or reducing inflammation in the CNS and/or lungs of a mammal includes an antibody that specifically binds to a region of rat ASC, e.g., amino acid sequence ALRQTQPYLVTDLEQS (SEQ ID NO:1) (i.e., residues 178-193 of rat ASC, accession number BAC43754). In this embodiment, an antibody as described herein specifically binds to an amino acid sequence having at least 65% (e.g., 65, 70, 75, 80, 85%) sequence identity with amino acid sequence ALRQTQPYLVTDLEQS (SEQ ID NO:1) of rat ASC. In another embodiment, a composition for treating and/or reducing inflammation in the CNS and/or lungs of a mammal includes an antibody that specifically binds to a region of human ASC, e.g., amino acid sequence RESQSYLVEDLERS (SEQ ID NO:2). In still another embodiment, a composition for treating and/or reducing inflammation in the CNS and/or lungs of a mammal includes an antibody that specifically binds to a region of human ASC, e.g., amino acid sequence KKFKLKLLSVPLR-EGYGRIPR (SEQ ID NO: 5; i.e., residues 21-41 of human ASC) or 5-10, 10-15 or 15-20 amino acids of SEQ ID NO: 5. In one embodiment, an antibody that binds to an ASC domain or fragment thereof as described herein inhibits ASC activity in lung cells, e.g., Type II alveolar cells of a mammal. In another embodiment, an antibody that binds to an ASC domain or fragment thereof as described herein (e.g., monoclonal anti-ASC antibody or antibody fragments thereof provided herein) inhibits ASC activity in the CNS of a mammal suffering or suspected of suffering from a CNS injury or disorder. Examples of CNS injuries or disorders can include TBI, SCI, stroke, amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD).

In certain embodiments, the invention provides antibodies and antibody fragments that bind specifically to ASC and that comprise one or more amino acid sequences shown Table 2. Also provided herein are isolated nucleic acid molecules encoding the monoclonal antibodies or the antibody fragments thereof that comprise nucleic acid sequences shown in Table 2. In some cases, expression vectors comprising the nucleic acid molecules of Table 2. The expression vector can comprise heavy chain or light chain constant regions. An example of a light chain and heavy chain expression vector system for use in the compositions and methods provided herein is the Antitope pANT expression vector system for IgG4 (S241P) heavy and kappa light chain. The nucleic acid molecule for the heavy or light chain can be operatively linked to regulatory sequences suitable for expression of the nucleic acid segments in a host cell.

TABLE 2

Variable Heavy and Variable Light (Kappa) Chain Sequences of anti-ASC antibody or antibody fragments thereof of the invention.

Heavy Chain (H) CDR1 Amino Acid Sequence
TSGMGVS (SEQ ID NO: 6)

Heavy Chain (H) CDR1 Nucleic Acid Sequence
ACTAGTGGAATGGGTGTGAGC (SEQ ID NO: 9)

Heavy Chain (H) CDR2 Amino Acid Sequence
HIYWDDDKRYNPSLKS (SEQ ID NO: 7)

Heavy Chain (H) CDR2 Nucleic Acid Sequence
CACATTTATTGGGATGATGATAAGCGCTACAACCCATCTCTGAAGAGC (SEQ ID NO: 10)

Heavy Chain (H) CDR3 Amino Acid Sequence
STPIVANAMDY (SEQ ID NO: 8)

Heavy Chain (H) CDR3 Nucleic Acid Sequence
AGCACCCCCATCGTGGCCAACGCCATGGACTAC (SEQ ID NO: 11)

Light (Kappa) (L) Chain CDR1 Amino Acid Sequence
KASQSVDYDGDSYMN (SEQ ID NO: 12)

Light (Kappa) (L) Chain CDR1 Nucleic Acid Sequence
AAGGCCAGCCAGAGTGTTGACTACGACGGCGACAGTTACATGAAT (SEQ ID NO: 15)

Light (Kappa) (L) Chain CDR2 Amino Acid Sequence
AASNLES (SEQ ID NO: 13)

Light (Kappa) (L) Chain CDR2 Nucleic Acid Sequence
GCCGCATCTAACCTGGAATCC (SEQ ID NO: 16)

Light (Kappa) (L) Chain CDR3 Amino Acid Sequence
QQSNEDPYT (SEQ ID NO: 14)

Light (Kappa) (L) Chain CDR3 Nucleic Acid Sequence
CAGCAATCTAATGAGGACCCTTACACT (SEQ ID NO: 17)

Variable Heavy (VH) 1 Chain Amino Acid Sequence
QVTLKESGPAIVKPTQTLTLTCSFSGFSLSTSGMGVSWIRQPSGKGLEWLAHIYWDDD
KRYNPSLKSRLTISKDSSKNQVVLKITSVDPVDTATYSCARSTPIVANAMDYWGQGTS
VTVSS (SEQ ID NO: 18)

Variable Heavy (VH) 1 Chain Nucleic Acid Sequence
CAGGTCACCTTGAAGGAGTCTGGTCCTGCCATCGTGAAACCCACACAGACCCTCA
CGCTGACCTGCAGCTTCTCTGGGTTCTCACTCAGCACTAGTGGAATGGGTGTGAGC
TGGATCCGTCAGCCCTCAGGAAAGGGCCTGGAGTGGCTTGCACACATTTATTGGG
ATGATGATAAGCGCTACAACCCATCTCTGAAGAGCAGGCTCACCATCTCCAAGGA
CAGCTCCAAAAACCAGGTGGTCCTTAAAATCACCAGCGTGGACCCTGTGGACACA
GCCACATATTCCTGTGCACGGAGCACCCCCATCGTGGCCAACGCCATGGACTACT
GGGGCCAAGGAACCAGCGTCACCGTCTCCTCA (SEQ ID NO: 23)

Variable Heavy (VH) 2 Chain Amino Acid Sequence
QVTLKESGPALVKPTQTLTLTCSFSGFSLSTSGMGVSWIRQPAGKGLEWLAHIYWDD
DKRYNPSLKSRLTISKDSSKNQVVLTMTNMDPVDTATYSCARSTPIVANAMDYWGQ
GTLVTVSS (SEQ ID NO: 19)

Variable Heavy (VH) 2 Chain Nucleic Acid Sequence
CAGGTCACCTTGAAGGAGTCTGGTCCTGCCCTGGTGAAACCCACACAGACCCTCA
CGCTGACCTGCAGCTTCTCTGGGTTCTCACTCAGCACTAGTGGAATGGGTGTGAGC
TGGATCCGTCAGCCCGCCGGAAAGGGCCTGGAGTGGCTTGCACACATTTATTGGG
ATGATGATAAGCGCTACAACCCATCTCTGAAGAGCAGGCTCACCATCTCCAAGGA TABLE 2-continued Variable Heavy and Variable Light (Kappa) Chain
Sequences of anti-ASC antibody or antibody
fragments thereof of the invention.

```
CAGCTCCAAAAACCAGGTGGTCCTTACAATGACCAACATGGACCCTGTGGACACA
GCCACATATTCCTGTGCACGGAGCACCCCCATCGTGGCCAACGCCATGGACTACT
GGGGCCAAGGAACCCTGGTCACCGTCTCCTCA (SEQ ID NO: 24)
```

Variable Heavy (VH) 3 Chain Amino Acid Sequence
QVTLKESGPALVKPTQTLTLTCSFSGFSLSTSGMGVSWIRQPAGKGLEWLAHIYWDD
DKRYNPSLKSRLTISKDSSKNQVVLTMTNMDPVDTATYYCARSTPIVANAMDYWGQ
GTLVTVSS (SEQ ID NO: 20)

Variable Heavy (VH) 3 Chain Nucleic Acid Sequence
```
CAGGTCACCTTGAAGGAGTCTGGTCCTGCCCTGGTGAAACCCACACAGACCCTCA
CGCTGACCTGCAGCTTCTCTGGGTTCTCACTCAGCACTAGTGGAATGGGTGTGAGC
TGGATCCGTCAGCCCGCCGGAAAGGGCCTGGAGTGGCTTGCACACATTTATTGGG
ATGATGATAAGCGCTACAACCCATCTCTGAAGAGCAGGCTCACCATCTCCAAGGA
CAGCTCCAAAAACCAGGTGGTCCTTACAATGACCAACATGGACCCTGTGGACACA
GCCACATATTACTGTGCACGGAGCACCCCCATCGTGGCCAACGCCATGGACTACT
GGGGCCAAGGAACCCTGGTCACCGTCTCCTCA (SEQ ID NO: 25)
```

Variable Heavy (VH) 4 Chain Amino Acid Sequence
QVTLKESGPALVKPTQTLTLTCTFSGFSLSTSGMGVSWIRQPAGKGLEWLAHIYWDD
DKRYNPSLKSRLTISKDTSKNQVVLTMTNMDPVDTATYYCARSTPIVANAMDYWGQ
GTLVTVSS (SEQ ID NO: 21)

Variable Heavy (VH) 4 Chain Nucleic Acid Sequence
```
CAGGTCACCTTGAAGGAGTCTGGTCCTGCCCTGGTGAAACCCACACAGACCCTCA
CGCTGACCTGCACCTTCTCTGGGTTCTCACTCAGCACTAGTGGAATGGGTGTGAGC
TGGATCCGTCAGCCCGCCGGAAAGGGCCTGGAGTGGCTTGCACACATTTATTGGG
ATGATGATAAGCGCTACAACCCATCTCTGAAGAGCAGGCTCACCATCTCCAAGGA
CACCTCCAAAAACCAGGTGGTCCTTACAATGACCAACATGGACCCTGTGGACACA
GCCACATATTACTGTGCACGGAGCACCCCCATCGTGGCCAACGCCATGGACTACT
GGGGCCAAGGAACCCTGGTCACCGTCTCCTCA (SEQ ID NO: 26)
```

Variable Heavy (VH) Chimeric (O) Chain Amino Acid Sequence
QVTLKESGPGILQPSQTLSLTCSFSGFSLSTSGMGVSWIRQPSGKGLEWLAHIYWDDD
KRYNPSLKSRLTISKDSSSNQVFLKITSVDTADTATYSCARSTPIVANAMDYWGQGTS
VTVSS (SEQ ID NO: 22)

Variable Heavy (VH) Chimeric (O) Chain Nucleic Acid
Sequence
```
CAGGTTACTCTGAAAGAGTCTGGCCCTGGGATATTGCAGCCCTCCCAGACCCTCA
GTCTGACTTGTTCTTTCTCTGGGTTTTCACTGAGCACTTCTGGTATGGGTGTGAGCT
GGATTCGTCAGCCTTCAGGAAAGGGTCTGGAGTGGCTGGCACACATTTACTGGGA
TGATGACAAGCGCTATAACCCATCCCTGAAGAGCCGGCTCACAATCTCCAAGGAT
TCCTCCAGCAACCAGGTCTTCCTCAAGATCACCAGTGTGGACACTGCAGATACTGC
CACATACTCCTGTGCTCGAAGTACTCCGATTGTAGCTAATGCTATGGACTACTGGG
GTCAAGGAACCTCAGTCACCGTCTCCTCA (SEQ ID NO: 27)
```

Variable Kappa Light (VL) 1 Chain Amino Acid Sequence
DIVLTQSPDSLAVSLGERATINCKASQSVDYDGDSYMNWYQQKPGQPPKLLIYAASN
LESGIPARFSGSGSGTDFTLTISSLQEEDVATYYCQQSNEDPYTFGQGTKLEIK
(SEQ ID NO: 28)

Variable Kappa Light (VL) 1 Chain Nucleic Acid Sequence
```
GACATCGTGCTGACCCAGTCTCCAGACTCCCTGGCTGTGTCTCTGGGCGAGAGGG
CCACCATCAACTGCAAGGCCAGCCAGAGTGTTGACTACGACGGCGACAGTTACAT
GAATTGGTACCAGCAGAAACCAGGACAGCCTCCTAAGCTGCTCATTTACGCCGCA
TCTAACCTGGAATCCGGCATCCCTGCCCGATTCAGTGGCAGCGGGTCTGGGACAG
ATTTCACTCTCACCATCAGCAGCCTGCAGGAGGAAGATGTGGCAACTTATTACTGT
CAGCAATCTAATGAGGACCCTTACACTTTTGGCCAGGGGACCAAGCTGGAGATCA
AA (SEQ ID NO: 32)
```

Variable Kappa Light (VL) 2 Chain Amino Acid Sequence
DIVLTQSPDSLAVSLGERATINCKASQSVDYDGDSYMNWYQQKPGQPPKLLIYAASN
LESGIPARFSGSGSGTDFTLTISSLQPEDVATYYCQQSNEDPYTFGQGTKLEIK
(SEQ ID NO: 29)

Variable Kappa Light (VL) 2 Chain Nucleic Acid Sequence
```
GACATCGTGCTGACCCAGTCTCCAGACTCCCTGGCTGTGTCTCTGGGCGAGAGGG
CCACCATCAACTGCAAGGCCAGCCAGAGTGTTGACTACGACGGCGACAGTTACAT
GAATTGGTACCAGCAGAAACCAGGACAGCCTCCTAAGCTGCTCATTTACGCCGCA
TCTAACCTGGAATCCGGCATCCCTGCCCGATTCAGTGGCAGCGGGTCTGGGACAG
ATTTCACTCTCACCATCAGCAGCCTGCAGCCTGAAGATGTGGCAACTTATTACTGT
CAGCAATCTAATGAGGACCCTTACACTTTTGGCCAGGGGACCAAGCTGGAGATCA
AA (SEQ ID NO: 33)
```

TABLE 2-continued

Variable Heavy and Variable Light (Kappa) Chain
Sequences of anti-ASC antibody or antibody
fragments thereof of the invention.

Variable Kappa Light (VL) 3 Chain Amino Acid Sequence
DIVMTQSPDSLAVSLGERATINCKAS QSVDYDGDSYMNWYQQKPGQPPKLLIYAASN
LESGIPARFSGSGSGTDFTLTISSLQPEDVATYYCQQSNEDPYTFGQGTKLEIK
(SEQ ID NO: 30)

Variable Kappa Light (VL) 3 Chain Nucleic Acid Sequence
GACATCGTGATGACCCAGTCTCCAGACTCCCTGGCTGTGTCTCTGGGCGAGAGGG
CCACCATCAACTGCAAGGCCAGCCAGAGTGTTGACTACGACGGCGACAGTTACAT
GAATTGGTACCAGCAGAAACCAGGACAGCCTCCTAAGCTGCTCATTTACGCCGCA
TCTAACCTGGAATCCGGCATCCCTGCCCGATTCAGTGGCAGCGGGTCTGGGACAG
ATTTCACTCTCACCATCAGCAGCCTGCAGCCTGAAGATGTGGCAACTTATTACTGT
CAGCAATCTAATGAGGACCCTTACACTTTTGGCCAGGGGACCAAGCTGGAGATCA
AA (SEQ ID NO: 34)

Variable Kappa Light (VL) Chimeric (O) Chain Amino Acid
Sequence
DIVLTQSPASLAVSLGQRATISCKASQSVDYDGDSYMNWYQQKPGQPPKLLIYAASN
LESGIPARFSGSGSGTDFTLNIHPVEEEDAATYYCQQSNEDPYTFGGGTKLEIK
(SEQ ID NO: 31)

Variable Kappa Light (VL) Chimeric (O) Chain Nucleic Acid
Sequence
GACATTGTGCTGACCCAATCTCCAGCTTCTTTGGCTGTGTCTCTAGGGCAGAGGGC
CACCATCTCCTGCAAGGCCAGCCAAAGTGTTGATTATGATGGTGATAGTTATATGA
ACTGGTACCAACAGAAACCAGGACAGCCACCCAAACTCCTCATCTATGCTGCATC
CAATCTAGAATCTGGCATCCCAGCCAGGTTTAGTGGCAGTGGGTCTGGGACAGAC
TTCACCCTCAACATCCATCCTGTGGAGGAGGAGGATGCTGCAACCTATTACTGTCA
GCAAAGTAATGAGGAcCCGTACACGTTCGGAGGGGGGACCAAGCTGGAAATAAA
A (SEO ID NO: 35)

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 18, 19, 20, 21, 22, or an amino acid sequence that is at least 95%, 96%, 97%, 98% or 99% identical to the amino acid sequence of SEQ ID NO: 18, 19, 20, 21, or 22. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VL region amino acid sequence comprises SEQ ID NO: 28, 29, 30, 31, or an amino acid sequence that is at least 95%, 96%, 97%, 98% or 99% identical to the amino acid sequence of SEQ ID NO: 28, 29, 30 or 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 18, 19, 20, 21, 22, or an amino acid sequence that is at least 95%, 96%, 97%, 98% or 99% identical to the amino acid sequence of SEQ ID NO: 18, 19, 20, 21 or 22; and wherein the VL region amino acid sequence comprises SEQ ID NO: 28, 29, 30, 31, or an amino acid sequence that is at least 95%, 96%, 97%, 98% or 99% identical to the amino acid sequence of SEQ ID NO: 28, 29, 30 or 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 28 or an amino acid sequence that is at least 95%, 96%, 97%, 98% or 99% identical to the amino acid sequence of SEQ ID NO: 28. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 29 or an amino acid sequence that is at least 95%, 96%, 97%, 98% or 99% identical to the amino acid sequence of SEQ ID NO: 29. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 30 or an amino acid sequence that is at least 95%, 96%, 97%, 98% or 99% identical to the amino acid sequence of SEQ ID NO: 30. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 31 or an amino acid sequence that is at least 95%, 96%, 97%, 98% or 99% identical to the amino acid sequence of SEQ ID NO: 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 28 or an amino acid sequence that is at least 95%, 96%, 97%, 98% or 99% identical to the amino acid sequence of SEQ ID NO: 28. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 29 or an amino acid sequence that is at least 95%, 96%, 97%, 98% or 99% identical to the amino acid sequence of SEQ ID NO: 29. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 30 or an amino acid sequence that is at least 95%, 96%, 97%, 98% or 99% identical to the amino acid sequence of SEQ ID NO: 30. In some cases, a monoclonal antibody or an antibody fragment derived therefrom comprising a VH region amino acid sequence comprising SEQ ID NO: 19 and a VL region amino acid sequence comprising SEQ ID NO: 30 can be referred to as IC-100. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 31 or an amino acid sequence that is at least 95%, 96%, 97%, 98% or 99% identical to the amino acid sequence of SEQ ID NO: 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 28 or an amino acid sequence that is at least 95%, 96%, 97%, 98% or 99% identical to the amino acid sequence of SEQ ID NO: 28. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 29 or an amino acid sequence that is at least 95%, 96%, 97%, 98% or 99% identical to the amino acid sequence of SEQ ID NO: 29. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 30 or an amino acid sequence that is at least 95%, 96%, 97%, 98% or 99% identical to the amino acid sequence of SEQ ID NO: 30. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 31 or an amino acid sequence that is at least 95%, 96%, 97%, 98% or 99% identical to the amino acid sequence of SEQ ID NO: 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 28 or an amino acid sequence that is at least 95%, 96%, 97%, 98% or 99% identical to the amino acid sequence of SEQ ID NO: 28. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 29 or an amino acid sequence that is at least 95%, 96%, 97%, 98% or 99% identical to the amino acid sequence of SEQ ID NO: 29. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 30 or an amino acid sequence that is at least 95%, 96%, 97%, 98% or 99% identical to the amino acid sequence of SEQ ID NO: 30. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 31 or an amino acid sequence that is at least 95%, 96%, 97%, 98% or 99% identical to the amino acid sequence of SEQ ID NO: 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 28 or an amino acid sequence that is at least 95%, 96%, 97%, 98% or 99% identical to the amino acid sequence of SEQ ID NO: 28. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 29 or an amino acid sequence that is at least 95%, 96%, 97%, 98% or 99% identical to the amino acid sequence of SEQ ID NO: 29. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 30 or an amino acid sequence that is at least 95%, 96%, 97%, 98% or 99% identical to the amino acid sequence of SEQ ID NO: 30. Further to this embodiment, provided herein is use of the monoclonal antibody or antibody fragment thereof in a method for treating inflammation in a subject. The inflammation can be an innate immune inflammation. The inflammation can be an inflammasome-related inflammation. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In one embodiment, provided herein is a monoclonal antibody or an antibody fragment thereof that binds specifically ASC, wherein the antibody or the antibody fragment thereof comprises a heavy chain variable (VH) region and a light or kappa chain variable (VL) region, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 31 or an amino acid sequence that is at least 95%, 96%, 97%, 98% or 99% identical to the amino acid sequence of SEQ ID NO: 31. Further to this embodiment, provided herein is use of the monoclonal antibody or antibody fragment thereof in a method for treating inflammation in a subject. The inflammation can be an innate immune inflammation. The inflammation can be an inflammasome-related inflammation. In one embodiment, the monoclonal antibodies or antibody fragments thereof provided herein can be used in a method for reducing inflammation in a mammal as described in U.S. Pat. No. 8,685,400, the contents of which are herein incorporated by reference in their entirety. The inflammation can be in the lungs and/or the CNS. The inflammation in the lungs and/or the CNS can be the result of a viral infection, an injury (e.g., traumatic brain injury (TBI) or spinal cord injury (SCI)) or disease, condition or affliction of the CNS or affecting the CNS. As provided herein, the disease, condition or affliction of the CNS or affecting the CNS can be stroke as well as autoimmune diseases and/or CNS diseases including amyotrophic lateral sclerosis (ALS) Lou Gehrig's, multiple sclerosis (MS), immune dysfunction muscular CNS breakdown, muscular dystrophy (MD), Alzheimer's disease (AD), Parkinson's disease (PD). Use of the monoclonal antibody or antibody fragment thereof in a method for treating inflammation can reduce inflammation in the CNS and/or lungs of the patient. The reduction can be as compared to a control (e.g., untreated patient and/or patient prior to treatment). In one embodiment, the monoclonal antibody or antibody fragment derived therefrom is used to treat MS by administering the monoclonal antibody or antibody fragment derived therefrom to a patient suffering from or suspected of suffering from MS. In some cases, the monoclonal antibody or the antibody fragment thereof of this embodiment is present in a composition. The composition can be a pharmaceutical composition as provided herein.

In another embodiment, a composition for reducing inflammation in the CNS or lungs of a mammal includes an antibody or an active fragment thereof as provided herein that specifically binds to NLRP1 (e.g., anti-NLRP1 chicken antibody) or a domain thereof. Any suitable anti-NLRP1 antibody can be used, and several are commercially available. Examples of anti-NLRP1 antibodies for use in the methods herein can be those found in U.S. Pat. No. 8,685, 400, the contents of which are herein incorporated by reference in its entirety. Examples of commercially available anti-NLRP1 antibodies for use in the methods provided herein include, but are not limited to human NLRP1 polyclonal antibody AF6788 from R&D Systems, EMD Millipore rabbit polyclonal anti-NLRP1 ABF22, Novus Biologicals rabbit polyclonal anti-NLRP1 NB100-56148, Sigma-Aldrich mouse polyclonal anti-NLRP1 SAB1407151, Abcam rabbit polyclonal anti-NLRP1 ab3683, Biorbyt rabbit polyclonal anti-NLRP1 orb325922 mybiosource rabbit polyclonal anti-NLRP1 MBS7001225, R&D systems sheep polyclonal AF6788, Aviva Systems mouse monoclonal anti-NLRP1 oaed00344, Aviva Systems rabbit polyclonal anti-NLRP1 ARO54478_P050, Origene rabbit polyclonal anti-NLRP1 APO7775PU-N, Antibodies online rabbit polyclonal anti-NLRP1 ABIN768983, Prosci rabbit polyclonal anti-NLRP1 3037, Proteintech rabbit polyclonal anti-NLRP1 12256-1-AP, Enzo mouse monoclonal anti-NLRP1 ALX-804-803-C100, Invitrogen mouse monoclonal anti-NLRP1 MA1-25842, GeneTex mouse monoclonal anti-NLRP1 GTX16091, Rockland rabbit polyclonal anti-NLRP1 200-401-CX5, or Cell Signaling Technology rabbit polyclonal anti-NLRP1 4990. The human NLRP1 protein can be accession number AAH51787, NP_001028225, NP_055737, NP_127497, NP_127499, or NP_127500. In one embodiment, the antibody binds to a Pyrin, NACHT, LRR1-6, FUND or CARD domain or a portion or fragment thereof of a mammalian NLRP1 protein (e.g. human NLRP1). In this embodiment, an antibody as described herein specifically binds to an amino acid sequence having at least 65% (e.g., 65, 70, 75, 80, 85%) sequence identity with a specific domain (e.g., Pyrin, NACHT, LRR1-6, FUND or CARD) or fragment thereof of human NLRP1. In one embodiment, a chicken anti-NLRP1 polyclonal that was custom-designed and produced by Ayes Laboratories is used for reducing lung inflammation. This antibody can be directed against the following amino acid sequence in human NLRP1: CEYYTEIREREREKSEKGR (SEQ ID NO: 3). In one embodiment, an antibody that binds to a NLRP1 domain or fragment thereof as described herein inhibits NLRP1 activity in lung cells, e.g., Type II alveolar cells of a mammal.

In yet another embodiment, a composition for reducing inflammation in the CNS or lungs of a mammal includes an antibody or an active fragment thereof as provided herein that specifically binds to AIM2 or a domain thereof. Any suitable anti-AIM2 antibody can be used, and several are commercially available. Examples of commercially available anti-AIM2 antibodies for use in the methods provided herein include, but are not limited to a rabbit polyclonal anti-AIM2 cat. Number 20590-1-AP from Proteintech, Abcam anti-AIMS antibody (ab119791), rabbit polyclonal anti-AIM2 (N-terminal region) Cat. Number AP3851 from ECM biosciences, rabbit polyclonal anti-ASC Cat. Number E-AB-30449 from Elabsciences, Anti-AIM2 mouse monoclonal antibody called AIM2 Antibody (3C4G11) with catalog number sc-293174 from Santa Cruz Biotechnology, mouse monoclonal AIM2 antibody with catalog number TA324972 from Origene, AIM2 monoclonal antibody (10M2B3) from Thermofisher Scientific, AIM2 rabbit polyclonal antibody ABIN928372 or ABIN760766 from Antibodies-online, Biomatix coat anti-AIM2 polyclonal antibody with cat. Number CAE02153. Anti-AIM2 polyclaonl antibody (OABF01632) from Aviva Systems Biology, rabbit polyclonal anti-AIM2 antibody LS-C354127 from LSBio-C354127, rabbit monoclonal anti-AIM2 antibody from Cell Signaling Technology, with cat number MA5-16259. Rabbit polyclonal anti-AIM2 monoclonal antibody from Fab Gennix International Incorporated, Cat. Number AIM2 201AP, MyBiosource rabbit polyclonal anti-AIM2 cat number MBS855320, Signalway rabbit polyclonal anti AIM2 cateaog number 36253, Novus Biological rabbit polyclonal anti-AIM2 catalog number 43900002, GeneTex rabbit polclonal anti-AIM2 GTX54910, Prosci, rabbit polyclonal anti-AIM2 26-540, Biorbyt mouse monoclonal anti-AIM2 orb333902, Abcam rabbit polyclonal anti-AIM2 ab93015), Abcam rabbit polyclonal anti-AIM2 ab76423, Signma Aldrich mouse polyclonal anti-AIM2 SAB1406827, or Biolegend anti-AIM2 3B10. The human AIM2 protein can be accession number NX_014862, NP004824, XP016858337, XP005245673, AAB81613, BAF84731 or AAH10940. In one embodiment, the antibody binds to a Pyrin or HIN-200 domain or a portion or fragment thereof of a mammalian AIM2 protein (e.g. human AIM2). In this embodiment, an antibody as described herein specifically binds to an amino acid sequence having at least 65% (e.g., 65, 70, 75, 80, 85%) sequence identity with a specific domain (e.g., Pyrin or HIN-200) or fragment thereof of human AIM2. In one embodiment, an antibody that binds to a AIM2 domain or fragment thereof as described herein inhibits AIM2 activity in lung cells, e.g., Type II alveolar cells of a mammal.

Anti-inflammasome (e.g., Anti-ASC, anti-NLRP1 or anti-AIM2) antibodies as described herein include polyclonal and monoclonal rodent antibodies, polyclonal and monoclonal human antibodies, or any portions thereof, having at least one antigen binding region of an immunoglobulin variable region, which antibody specifically binds to a component of a mammalian inflammasome (e.g., AIM2 inflammasome) such as, for example, ASC or AIM2. In some cases, the antibody is specific for ASC such that an antibody is specific for ASC if it is produced against an epitope of the polypeptide and binds to at least part of the natural or recombinant protein.

In certain embodiments, an antibody provided herein comprises a polypeptide having one or more amino acid substitutions, deletions or insertions. For example, an anti-ASC monoclonal antibody or an ASC binding antibody fragment comprises a polypeptide having one or more amino acid substitutions, deletions or insertions as compared to a polypeptide having an amino acid sequence of one or more of SEQ ID NOs: 6-8, 12-14, 18-22 or 28-31. An antibody provided herein may have 1, 2, 3, 4, 5, 6, 7, 8, 9, 10, or more amino acid substitutions, deletions or insertions. For example, an anti-ASC monoclonal antibody or an ASC binding antibody fragment may have 1, 2, 3, 4, 5, 6, 7, 8, 9, 10, or more amino acid substitutions, deletions or insertions. Substitutions, deletions or insertions may be introduced by standard techniques, such as site-directed mutagenesis or PCR-mediated mutagenesis of a nucleic acid molecule encoding a polypeptide of an anti-ASC antibody or an ASC-binding antibody fragment.

In certain embodiments, conservative amino acid substitutions are made at one or more positions in the amino acid sequences of antibodies or antibody fragments disclosed herein. A "conservative amino acid substitution" is one in which the amino acid residue is replaced with an amino acid residue having a similar side chain. In certain embodiments, conservative amino acid substitutions are made only in the FR sequences and not in the CDR sequences of an antibody or antibody fragment. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan; histidine). Thus, for example, an amino acid residue in a polypeptide of an anti-ASC monoclonal antibody or an ASC binding antibody fragment may be replaced with another amino acid residue from the same side chain family. In certain embodiments, a string of amino acids can be replaced with a structurally similar string that differs in order and/or composition of side chain family members. Those skilled in the art will be able to evaluate whether an anti-ASC monoclonal antibody or an ASC binding antibody fragment comprising a polypeptide having one or more amino acid substitutions, deletions or insertions as compared to a polypeptide having an amino acid sequence of one or more of SEQ ID NOs: 6-8, 12-14, 18-22 or 28-31 binds ASC protein by utilizing routine, art-recognized methods including, but not limited to, ELISAs, Western blots, phage display, etc.

Calculations of sequence homology or identity (the terms are used interchangeably herein) between sequences may be performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In an exemplary embodiment, the length of a reference sequence aligned for comparison purposes is at least 30%, 40%, 50%, 60%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In one embodiment, the percent identity between two amino acid sequences is determined using the Needleman et al. ((1970) J. Mol. Biol. 48:444-453) algorithm which has been incorporated into the GAP program in the GCG software package (available at www.gcg.com), using either a BLOSUM 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (available at www.gcg.com), using a NWSgapdna.CMP matrix and a gap weight of 40, 50, 60, 70, or 80 and a length weight of 1, 2, 3, 4, 5, or 6. One set of parameters (and the one that can be used if the practitioner is uncertain about what parameters should be applied to determine if a molecule is within a sequence identity or homology limitation of the invention) is a BLOSUM 62 scoring matrix with a gap penalty of 12, a gap extend penalty of 4, and a frameshift gap penalty of 5.

The percent identity between two amino acid or nucleotide sequences can be determined using the algorithm of Meyers et al. ((1989) CABIOS 4:11-17) which has been incorporated into the ALIGN program (version 2.0), using a PAM120 weight residue table, a gap length penalty of 12 and a gap penalty of 4.

In certain aspects, an antibody is a monoclonal antibody. In other aspects, an antibody is a polyclonal antibody. The term "monoclonal antibody" refers to a population of antibody molecules that contain only one species of an antigen binding site capable of immunoreacting with a particular epitope of an antigen. A monoclonal antibody composition thus typically displays a single binding affinity for a particular protein with which it immunoreacts.

In some aspects, an antibody of the invention (an anti-ASC monoclonal antibody or an ASC binding antibody fragment) is humanized, chimeric or human.

In some embodiments, an antibody of the invention is a humanized antibody.

"Humanized antibody" as the term is used herein refers to an antibody that has been engineered to comprise one or more human framework regions in the variable region together with non-human (e.g., mouse, rat, or hamster) complementarity-determining regions (CDRs) of the heavy and/or light chain. In certain embodiments, a humanized antibody comprises sequences that are entirely human except for the CDR regions. In some instances, Fv framework region (FR) residues of the human immunoglobulin are replaced by corresponding non-human residues. Furthermore, the humanized antibody may comprise residues that are found neither in the human form of the antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The FR region can be modified in any manner known in the art and/or provided herein. The modifications can confer desirable properties such as increased half-life and/or improved expression in host cells. In one embodiment, the FR region(s) can be modified or mutated as described in US20150232557, which is herein incorporated by reference. Other forms of humanized antibodies can have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody. The humanized antibody optimally also will comprise at least a portion of an immunoglobulin constant region or domain (Fc), typically that of a human immunoglobulin.

Humanized antibodies are typically less immunogenic to humans, relative to non-humanized antibodies, and thus offer therapeutic benefits in certain situations. For example, the antibody constant region can be engineered such that it is immunologically inert (e.g., does not trigger complement lysis). See, e.g. PCT Publication No. PCT/GB99/01441; UK Patent Application No. 9809951.8, each of which is incorporated herein by reference in its entirety. Those skilled in the art will be aware of humanized antibodies, and will also be aware of suitable techniques for their generation. See for example, Hwang, W. Y. K., et al., Methods 36:35, 2005; Queen et al., Proc. Natl. Acad. Sci. USA, 86:10029-10033, 1989; Jones et al., Nature, 321:522-25, 1986; Riechmann et al., Nature, 332:323-27, 1988; Verhoeyen et al., Science, 239:1534-36, 1988; Orlandi et al., Proc. Natl. Acad. Sci. USA, 86:3833-37, 1989; U.S. Pat. Nos. 5,225,539; 5,530, 101; 5,585,089; 5,693,761; 5,693,762; 6,180,370; and Selick et al., WO 90/07861, each of which is incorporated herein by reference in its entirety. Other methods of humanizing antibodies that may also be utilized are disclosed by Daugherty et al., Nucl. Acids Res. 19:2471-2476, 1991, and in U.S. Pat. Nos. 6,180,377; 6,054,297; 5,997,867; 5,866, 692; 6,210,671; and 6,350,861; and in PCT Publication No. WO 01/27160, each of which is incorporated herein by reference in its entirety. For example, an anti-ASC antibody or anti-ASC antigen-binding fragment of the invention may comprise a VH region amino acid sequence that comprises HCDR1 of SEQ ID NO: 6, HCDR2 of SEQ ID NO: 7 and HCDR3 of SEQ ID NO: 8; and a VL region amino acid sequence that comprises LCDR1 of SEQ ID NO: 12, LCDR2 of SEQ ID NO: 13 and LCDR3 of SEQ ID NO: 14; and one or more human framework region sequences.

In some embodiments, an antibody of the invention is a chimeric antibody and binds specifically ASC. In some cases, the anti-ASC chimeric antibody reduces the activity of ASC. "Chimeric antibody" as the term is used herein refers to an antibody that has been engineered to comprise at least one human constant region. For example, one or all the variable regions of the light chain(s) and/or one or all the variable regions of the heavy chain(s) of a mouse antibody (e.g., a mouse monoclonal antibody) may each be joined to a human constant region, such as, without limitation an IgG1 human constant region. Chimeric antibodies are typically less immunogenic to humans, relative to non-chimeric antibodies, and thus offer therapeutic benefits in certain situations. Those skilled in the art will be aware of chimeric antibodies, and will also be aware of suitable techniques for their generation. See, for example, Cabilly et al., U.S. Pat. No. 4,816,567; Shoemaker et al., U.S. Pat. No. 4,978,775; Beavers et al., U.S. Pat. No. 4,975,369; and Boss et al., U.S. Pat. No. 4,816,397, each of which is incorporated herein by reference in its entirety. For example, an antibody or antigen-binding fragment of the invention may comprise a VH region comprising SEQ ID NO: 22; a VL region comprising SEQ ID NO: 31, and a human constant region.

As used herein, the terms "immunological binding," and "immunological binding properties" refer to the non-covalent interactions of the type which occur between an immunoglobulin molecule (e.g., antibody) and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an epitope (e.g., ASC fragment with amino acid SEQ ID NO: 5) when the equilibrium binding constant ($K_d$) is ≤10 μM, ≤10 nM, ≤10 nM, and ≤100 pM to about 1 pM, as measured by assays such as radioligand binding assays or similar assays known to those skilled in the art.

In certain aspects, an antibody of the invention is monovalent or bivalent and comprises a single or double chain. Functionally, the binding affinity of an antibody may be within the range of $10^{-5}$ M to $10^{-12}$ M. For example, the binding affinity of an antibody is from $10^{-6}$ M to $10^{-12}$ M, from $10^{-7}$ M to $10^{-12}$ M, from $10^{-8}$ M to $10^{-12}$ M, from $10^{-9}$ M to $10^{-12}$ M, from $10^{-5}$ M to $10^{-11}$ M, from $10^{-6}$ M to $10^{-11}$ M, from $10^{-7}$ M to $10^{-11}$ M, from $10^{-1}$ M to $10^{-11}$ M, from $10^{-9}$ M to $10^{-11}$ M, from $10^{-10}$ M to $10^{-11}$ M, from $10^{-5}$ M to $10^{-10}$ M, from $10^{-6}$ M to $10^{-10}$ M, from $10^{-7}$ M to $10^{-10}$ M, from $10^{-8}$ M to $10^{-10}$ M, from $10^{-9}$ M to $10^{-10}$ M, from $10^{-5}$ M to $10^{-9}$ M, from $10^{-6}$ M to $10^{-9}$ M, from $10^{-7}$ M to $10^{-9}$ M, from $10^{-8}$ M to $10^{-9}$ M, from $10^{-5}$ M to $10^{-8}$ M, from $10^{-6}$ M to $10^{-8}$ M, from $10^{-7}$ M to $10^{-8}$ M, from $10^{-5}$ M to $10^{-7}$ M, from $10^{-6}$ M to $10^{-7}$ M or from $10^{-5}$ M to $10^{-6}$ M.

Methods for determining monoclonal antibody specificity and affinity by competitive inhibition can be found in Harlow, et al., Antibodies: A Laboratory Manual, Cold Spring Harbor Laboratory Press, Cold Spring Harbor, N.Y., 1988, Colligan et al., eds., Current Protocols in Immunology, Greene Publishing Assoc. and Wiley Interscience, N.Y., (1992, 1993), and Muller, Meth. Enzymol. 92:589-601, 1983, which references are entirely incorporated herein by reference.

Anti-inflammasome (e.g., Anti-ASC and anti-AIM2) antibodies of the present invention can be routinely made according to methods such as, but not limited to inoculation of an appropriate animal with the polypeptide or an antigenic fragment, in vitro stimulation of lymphocyte populations, synthetic methods, hybridomas, and/or recombinant cells expressing nucleic acid encoding such anti-ASC or anti-NLR1 antibodies. Immunization of an animal using purified recombinant ASC or peptide fragments thereof, e.g., residues 178-193 (SEQ ID NO:1) of rat ASC (e.g., accession number BAC43754), EQ ID NO:2 of human ASC or residues 21-41 (SEQ ID NO: 5) of human ASC (e.g., accession number NP_037390.2), is an example of a method of preparing anti-ASC antibodies. Similarly, immunization of an animal using purified recombinant NLRP1 or peptide fragments thereof, e.g., residues MEE SQS KEE SNT EG-cys (SEQ ID NO:4) of rat NALP1 or SEQ ID NO:3 of human NALP1, is an example of a method of preparing anti-NLRP1 antibodies.

Monoclonal antibodies that specifically bind ASC or NLRP1 may be obtained by methods known to those skilled in the art. See, for example Kohler and Milstein, Nature 256:495-497, 1975; U.S. Pat. No. 4,376,110; Ausubel et al., eds., Current Protocols in Molecular Biology, Greene Publishing Assoc. and Wiley Interscience, N.Y., (1987, 1992); Harlow and Lane ANTIBODIES: A Laboratory Manual Cold Spring Harbor Laboratory Press, Cold Spring Harbor, NY, 1988; Colligan et al., eds., Current Protocols in Immunology, Greene Publishing Assoc. and Wiley Interscience, N.Y., (1992, 1993), the contents of which are incorporated entirely herein by reference. Such antibodies may be of any immunoglobulin class including IgG, IgM, IgE, IgA, GILD and any subclass thereof. A hybridoma producing a monoclonal antibody of the present invention may be cultivated in vitro, in situ or in vivo. In one embodiment, a hybridoma producing an anti-ASC monoclonal antibody of the present disclosure is the ICCN1.OH hybridoma. In another embodiment, a hybridoma producing an anti-ASC monoclonal antibody of the present disclosure produces monoclonal antibodies comprising a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3. In another embodiment, a hybridoma producing an anti-ASC monoclonal antibody of the present disclosure produces monoclonal antibodies comprising a heavy chain variable (VH) region and a light chain variable (VL) region, wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3. In yet another embodiment, a hybridoma producing an anti-ASC monoclonal antibody of the present disclosure produces monoclonal antibodies comprising a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3 and wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3.

Administration of Compositions

The compositions of the invention may be administered to mammals (e.g., rodents, humans) in any suitable formulation. For example, anti-ASC antibodies may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to mammals by any conventional technique. Typically, such administration will be by inhalation, intranasal or parenteral (e.g., intravenous, subcutaneous, intratumoral, intramuscular, intraperitoneal, or intrathecal introduction). The compositions may also be administered directly to a target site by, for example, surgical delivery to an internal or external target site, or by catheter to a site accessible by a blood vessel. The compositions may be administered in a single bolus, multiple injections, or by continuous infusion (e.g., intravenously, by peritoneal dialysis, pump infusion). For inhalation or intranasal administration, the compositions may be administered using an inhaler, a nebulizer, or any suitable device. For parenteral administration, the compositions can be formulated in a sterilized pyrogen-free form.

Effective Doses

The compositions described above can be administered to a mammal (e.g., a rat, human) in an effective amount, that is, an amount capable of producing a desirable result in a treated mammal (e.g., reducing inflammation in the CNS of a mammal subjected to a traumatic injury to the CNS or stroke or having an autoimmune or CNS disease). Such a therapeutically effective amount can be determined as described below. The therapeutically effective amount of a composition comprising an agent as provided herein (e.g., a monoclonal antibody or antibody fragment derived therefrom as provided herein such as, for example, IC-100) can generally be about 0.001, 0.005, 0.01, 0.05, 0.1, 0.5, 1, 2, 4, 6, 8, 10, 15, 20, 25, 30, 35, 40, 45, 50, 55, 60, 65, 70, 75, 80, 85, 90, 95, 100, 125, 150, 175 or 200 mg/kg of patient body weight. The therapeutically effective amount of a composition comprising an agent as provided herein (e.g., a monoclonal antibody or antibody fragment derived therefrom as provided herein such as, for example, IC-100) can generally be about 0.001 to about 200 mg/kg of patient body weight. The therapeutically effective amount of a composition comprising an agent as provided herein (e.g., a monoclonal antibody or antibody fragment derived therefrom as provided herein such as, for example, IC-100) can generally be about 0.001 mg/kg to about 0.01 mg/kg, about 0.01 mg/kg to about 0.1 mg/kg, about 0.1 mg/kg to about 1 mg/kg, about 1 mg/kg to about 10 mg/kg, about 10 mg/kg to about 25 mg/kg, about 25 mg/kg to about 50 mg/kg, about 50 mg/kg to about 75 mg/kg, about 75 mg/kg to about 100 mg/kg, about 100 mg/kg to about 125 mg/kg, about 125 mg/kg to about 150 mg/kg, about 150 mg/kg to about 175 mg/kg or about 175 mg/kg to about 200 mg/kg of the subject's body weight. The composition comprising an agent as provided herein (e.g., a monoclonal antibody or antibody fragment derived therefrom as provided herein such as, for example, IC-100) can be administered in single or multiple doses.

Toxicity and therapeutic efficacy of the compositions utilized in methods of the invention can be determined by standard pharmaceutical procedures, using either cells in culture or experimental animals to determine the $LD_{50}$ (the dose lethal to 50% of the population). The dose ratio between toxic and therapeutic effects is the therapeutic index and it can be expressed as the ratio $LD_{50}/ED_{50}$. In some cases, the compositions provided herein exhibit large therapeutic indices. While those that exhibit toxic side effects may be used, care should be taken to design a delivery system that minimizes the potential damage of such side effects. In some cases, the dosage of compositions provided herein lies within a range that includes an $ED_{50}$ with little or no toxicity. The dosage may vary within this range depending upon the dosage form employed and the route of administration utilized.

As is well known in the medical and veterinary arts, dosage for any one subject depends on many factors, including the subject's size, body surface area, age, the particular composition to be administered, time and route of administration, general health, and other drugs being administered concurrently.

EXAMPLES

The present invention is further illustrated by the following specific examples. The examples are provided for illustration only and should not be construed as limiting the scope of the invention in any way.

Example 1: Role of EV Mediated Inflammasome Signaling in ALI Following TBI and Effects of its Neutralization Pulmonary dysfunction often presents as a complication of Severe Traumatic Brain Injury (1). Approximately 20-25 percent of TBI subjects develop acute lung injury (ALI) (2), but the mechanisms mediating the pathology of TBI-induced ALI remain poorly defined. Previous literature has supported the idea that pulmonary dysfunction after TBI is due to the sympathetic response to increased intracranial pressure leading to cardiopulmonary dysfunction (42). More recent studies, however, have shown that a systemic inflammatory response also plays a key role in TBI-induced lung injury (43). Specifically, the HMGB1-RAGE ligand receptor pathway serves as central transduction mechanism for pulmonary dysfunction after TBI (8). In addition, HMGB1 induces AIM2 inflammasome activation (37). Furthermore previous literature reveals that pathogens secrete EV that carry DAMPs, such as HMGB1, and trigger inflammation (Buzas et al., 2014). Various studies have shown that the blood brain barrier (BBB) is permeable after TBI as early as 3-6 hours after injury resulting in damage to the protective barrier between the brain and the intravascular compartment and leads to leakage of proteins and fluid (44). Disruption of the BBB after injury results in the secretion of inflammatory mediators, such as DAMPs, which can further brain inflammation and damage distal organs (5). Several inflammatory mediators can act as clear markers for brain injury, however their validity is not widely accepted (45). Furthermore, there is currently no clinically approved treatment or biomarker for TBI-induced ALI. Recently, EV have become an area of interest in biomarker research for a several different types of diseases, including lung injury (46) and TBI (47). It has been previously shown that in EV isolated from the cerebrospinal fluid of patient with TBI, there is an increase of inflammasome proteins when compared to control samples (14). In this Example, the contribution of EV mediated inflammasome signaling in the etiology of TBI-induced ALI was examined.

Materials and Methods

Animals and Traumatic Brain Injury

All animal procedures were approved by the Institutional Animal Care and Use Committee of the University of Miami Miller School of Medicine (Animal Welfare Assurance A3224-01) and were done according to the NIH Guide for the Care and Use of Laboratory Animals. The ARRIVE guidelines were followed when conducting this study. All C57/BL6 mice were 8-12 weeks and 24 to 32 grams. Mice were prospectively randomized to experimental groups (sham, 4 h, 24) for TBI, experimental groups (naïve, sham-saline, untreated, enoxaparin, anti-ASC) for adoptive transfer and treatment. For TBI experiment-groups, sham animals underwent surgical procedure but were not injured. For adoptive transfer treatment studies, the sham-saline group underwent surgical procedures and received saline as vehicle treatment. Naïve animals underwent no surgical procedures. A sample size of 5 to 6 was used for each group based on power analysis (using G* power analysis, with an effect size F=0.85, α set a 0.05) and historical data[49, 50]. All mice were housed in the viral antigen free (VAF) animal facility at the Lois Pope Life Center at the University of Miami on 12-hour light/dark cycles and food and water were supplied ad libitum. The facility conducts husbandry procedures twice a week and checks on the conditions of the animals daily. Animals were observed post-op, where they were kept on a heating pad and body temperature was controlled with a rectal probe where it was maintained at 37° C., in our operation room and then transferred to the animal quarters.

Prior to surgery animals were anesthetized with ketamine and xylazine (intraperitoneal, i.p.). The anesthetized animals were then placed on a heating pad to ensure a body temperature of 37° C. TBI was performed using a Controlled Cortical Impact (CCI) model. A 5 mm craniotomy was made on the right cortex (−2.5 mm posterior, 2.0 mm lateral from Bregma). Injury was induced using the ECCI-6.3 device (Custom Design & Fabrication, Richmond, VA, USA) with a 3 mm impounder at 6 m/s velocity, 0.8 mm depth, and 150 ms impact duration (15). Following these procedures animals were returned to their cages and given food and water. Animals were sacrificed at 4 hours and 24 hours after TBI as described. Sham animals were anesthetized and subjected to the same pre-surgical incision as injured animals but did not undergo a craniotomy or contusion.

Tissue Collection

All animals were anesthetized with ketamine and xylazine, prior to perfusion. Animals then underwent tracheal perfusion. Lungs were infused with 4% paraformaldehyde (PFA) using a tracheal catheter at 20 cm H2O and then fixed in 4% PFA overnight at 4° C. Fixed lung tissues were paraffin embedded and 5 m sections were processed (16). Right lung tissue was collected for protein isolation and molecular analyses. Animals then underwent decapitation and right cortical tissue was collected for protein isolation and molecular analyses.

Pyroptosome Isolation Assay

Mice lung tissue lysates were filtered through a 5 μm low-binding polyvinylidene difluoride (PVDF) membrane (Millipore). After filtration, the supernatant was centrifuged at 2,700×g for 8 minutes. The pellet was resuspended in 40 μl of 3[(3-cholamidopropyl) dimethylammonio]-propane-sulfonic acid (CHAPS) buffer (20 mmol/L HEPES-KOH, pH 7.5, 5 mmol/L MgCl2, 0.5 mmol/L EGTA, 0.1 mmol/L phenylmethylsulfonyl fluoride, protease inhibitor cocktail, and 0.1% CHAPS). The pyroptosome was pelleted by centrifugation at 2,700×g for 8 minutes. The pellet was then resuspended and incubated in 27.8 μl of CHAPS buffer with 2.2 μl of disuccinimidyl substrate (9) for 30 minutes at room temperature to cross-link ASC dimers. Lastly, an equal amount of 2× Laemmli buffer was added and proteins were analyzed by immunoblotting using commercially available antibodies to ASC and Gasdermin D (GSD).

Nuclear and Cytoplasmic Extraction

Nuclear and Cytoplasmic fractions were extracted using the NE-PER Nuclear and Cytoplasmic Extraction Reagents (Thermo Scientific) according to manufacturer instructions. Briefly, mice lung tissue samples were cut into 20-100 mg pieces and centrifuged at 500×g for 5 minutes. Tissue pieces were the homogenized with the Cytoplasmic Extraction Reagent and centrifuged at 16,000×g for 5 minutes. Then the supernatant (cellular extract) was removed and the pellet was centrifuged with Nuclear Extraction Reagent (Thermo Scientific) at 16,000×g for 10 minutes. This supernatant corresponded to the nuclear fraction, which was removed and stored at −80° C.

Immunoblotting

Lung and brain tissue samples were snap frozen in liquid nitrogen and stored in −80° C. 2-mm sections of right lower lung and right cortical tissue were homogenized in extraction buffer containing protease and phosphatase inhibitor cocktail (Sigma, St Louis, MO, USA) and resolved in 4-20% Tris-TGX Criterion precasted gels (Bio-Rad, Hercules, CA, USA) as described in de Rivero Vaccari et al. 2015 (13) using antibodies to caspase-1 (Novus Biologicals), ASC (Santa Cruz), IL-1 (Cell Signaling), IL-18 (Abcam) AIM2 (Santa Cruz) and HMGB1 (Millipore). Quantification of band density was performed using Image Lab and all data were normalized to 0-actin.

Immunohistochemistry

Tissue sections were deparaffinized in xylene and then rehydrated using ethanol and Tris buffer saline. Immunohistochemical procedures were then carried out for double staining as previously described (16). Sections were incubated overnight at 4° C. with antibodies against Caspase-1 and ASC (Millipore), AIM2 (Santa Cruz), HMGB1 (Millipore) and SPC (Millipore). Immunostained lung sections of sham, 4 hour, and 24 hour mice were examined with a Zeiss laser scanning confocal microscope (Zeiss, Inc., Thornwood, NY, USA). Lung sections were analyzed by individuals who were blinded to the groups.

EV Isolation

EV were isolated from serum from TBI-injured mice and injury mice using the Total Exosome Isolation solution according to manufacturer's instructions (Invitrogen). Briefly, 100 μl of each sample were centrifuged at 2000×g for 30 minutes. The supernatant was then incubated with 20 μl of Total Exosome Isolation (TEI) reagent for 30 minutes at 4° C. followed by centrifugation at 10,000×g for 10 minutes at room temperature. Supernatants were discarded and the pellet was resuspended in 100 μl of PBS. EV were characterized by the expression of CD81 and by Nanosight tracking analysis (FIG. 6).

Adoptive Transfer of EV

Serum-derived EV from C57BL-6 TBI and sham mice were injected into naïve C57BL-6 mice through the jugular vein at a dose of $1.0 \times 10^{10}$ particles per gram/body weight[48]. Particle count was measured by Nanosight Tracking analysis and samples were diluted accordingly. Prior to surgery animals were anesthetized with ketamine and xylene. A 1-2 cm incision was made between the jaw and the clavicle. The jugular vein was elevated and tied, followed by catheter placement. Serum-derived EV were transferred and lung and brain tissues were collected 24 hours after injection for analysis (n=5).

Enoxaparin and Anti-ASC Treatment

Serum-derived EV from TBI mice were injected into naïve C57-BL6 mice through a jugular vein injection. One hour later, Enoxaparin (3 mg/kg) (n=4) and Anti-ASC (5 mg/kg) (n=4) were administered to recipient animals. The following groups were used: 1) the naïve group received no treatment, 2) the sham saline group was used as a negative control and underwent jugular vein injection of only saline, 3) the untreated group received EV from TBI mice without any treatment and was used as a positive control, 4) the ENOX group received EV from TBI mice and Enoxaparin, and 5) the Anti-ASC group received EV from TBI mice and Anti-ASC. The order of treatment was randomized. Lung and brain tissues were collected 24 hours after injection for analysis. It should be noted that the anti-ASC antibody used in the treatment experiments was a humanized monoclonal antibody against ASC and recognizes murine, human and swine ASC.

Histology and Lung Injury Scoring

Lung tissue sections were stained by a standard hematoxylin and eosin method for histology, morphometry and ALI scoring. Lung sections were scored by a blinded pathologist using the Lung Injury Scoring System from the American Thoracic Society Workshop Report (17). Twenty random high power fields were chosen for scoring. Criteria for ALI scoring was based on number of neutrophils in the alveolar space, interstitial space, hyaline membranes, proteinaceous debris filling the airspaces and alveolar septal thickening. Based on these criteria a score between 0 (no injury) and 1 (severe injury) was given.

Statistical Analysis

Data were analyzed using a student's T-test for two groups and a one-way ANOVA followed by Tukey's multiple comparison tests, (GraphPad Prism version 7.0) for two or more groups. D'Agostino-Pearson test was used to test for normality. Data are expressed as mean+/−SEM. P values of significance used were * p<0.05.

Results

Severe TBI Increases AIM2 Inflammasome Proteins and HMGB1 Expression in the Brain of Mice Excessive levels of the proinflammatory cytokine IL-1β and IL-18, and inflammasome proteins are associated with secondary damage after fluid-percussion brain injury (18). To determine whether severe CCI induced processing of proinflammatory cytokines and alterations in levels of inflammasome proteins, cortical lysates were analyzed, however there is limited research on inflammasome activation in severe TBI. In this Example, following severe CCI, cortical lysates were examined for the levels of the caspase-1 (FIG. 1A, B) (p<0.001), ASC (FIG. 1A, C) (p=0.003), IL-18 (FIG. 1A, D) (p=0.0042), AIM2 (FIG. 1A, F) (p=0.0197) and IL-1β (FIG. 1 A, G) (p=0.0141) at 4 and 24 hrs after injury. Levels of caspase-1, ASC, AIM2, and IL-1β peaked at 4 hours after CCI and decreased by 24 hrs. The time course for maturation of inflammatory cytokines differed slightly but peaked by 24 hours after TBI. Since others have shown a role for the inflammasome DAMP HMGB1 activating the AIM2 inflammasome, the levels of these proteins were also determined in cortical lysates. As shown in FIGS. 1A, 1E, CCI induced a significant increase in the levels of HMGB1 (FIG. 1A, 1E) (p=0.0121) at 4 and 24 hrs after injury. These data indicate that following severe CCI in mice, the levels of the AIM2 inflammasome proteins were significantly elevated in the cortex following injury.

Severe TBI Increases AIM2 Inflammasome Protein and HMGB1 Expression on the Lungs of Mice To determine whether CCI induced inflammasome activation in the lungs, an immunoblot analysis of lung lysates was performed for caspase-1 (FIG. 1 H, I) (p=0.0026), ASC (FIG. 1 H, J) (p=0.0427), IL-18 (FIG. 1H, K) (p=0.0025), IL-1β (FIG. 1 H, N) (p=0.0012) and AIM2 (FIG. 1 H, M) (p<0.001), and NLRP3 (p=0.0047) (Supplemental FIG. 1). Increased levels of caspase-1, ASC, IL-18 and AIM2 were significantly increased at 4 hrs and 24 hrs after injury as compared to the sham control. However the time course of the increase in protein expression differed slightly from that observed in brain in which they peaked at 24 hr after CCI. Since, the HMGB1-RAGE axis plays a role in the mechanism by which TBI induces lung dysfunction (8), lung lysates were analyzed for levels of HMGB1 protein expression. FIGS. 1H, 1L (p=0.0158) shows that HMGB1 expression increased at 4 and 24 hours after TBI, indicating that the AIM2 inflammasome and HMGB1 play a role in the inflammatory response in the lungs post-TBI.

TBI Induces Pyroptosis in the Lungs of Mice

As shown previously, activation of the AIM2 inflammasome in cortical neurons leads to pyroptotic cell death (19). To investigate whether TBI results in pyroptosis in mice lung tissue, the pyroptosome in lung tissue was isolated after TBI. TBI animals, sacrificed at 4 hours post-injury showed evidence of ASC oligomerization compared to sham animals (FIG. 4A). ASC dimers, and trimers were seen in TBI animals (50, 75 kDA respectively). These results were indicative of pyroptosome formation, which can be characterized by the supramolecular assembly of ASC oligomers. In addition, gasdermin D (GSDMD), which is cleaved upon activation of caspase-1 and triggers pyroptosis and the release of IL-1β (20), was significantly increased in the lungs of TBI animals compared to sham (FIGS. 4B and 4C) (p=0.0001). These findings indicated that pyroptosis contributes to cell death in lung tissue after TBI.

Figure 2A:
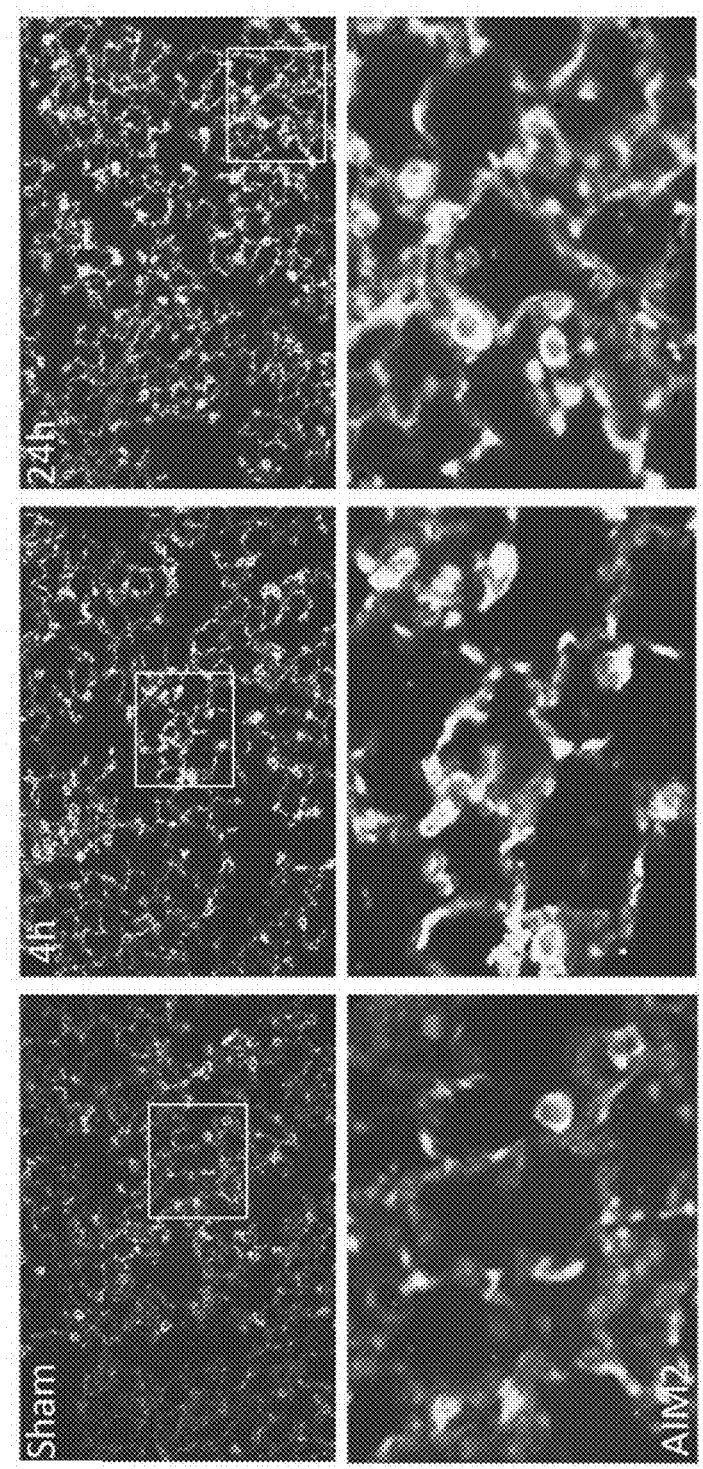
FIG. 2A-2C illustrates expression of inflammasome proteins in Type II alveolar epithelial cells.
Figure 2B:
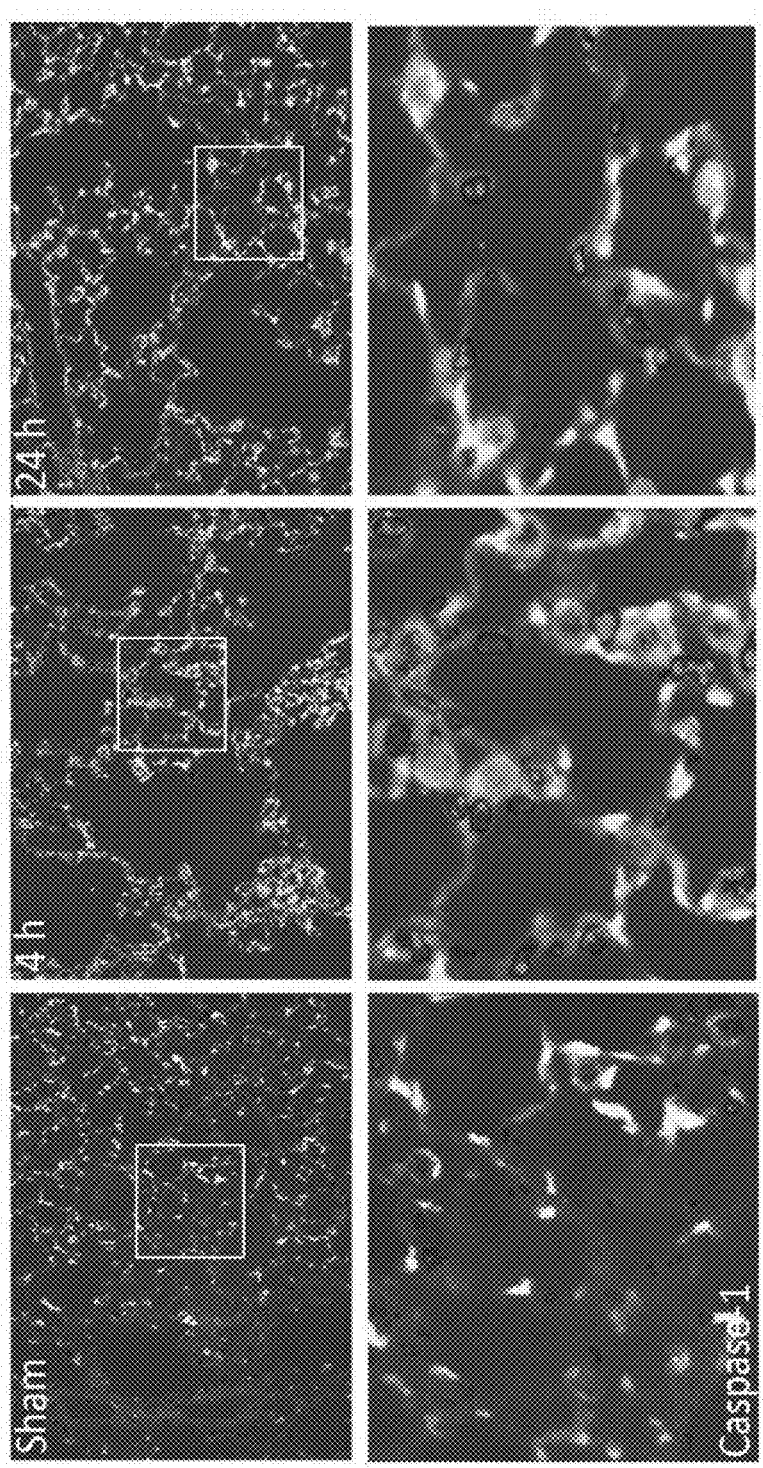
Figure 2C:
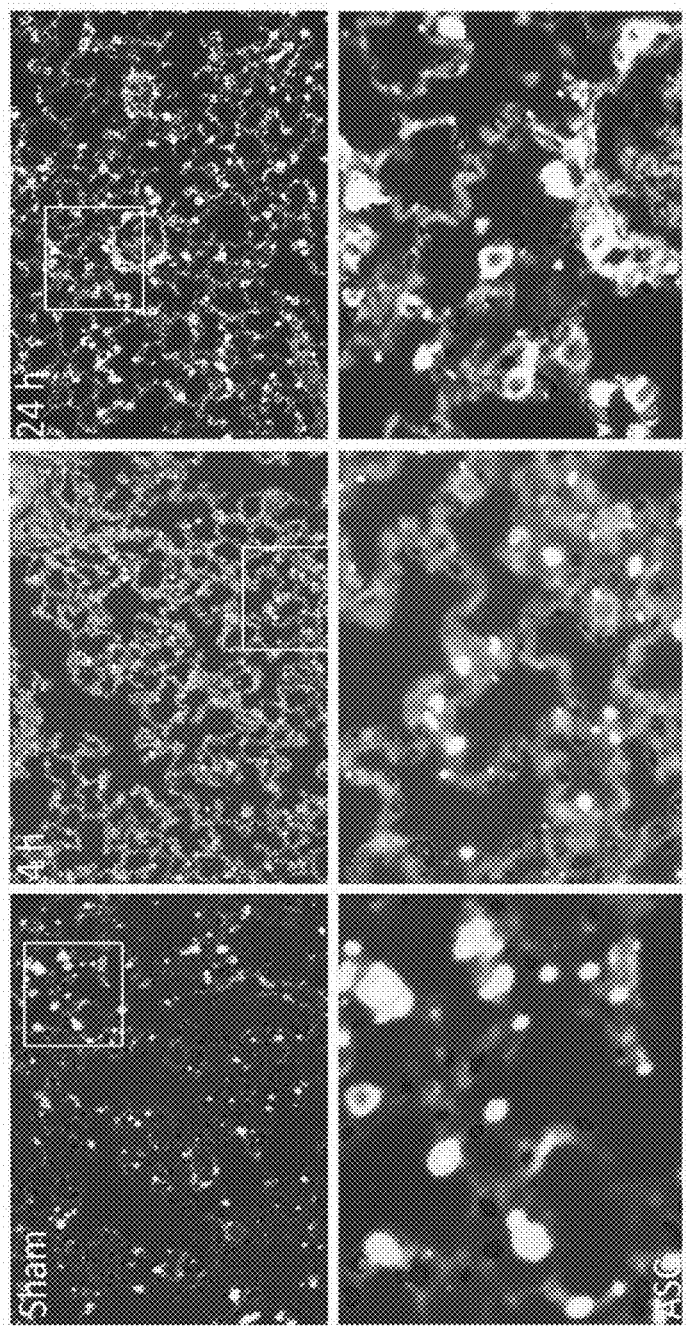

TBI Increases Immunoreactivity of Inflammasome Proteins in Type II Alveolar Epithelial Cells TBI may lead to capillary leak, resulting in increased vascular permeability and damage to specialized alveolar epithelial cells, called type II pneumocytes (5). To examine the cellular effects of TBI on inflammasome expression in the lungs after injury, immunohistochemical analysis was performed in lung sections of sham, 4 hour, and 24 hour injured animals. Type II alveolar epithelial cells are known to be the main type of lung cells injured in ALI (17). Lung sections were stained with antibodies against AIM2, caspase-1, and ASC (green) and co-stained with Pro-surfactant protein C (Pro-SPC, red), a marker of type II epithelial cells, and DAPI nuclear staining (blue). As shown in FIG. 2A-2C, active caspase-1 (FIG. 2A), ASC (FIG. 2B), as well as AIM2 (FIG. 2C) are present in SPC-positive cells (arrow). Immunoreactivity of these inflammasome proteins increased after TBI. These findings indicate that inflammasome proteins are expressed in type II alveolar epithelial cells and that TBI results in increased immunoreactivity in these cells.

TBI Increases Nuclear and Cytoplasmic HMGB1 Expression

Figure 3A:
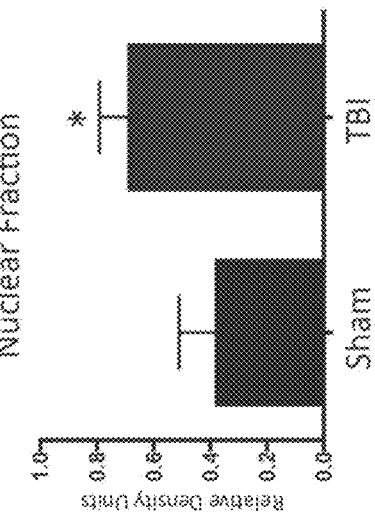
FIG. 3A-3E illustrates TBI increases nuclear and cytoplasmic HMGB1 expression in mice lung.
Figure 3B:
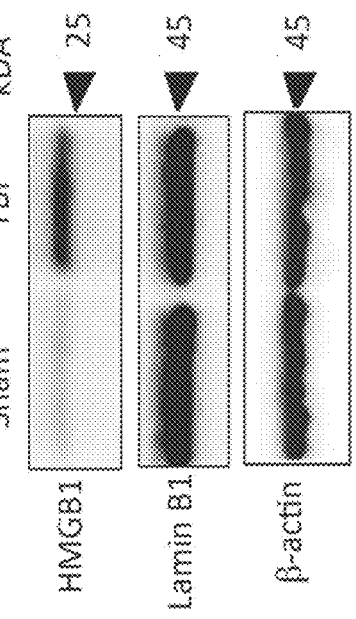
Figure 3C:
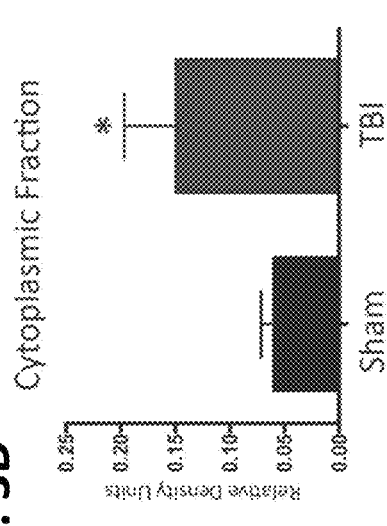
Figure 3D:
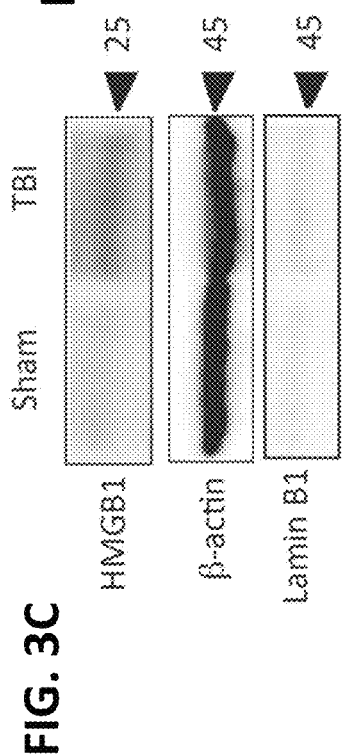
Figure 3E:
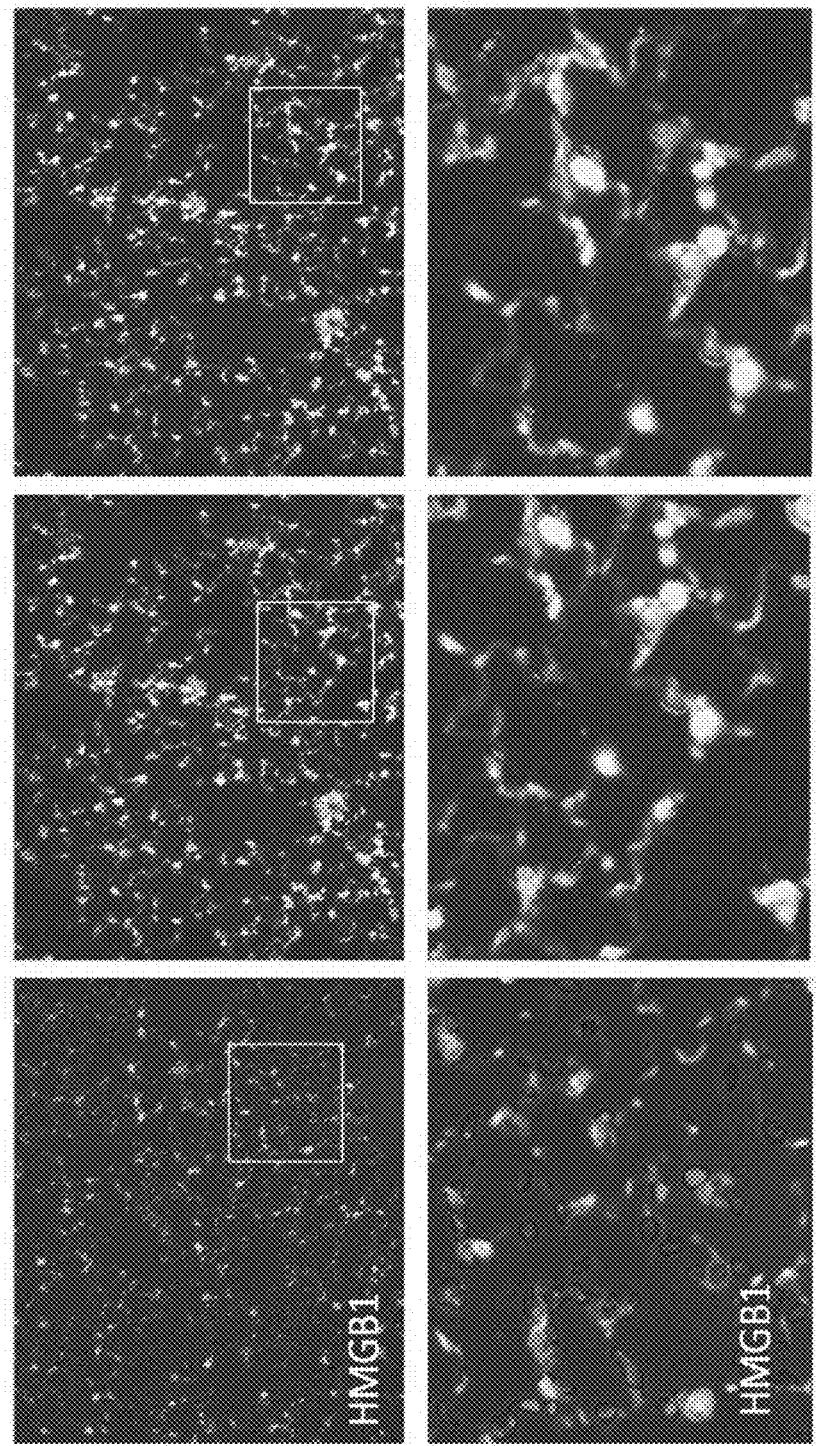

In order to determine the cellular distribution of HMGB1 in lung cells after TBI, nuclear and cytoplasmic fractions from lung homogenates were isolated (FIG. 3A, 3C) (p=0.0337). Immunoblotting indicated that both fractions had significant increases in HMGB1 expression at 4 hrs post-TBI (FIG. 3B, 3D) (p=0.0345). Immunohistochemical analysis of HMGB1 was also performed in order to determine the changes in immunoreactivity in lung sections after TBI. Sections were co-stained for HMGB1 (green) and SPC (red) and DAPI nuclear staining (blue). Immunoreactivity of HMGB1 was increased at 4 hrs and 24 hrs when compared to sham. Weak immunoreactivity of HMGB1 was observed in SPC-positive cells (arrow) (FIG. 3E); therefore, suggesting that HMGB1 changes in the injured lung tissue may be cytoplasmic.

TBI Induces Changes in Lung Morphology and Induces ALI

Figure 5A:
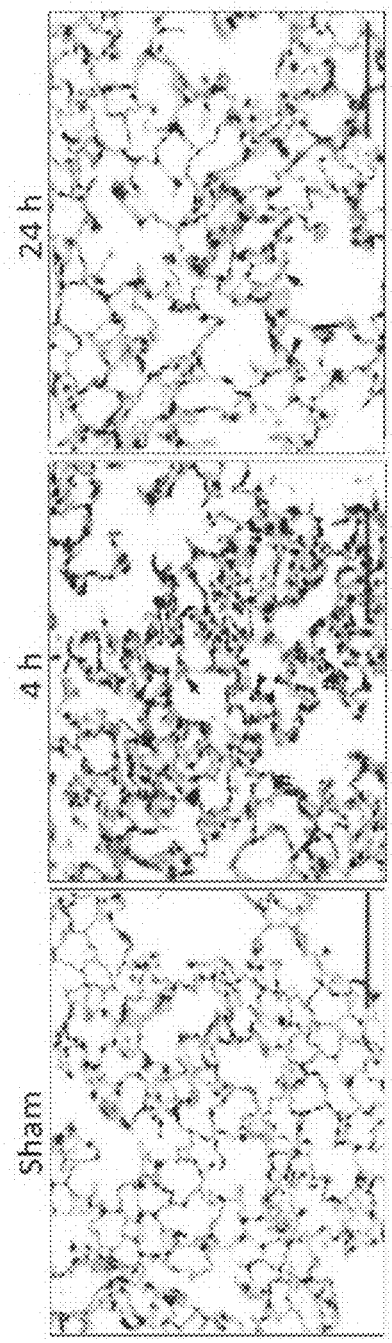
FIG. 5A-5B illustrates TBI induces alveolar morphological changes and acute lung injury in mice.

ALI can be characterized by inflammatory processes, which lead to alveolar and interstitial edema as well as infiltration of inflammatory cells into the alveolar space (23). Histopathological analysis of lung tissue (FIG. 5A) indicate that severe TBI causes substantial changes in the lung architecture and morphology at 4 and 24 hours after injury. Sham animals showed a normal alveolar morphology, whereas injured animals showed acute changes in alveolar edema but decreased slightly by 24 hours after injury (long arrows). In addition, there was evidence of neutrophil infiltration (arrow heads) and changes in morphology of alveolar capillary membranes (*) at both time points. Injured animals showed signs of interstitial edema, which was more pronounced at 4 hours post-injury, but was still evident at 24 hours post injury (short arrows). Lastly, injured animals also showed evidence of thickening of the interstitial area and the alveolar septum (pound, #).

Figure 5B:
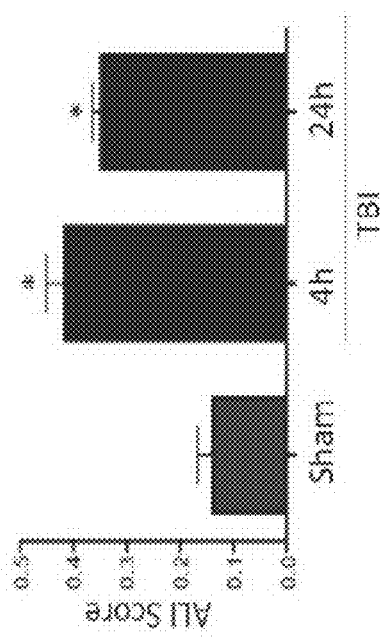

To confirm that severe injury induces ALI, histological sections were analyzed using the ALI scoring system defined by the American Thoracic Society (17). This system is based on evidence of neutrophil infiltration into the alveolar and interstitial spaces, hyaline membrane formation, proteinaceous debris filling the airspaces, and alveolar septal thickening. (17). These characteristics were significantly elevated in injured animals and ALI scores were higher overall in TBI animals compared to sham (FIG. 5B) (p=0.0017).

Figure 7C:
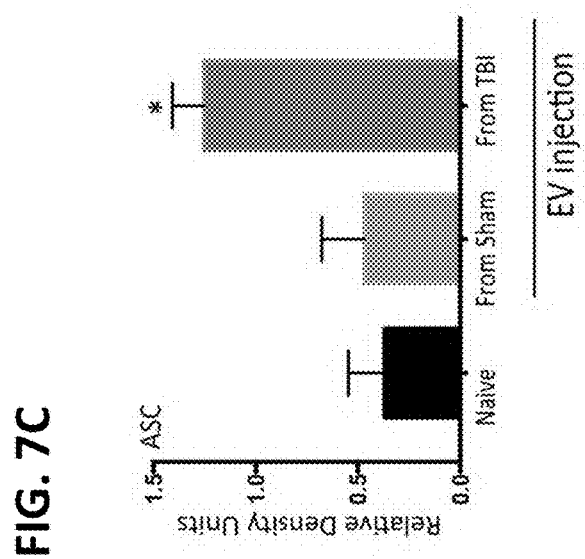
FIG. 7A-7G illustrates adoptive transfer of EV from TBI animals induce caspase-1 and ASC in the lungs of uninjured mice.
Figure 7B:
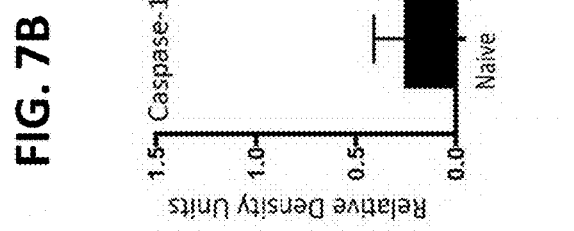
Figure 7A:
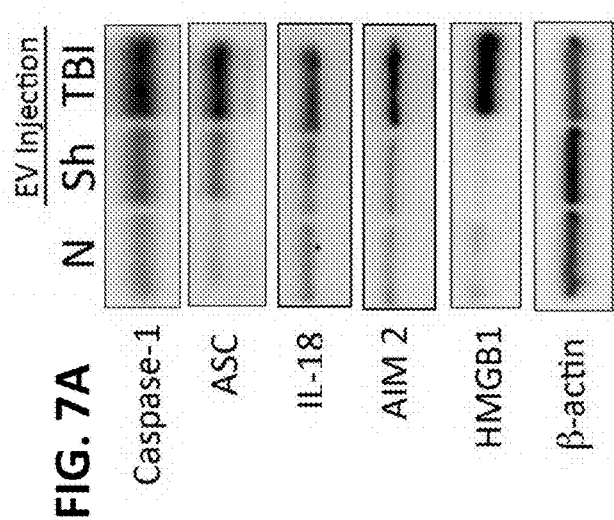
Figure 7D:
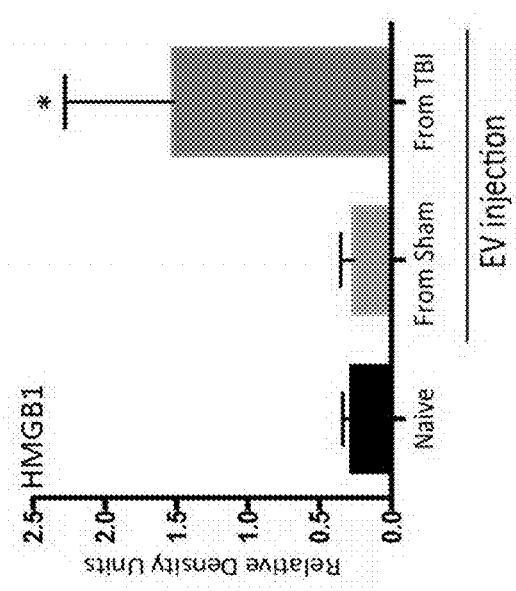
Figure 7E:
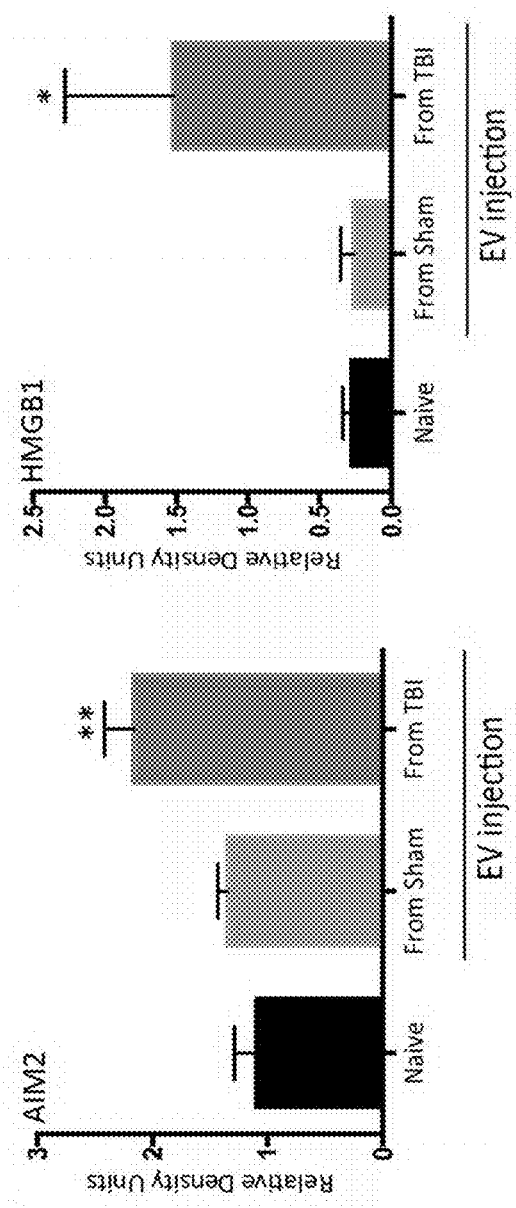
Figure 7F:
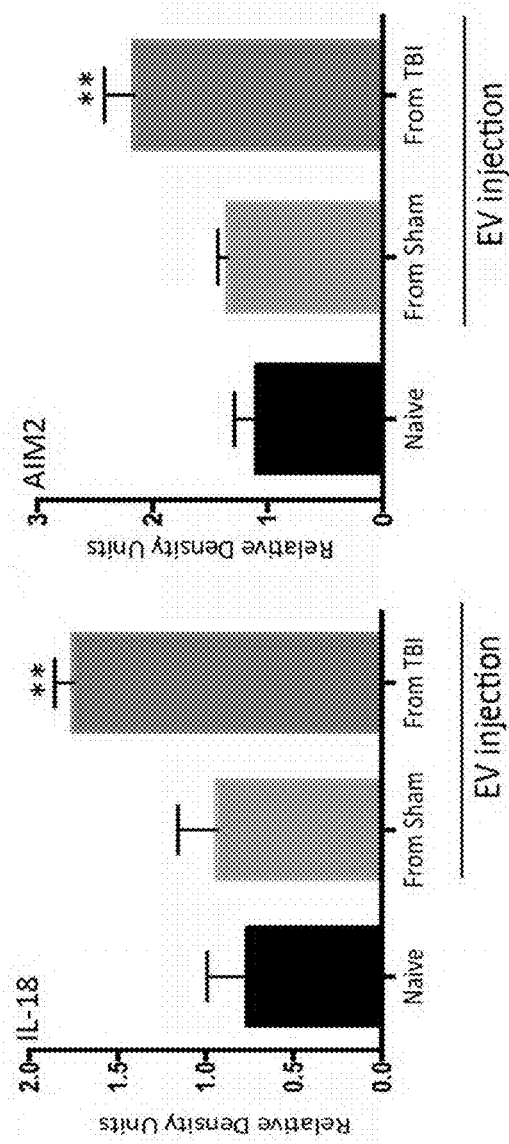
Figure 7G:
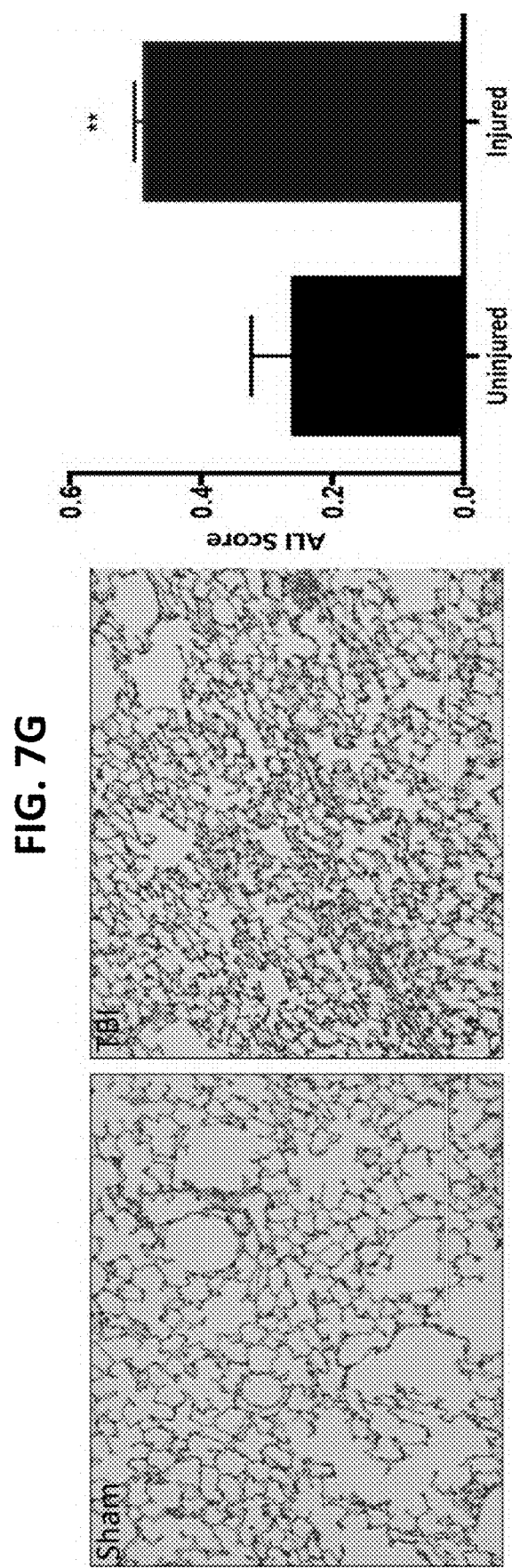
Figure 8E:
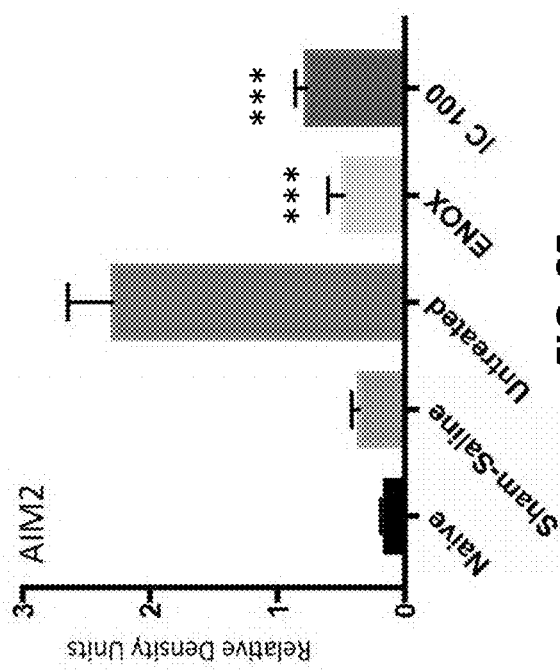
Figure 8F:
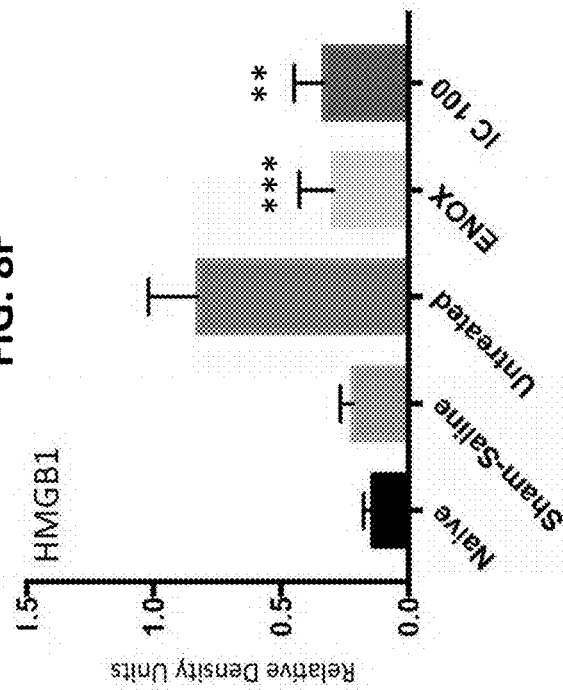
Figure 8D:
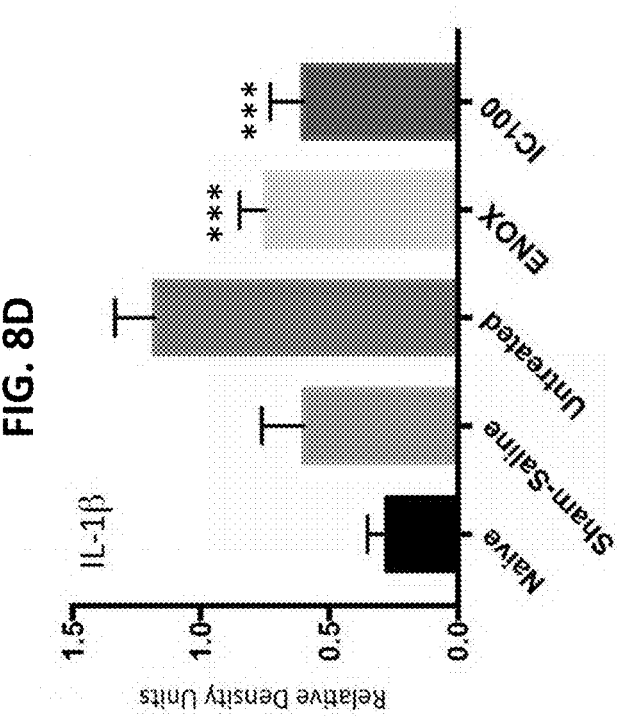
Figure 9E:
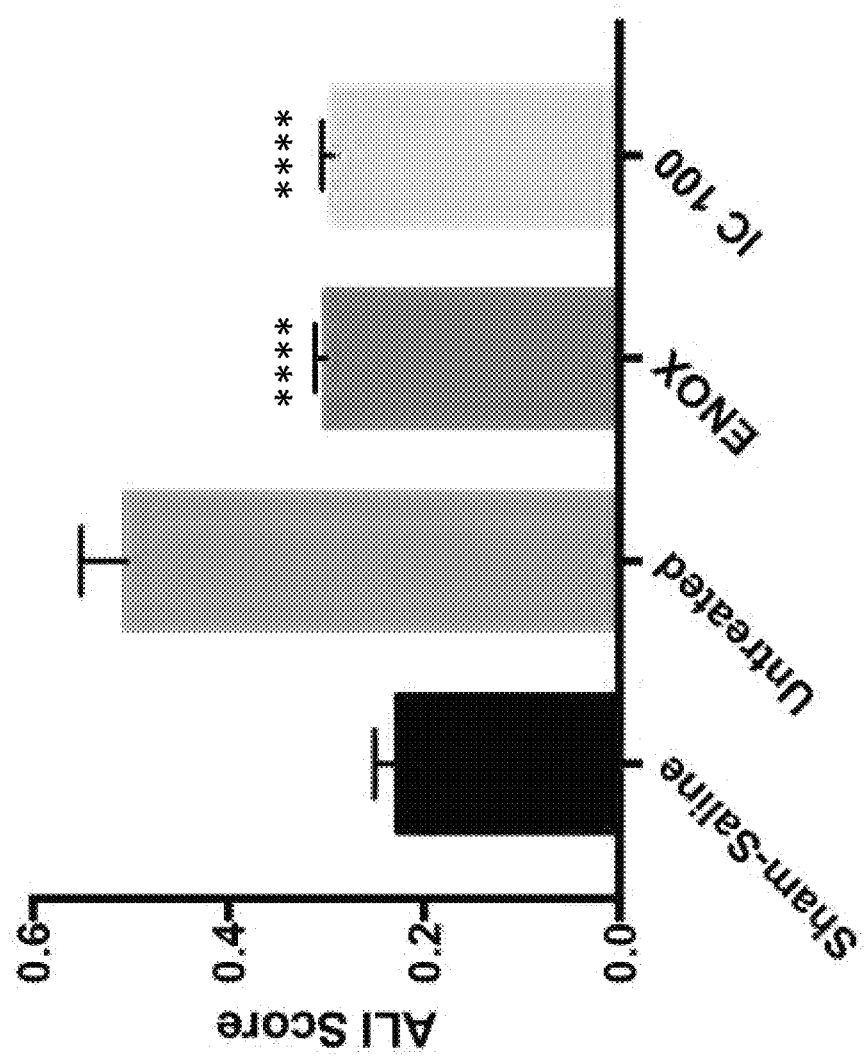

Enoxaparin and Anti-ASC Antibody Treatment Significantly Reduces Inflammasome Expression and ALI after Adoptive Transfer of EV from TBI Mice In order to provide evidence that EV and their cargo that can be released into the circulation after TBI may induce inflammasome activation in the lung, a classic adoptive transfer experiment was performed using serum-derived EV from severe CCI mice. EV preparations were validated using Western Blot for EV marker CD81 (FIG. 6). Controls received EV isolated from sham or naïve animals. As shown in FIG. 7A-7F, active caspase-1 (FIG. 7A, 7B), ASC (FIG. 7A, 7C), IL-18 (FIG. 7A, 7D), AIM2 (FIG. 7A, 7E) and HMGB1 (FIG. 7A, 7F) were significantly elevated in the lungs of animals that received the EV from TBI injured animals when compared to the lungs of animals that receive EV from uninjured or naïve mice or naïve mice. Furthermore, infiltration of inflammatory cells (arrows) was apparent in lungs treated with EV from TBI mice (FIG. 7G). Lastly, ALI score was also significantly higher in animals that received EV from injured mice (FIG. 7G). These studies provided evidence for a neural-respiratory-inflammasome axis in which EV released into the circulation after TBI activate the inflammasome in lung target cells contributing to the pathogenesis of ALI.

Next, exosome uptake blockade was attempted by treatment with either Enoxaparin or a monoclonal antibody against ASC after adoptive transfer of EV from injured to naïve mice. Negative control animals received saline and positive control animals received no treatment. As shown in FIG. 8A-8F, Caspase-1 (FIG. 8A, 8B), ASC (FIG. 8A, 8C), TL-1β (FIG. 8A, 8D), AIM2 (FIG. 8A, 8E), and HMGB1 (FIG. 8A, 8F) were significantly reduced (p=<0.0001) as compared to untreated (positive control) group after treatment with Enoxaparin or a humanized monoclonal anti-ASC antibody (e.g. IC 100 antibody). In addition, H&E stained lung sections showed significantly less neutrophil infiltration into alveolar and interstitial space, as well as no signs of septal thickening (FIG. 9A-D). ALI scores for animals treated with Enoxaparin and anti-ASC antibody (IC 100) were significantly lower compared to untreated group (FIG. 9E) (p=<0.0001). Thus, EV released into the circulation after TBI play a role in inflammasome activation in lung cells leading to ALI.

Conclusions

TBI can be associated with higher rates of certain medical complications, especially pulmonary and central nervous system dysfunction. In this Example, severe TBI was shown to increase HMGB1 and inflammasome expression (e.g., AIM2, caspase-1 and ASC expression) in cortical and lung tissue and induce changes in lung morphology consistent with ALI (e.g., infiltration of neutrophils into the alveolar and interstitial space, alveolar septal thickening, and alveolar edema and hemorrhage) and introduces the idea of a Neural Respiratory Inflammatory Axis. Importantly, TBI resulted in pyroptosis in lung tissue (e.g., presence of GSDMD cleavage) and increased expression of inflammasome proteins in Type II alveolar epithelial cells. Additionally, adoptive transfer of EV from TBI mice activated the inflammasome and induced ALI, indicating that brain injury induces the release of EV containing a cargo of inflammasome proteins that are then carried to the resulting in ALI. Moreover, it was shown that by both inhibiting EV uptake (Enoxaparin) and inflammasome activation (anti-ASC antibody (IC 100) treatment), there is a reduction in inflammasome protein expression and in the development of ALI.

In summary, this Example showed that AIM2 inflammasome signaling plays a central role in the pathomechanism of lung injury after TBI and demonstrates a mechanism of TBI-induced ALI involving EV-mediated inflammasome signaling. These data provided evidence that EV-mediated inflammasome signaling can play a central role involving a Neuronal-Respiratory-Inflammatory Axis. Therefore, targeting this axis with antibodies against inflammasome proteins or drugs that block EV uptake may provide a therapeutic approach in Neurotrauma-induced ALI in all areas of critical care medicine. In light of these results, the disclosed therapeutic strategies may be useful for the treatment of inflammatory diseases of the lung in general.

INCORPORATION BY REFERENCE

The following references are incorporated by reference in their entireties for all purposes.
1. Pfeifer R, et al. (2015) Development of a standardized trauma-related lung injury model. *J SurgRes* 196(2):388-394.
2. Summers C R, Ivins B, & Schwab K A (2009) Traumatic brain injury in the United States: an epidemiologic overview. *The Mount Sinai journal of medicine, New York* 76(2):105-110.
3. Erickson S E, et al. (2009) Recent trends in acute lung injury mortality: 1996-2005. *Crit Care Med* 37(5):1574-1579.
4. Nicolls M R & Laubach V E (2014) Traumatic brain injury: lungs in a RAGE. *Sci TranslMed* 6(252):252fs234.
5. Rincon F, et al. (2012) Impact of acute lung injury and acute respiratory distress syndrome after traumatic brain injury in the United States. *Neurosurgery* 71(4):795-803.
6. Andersson U & Rauvala H (2011) Introduction: HMGB1 in inflammation and innate immunity. *JIntern Med* 270 (4):296-300.
7. Weber D J, et al. (2014) The HMGB1-RAGE axis mediates traumatic brain injury-induced pulmonary dysfunction in lung transplantation. *Sci Transl Med* 6(252): 252ra124.
8. Lu B, et al. (2012) Novel role of PKR in inflammasome activation and HMGB1 release. *Nature* 488(7413):670-674.
9. de Rivero Vaccari J P, Dietrich W D, & Keane R W (2014) Activation and regulation of cellular inflammasomes: gaps in our knowledge for central nervous system injury. *Journal of cerebral blood flow and metabolism: official journal of the International Society of Cerebral Blood Flow andMetabolism* 34(3):369-375.
10. Ware L B & Matthay M A (2000) The Acute Respiratory Distress Syndrome. *New England Journal of Medicine* 342(18):1334-1349.
11. Yanez-Mo M, et al. (2015) Biological properties of extracellular vesicles and their physiological functions. *J Extracell Vesicles* 4:27066.
12. Qu Y, Franchi L, Nunez G, & Dubyak G R (2007) Nonclassical IL-1 beta secretion stimulated by P2X7 receptors is dependent on inflammasome activation and correlated with exosome release in murine macrophages. *J Immunol* 179(3):1913-1925.

13. de Rivero Vaccari J P, et al. (2015) Exosome-mediated inflammasome signaling after central nervous system injury. *J Neurochem.* January; 136 Suppl 1:39-48. doi: 10.1111/jnc.13036.
14. Atkins C M, Cepero M L, Kang Y, Liebl D J, & Dietrich W D (2013) Effects of early rolipram treatment on histopathological outcome after controlled cortical impact injury in mice. *Neurosci Lett* 532:1-6.
15. Wu S, et al. (2010) Conditional overexpression of connective tissue growth factor disrupts postnatal lung development. *American journal of respiratory cell and molecular biology* 42(5):552-563.
16. Matute-Bello G, et al. (2011) An official American Thoracic Society workshop report: features and measurements of experimental acute lung injury in animals. *American journal of respiratory cell and molecular biology* 44(5):725-738.
17. de Rivero Vaccari J P, et al. (2009) Therapeutic neutralization of the NLRP1 inflammasome reduces the innate immune response and improves histopathology after traumatic brain injury. *Journal of cerebral blood flow and metabolism: official journal of the International Society of Cerebral Blood Flow and Metabolism* 29(7):1251-1261.
18. Adamczak S E, et al. (2014) Pyroptotic neuronal cell death mediated by the AIM2 inflammasome. *Journal of cerebral blood flow and metabolism: official journal of the International Society of Cerebral Blood Flow and Metabolism* 34(4):621-629.
19. Liu X, et al. (2016) Inflammasome-activated gasdermin D causes pyroptosis by forming membrane pores. *Nature* 535(7610):153-158.
20. Dolinay T, et al. (2012) Inflammasome-regulated cytokines are critical mediators of acute lung injury. *Am J Respir Crit Care Med* 185(11):1225-1234.
21. Muller M C, et al. (2014) Contribution of damage-associated molecular patterns to transfusion-related acute lung injury in cardiac surgery. *Blood transfusion=Trasfusione del sangue* 12(3):368-375.
22. Ragaller M & Richter T (2010) Acute lung injury and acute respiratory distress syndrome. *Journal of emergencies, trauma, and shock* 3(1):43-51.
23. Lee K & Rincon F (2012) Pulmonary complications in patients with severe brain injury. *Critical care research an dpractice* 2012:207247.
24. Yasui H, Donahue D L, Walsh M, Castellino F J, & Ploplis V A (2016) Early coagulation events induce acute lung injury in a rat model of blunt traumatic brain injury. *American journal of physiology. Lung cellular and molecular physiology* 311(1):L74-86.
25. Hendrickson C M, et al. (2016) The acute respiratory distress syndrome following isolated severe traumatic brain injury. *J Trauma Acute Care Surg.*
26. Cross L J & Matthay M A (2011) Biomarkers in acute lung injury: insights into the pathogenesis of acute lung injury. *Crit Care Clin* 27(2):355-377.
27. Butt Y, Kurdowska A, & Allen T C (2016) Acute Lung Injury: A Clinical and Molecular Review. *Archives of pathology & laboratory medicine* 140(4):345-350.
28. Luh S P & Chiang C H (2007) Acute lung injury/acute respiratory distress syndrome (ALI/ARDS): the mechanism, present strategies and future perspectives of therapies. *Journal of Zhejiang University. Science. B* 8(1):60-69.
29. Matute-Bello G & Martin T R (2003) Science review: apoptosis in acute lung injury. *Critical care* 7(5):355-358.
30. Miao E A, Rajan J V, & Aderem A (2011) Caspase-1-induced pyroptotic cell death. *Immunological reviews* 243(1):206-214.
31. Hornung V, et al. (2009) AIM2 recognizes cytosolic dsDNA and forms a caspase-1-activating inflammasome with ASC. *Nature* 458(7237):514-518.
32. Lam N Y, Rainer T H, Chan L Y, Joynt G M, & Lo Y M (2003) Time course of early and late changes in plasma DNA in trauma patients. *Clinical chemistry* 49(8):1286-1291.
33. Fernandes-Alnemri T & Alnemri E S (2008) Assembly, purification, and assay of the activity of the ASC pyroptosome. *Methods Enzymol* 442:251-270.
34. Man S M & Kanneganti T D (2016) Converging roles of caspases in inflammasome activation, cell death and innate immunity. *Nature reviews. Immunology* 16(1):7-21.
35. Liu L, et al. (2014) HMGB1-DNA complex-induced autophagy limits AIM2 inflammasome activation through RAGE. *Biochem Biophys Res Commun* 450(1):851-856.
36. Hoesch R E, et al. (2012) *Acute lung injury in critical neurological illness. Critical care medicine* 40(2):587-593.
37. Kalsotra A, Zhao J, Anakk S, Dash P K, & Strobel H W (2007) Brain trauma leads to enhanced lung inflammation and injury: evidence for role of P4504Fs in resolution. *Journal of cerebral blood flow and metabolism: official journal of the International Society of Cerebral Blood Flow and Metabolism* 27(5):963-974.
38. Hay (2015) Blood-Brain Barrier Disruption Is an Early Event That May Persist for Many Years After Traumatic Brain Injury in Humans. *J Neuropathol Exp Neurol* 74(12):1147-1157.
39. Zygun D A, Kortbeek J B, Fick G H, Laupland K B, & Doig C J (2005) Non-neurologic organ dysfunction in severe traumatic brain injury. *Critical care medicine* 33(3):654-660.
40. Peltz E D M E, Eckels P C, Damle S S, Tsuruta Y, Johnson J L, Sauaia A, Silliman C C, Banerjee A, Abraham E. (209) HMGB1 is markedly elevated within 6 hours of mechanical trauma in humans. *Shock* 32(1):17-22.
41. Chi W, et al. (2015) HMGB1 promotes the activation of NLRP3 and caspase-8 inflammasomes via N F-kappaB pathway in acute glaucoma. *Journal of neuroinflammation* 12:137.
42. Woodcock T & Morganti-Kossmann M C (2013) The role of markers of inflammation in traumatic brain injury. *Frontiers in neurology* 4:18.
43. Monsel A, Zhu Y G, Gudapati V, Lim H, & Lee J W (2016) Mesenchymal stem cell derived secretome and extracellular vesicles for acute lung injury and other inflammatory lung diseases. *Expert opinion on biological therapy* 16(7):859-871.
44. Taylor D D & Gercel-Taylor C (2014) Exosome platform for diagnosis and monitoring of traumatic brain injury. *Philosophical transactions of the Royal Society of London. Series B, Biological sciences* 369(1652).
45. Guo H, Callaway J B, & Ting J P (2015) Inflammasomes: mechanism of action, role in disease, and therapeutics. *Nature medicine* 21(7):677-687.
46. Silverman W R, et al. (2009) The pannexin 1 channel activates the inflammasome in neurons and astrocytes. *The Journal of biological chemistry* 284(27):18143-18151.
47. Tomura S, de Rivero Vaccari J P, Keane R W, Bramlett H M, & Dietrich W D (2012) Effects of therapeutic hypothermia on inflammasome signaling after traumatic brain injury. *Journal of cerebral blood flow and metabolism: official journal of the International Society of Cerebral Blood Flow and Metabolism* 32(10):1939-1947.
48. Wiklander, O. P., Nordin, J. Z., O'Loughlin, A., Gustafsson, Y., Corso, G., Mager, I., Vader, P., Lee, Y., Sork, H., Seow, Y., Heldring, N., Alvarez-Erviti, L., Smith, C. I., Le Blanc, K., Macchiarini, P., Jungebluth, P., Wood, M. J. and Andaloussi, S. E. (2015). Extracellular vesicle in vivo biodistribution is determined by cell source, route of administration and targeting. J Extracell Vesicles 4, 26316.
49. de Rivero Vaccari, J. P., Lotocki, G., Marcillo, A. E., Dietrich, W. D. and Keane, R. W. (2008). A molecular platform in neurons regulates inflammation after spinal cord injury. J Neurosci 28, 3404-3414.
50. Assis-Nascimento, P., Umland, O., Cepero, M. L. and Liebl, D. J. (2016). A flow cytometric approach to analyzing mature and progenitor endothelial cells following traumatic brain injury. J Neurosci Methods 263, 57-67.

Example 2: Role of EV Mediated Inflammasome Signaling in ALI Following TBI in Human Patients As a follow up to the experiments on mice in Example 1, the role of EV isolated from human TBI patients on inflammasome signaling in human pulmonary endothelial cells was examined.

In a first experiment, serum-derived EV were isolated from TBI and control patients using Total Exosome Isolation kit (Thermofisher). Pulmonary Human Microvascular Endothelial Cells (HMVEC-Lonza) were cultured and plated on a 12-well plate. After confluency was reached, isolated EV from TBI and control patients were delivered (1.94×108 particles/ml) to cells for an incubation period of 4 hours. After incubation cells were harvested with 200 ul of lysis buffer and cell lysates were used for Western Blot analysis.

In a second experiment, serum-derived EV were isolated from TBI and control patients using Total Exosome Isolation kit (Thermofisher). Pulmonary Human Microvascular Endothelial Cells (HMVEC-Lonza) were cultured and plated on a 96-well plate. After confluency was reached, isolated EV from TBI and control patients were delivered (1.94×108 particles/ml) to cells for an incubation period of 3 hours and then 1 additional hour with caspase-1 FAM FLICA (Immunohistochemistry Technologies) with a 1:30 volume to volume ratio. After incubation, media was removed and cells were washed 3 times with apoptosis wash buffer (Immunohistochemistry Technologies). Cells were then co-stained with Hoechst for nuclear staining and Propidium Iodide for cell death. Images were taken using an EVOS microscope and then cells were read under a fluorescent plate reader at an excitation wavelength of 492 nm and an emission wavelength of 520 nm.

Results

As shown in FIG. 10A-10F, delivery of serum-derived EV from TBI patients increased inflammasome protein expression in pulmonary endothelial cells. FIG. 10A-10E showed that caspase-1, ASC, AIM2, and HMGB1 were elevated in PMVEC incubated with TBI-EV for 4 hours as compared to PMVEC incubated with control-EV for 4 hours. Immunoassay results showed a significant increase in IL-1beta expression using Ella simple plex assay (FIG. 10F).

Figure 11A:
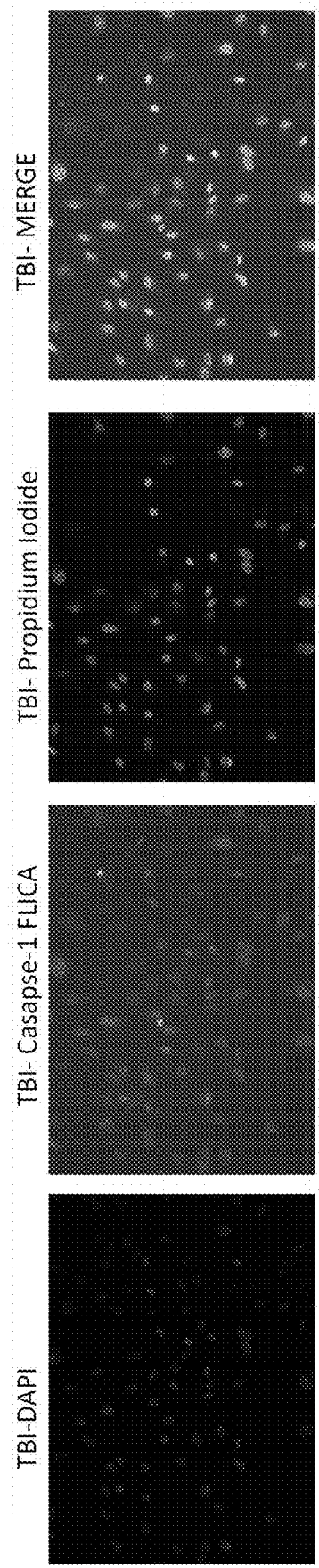
FIG. 11A-11C illustrates delivery of TBI-EV to pulmonary endothelial cells increases immunoreactivity of active caspase-1 and cell death.
Figure 11B:
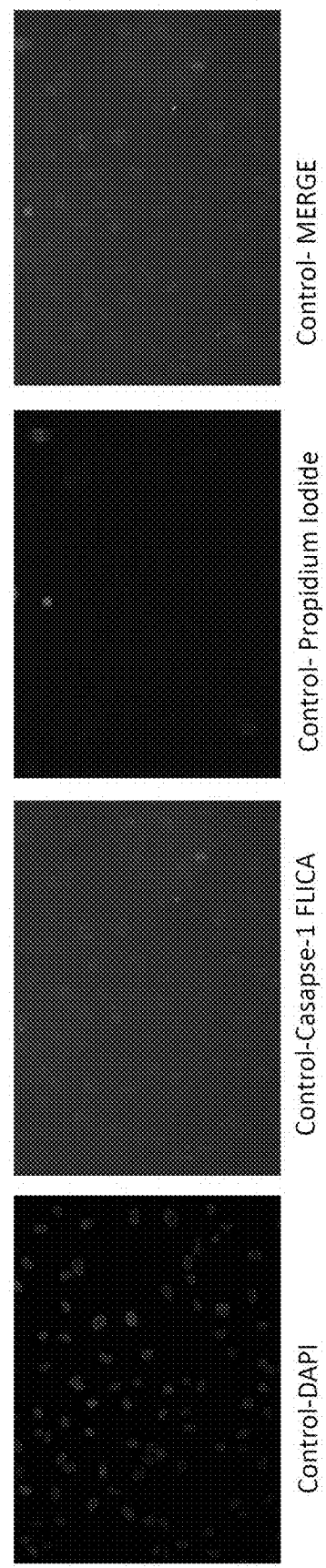
Figure 11C:
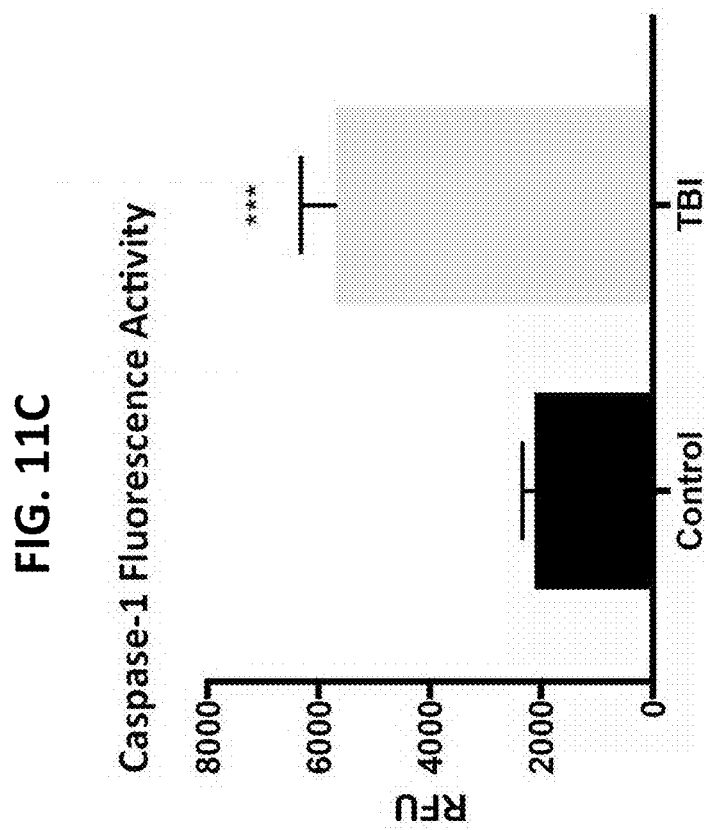

As shown in FIG. 11A-11C, delivery of TBI-EV to pulmonary endothelial cells increased immunoreactivity of caspase-1 and cell death.

Conclusion

These studies provided further evidence for a neural-respiratory-inflammasome axis in which EV released into the circulation after TBI activate the inflammasome in lung target cells contributing to the pathogenesis of ALI.

Example 3: Effect of Use of Humanized Anti-ASC Antibody in an Animal Model of Multiple Sclerosis In order to determine the utility of a humanized, anti-ASC monoclonal antibody in treating MS, said antibody was administered to experimental allergic encephalomyelitis (EAE) mice. EAE is an animal (i.e., rodent) model of MS as described in Höftberger R, Leisser M, Bauer J, Lassmann H (December 2015). "Autoimmune encephalitis in humans: how closely does it reflect multiple sclerosis?". Acta Neuropathol Commun. 3 (1): 80 and Lassman Hans (February 2010). "Acute disseminated encephalomyelitis and multiple sclerosis". Brain. 133: 317-319 and L. Gómezx Vicente et al. Relapse in a paucisymptomatic form of multiple sclerosis in a patient treated with nivolumab, Neuro Oncol (2016) 18 (suppl 4): iv25.

Methods

Induction of EAE and Treatment with IC-100

Active EAE was induced in 2-months old C57BL/6 female mice with myelin oligodendrocyte glycoprotein 35-55 peptide ($MOG_{35-55}$, BioSynthesis) as previously described (Brambilla et al., 2014). Briefly, mice received an intraperitoneal (i.p.) injection of pertussis toxin (dissolved in PBS (350 ng/mouse; day 0), followed by sub-cutaneous administration of $MOG_{35-55}$ (300 ng/mouse; day 1) emulsified in Complete Freund's Adjuvant, and a second i.p. injection of pertussis toxin (350 ng/mouse; day 2). Mice were administered vehicle (0.9% saline) or IC-100 at three different doses (10, 30 and 45 mg/kg) via i.p. injection every 4 days, starting at day 8 after induction of EAE. Clinical symptoms of EAE were assessed daily on a scale of 0 to 6 as follows: 0, no clinical signs; 1, loss of tail tone; 2, flaccid tail; 3, complete hind limb paralysis; 4, complete forelimb paralysis; 5, moribund; 6, dead.

Cell Isolation for Flow Cytometry

Following transcardial perfusion with PBS spinal cords were harvested and placed in cold Hanks' Balanced Salt Solution without $Mg^{2+}$ and $Ca^{2+}$ (HBSS w/o). Samples were manually dissociated into single cell suspensions through a 70 um strainer and washed in HBSS w/o. The spleen samples were spun at 1200 rpm for 10 min at 4° C., supernatants were removed, and red blood cells (RBCs) lysed in 2 ml RBC lysis buffer (eBioscience) according the manufacturer's instructions. Spleen cells were then resuspended in PBS. Cells isolated from the spinal cord were resuspended in flow cytometry buffer (FCB, eBioscience), and incubated with Myelin Removal Beads II (Miltenyi). Myelin was depleted using the LS magnetic columns as described in the manufacturer's protocol (Miltenyi). Similar to the splenocytes, spinal cord cells were resuspended in PBS and stained as described below.

Immunolabeling and Flow Cytometric Analysis

For experiments where Caspase-1 was assessed, the FAM FLICA™ Caspase 1 kit was used (BioRad) according to manufacturer's instructions. Cells were incubated for 30 min at 4° C. in FLICA solution (BioRad), washed with Apoptosis Wash Buffer (BioRad) and resuspended in 1 ml PBS. Samples were then incubated for 30 min at 4° C. with a fixable live/dead stain (Tonbo Biosciences), spun at 1200 rpm for 10 min at 4° C., and removed of the supernatants. Cells were resuspended in 100 ul FACS buffer, blocked with anti-CD16/32 (FcR block, eBioscience) at room temperature for 5 min, immunostained for 30 min at 4° C., and fixed with 1% PFA. Samples were analyzed with a CytoFLEX S flow cytometer equipped with CytExpert 2.1 software (Beckman Coulter). The number of spinal cord leukocytes was determined with 123count eBeads (eBioscience). The number of splenic leukocytes was determined by flow cytometry in combination with trypan blue exclusion counting using a TC20™ Automated Cell Counter (Bio-Rad). A list of flow cytometry antibodies is provided below Table 3.

TABLE 3

Flow Cytometry Antibodies for Use in the Methods Provided Herein.

| Antigen | Color | Dilution | Provider | Catalog # |
|---------|-------|----------|----------|-----------|
| CD45 | FITC | 1:1000 | eBioscience | 11-0451-82 |
| CD45 | PE | 1:1000 | eBioscience | 12-0451-82 |
| CD4 | PE/Cy7 | 1:200 | eBioscience | 25-0042-81 |
| CD8 | Percp-Cy 5.5 | 1:200 | Biolegend | 100734 |
| B220 | PE | 1:200 | Biolegend | 103208 |
| B220 | APC eFluor780 | 1:200 | eBioscience | 47-0452-80 |
| CD11b | APC eFluor780 | 1:200 | eBioscience | 47-0112-82 |
| CD11b | PE/Cy7 | 1:200 | Biolegend | 101215 |
| MHCII | APC | 1:200 | eBioscience | 17-5321-81 |
| Ly6-G | Percp-Cy5.5 | 1:200 | Biolegend | 127616 |
| NK1.1 | APC | 1:200 | Tonbo Biosciences | 20-5941-U025 |
| Live/Dead | Violet 450 | 1:1000 | Tonbo Biosciences | 13-0863-T500 |

Luxol Fast Blue Staining and Quantification of Demyelinated White Matter Volume

Paraformaldehyde (PFA)-fixed segments of the spinal cord were paraffin embedded, sectioned into 10-mm-thick cross sections with a Leica RM 2135 microtome, and stained with luxol fast blue (LFB). Ten serial sections at 50 um intervals were used to estimate the demyelinated white matter volume. Demyelinated areas were outlined with an Olympus BX51 microscope, and demyelinated white matter volume was quantified with Stereoinvestigator software (MicroBrightfield). 3D reconstructions of the demyelinated spinal cord were performed on the same serial sections with Neurolucida software (MBF Bioscience).

Results

Treatment with the Anti-ASC Antibody IC-100 Ameliorates the Functional Outcome in Experimental Autoimmune Encephalomyelitis (EAE)

In order to assess the therapeutic potential of IC-100, EAE was induced with $MOG_{35-55}$ peptide (Brambilla et al., 2014) on two months old female C57BL/6 mice and administered IC-100 or vehicle alone beginning at day 8 post-induction (dpi) of the disease. The administration was repeated every four days till sacrifice, which was set at 35 dpi. Three doses were tested, 10, 30 and 45 mg/Kg.

Figure 12A:
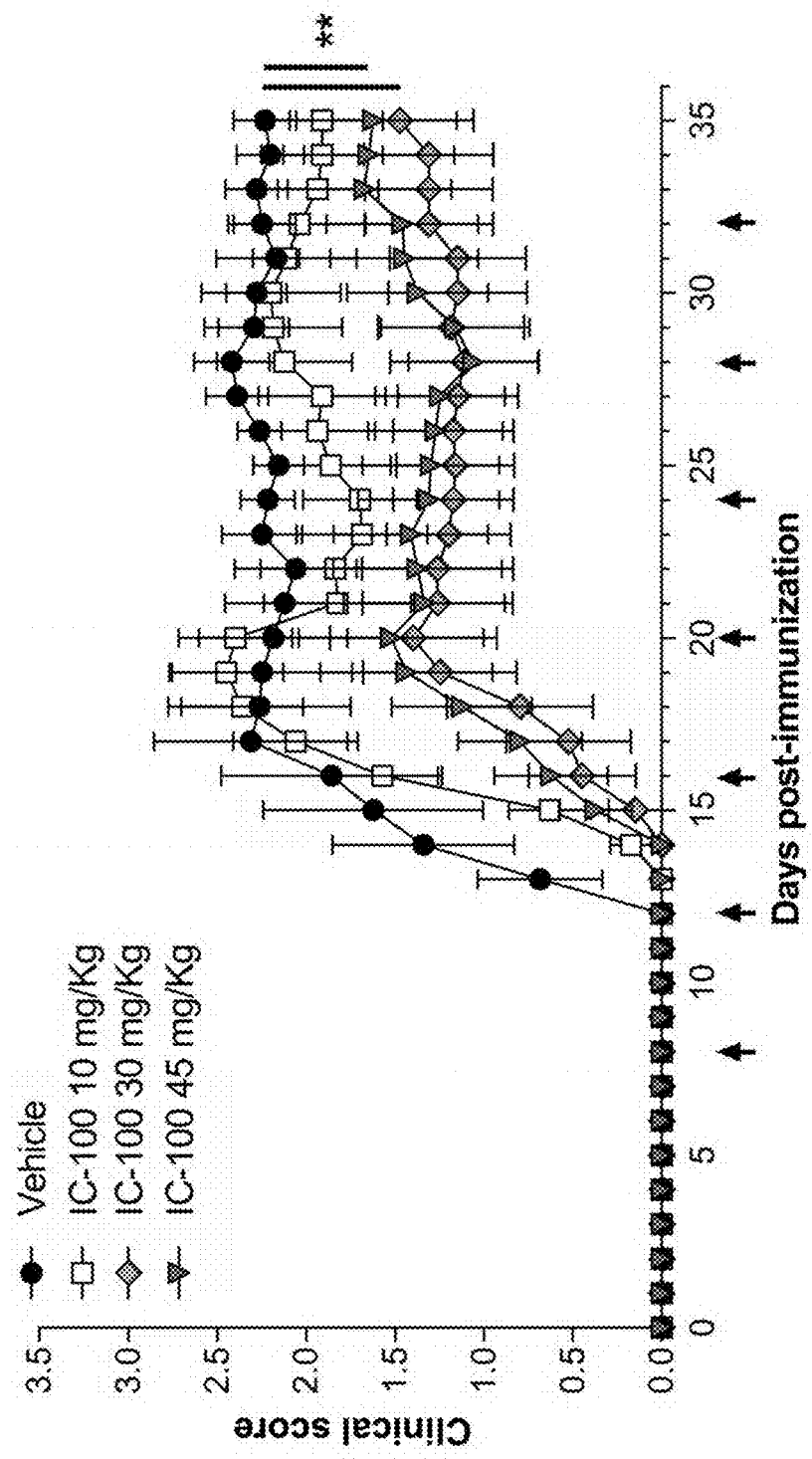

IC-100 significantly improved functional recovery when used at the doses of 30 and 45 mg/Kg, with a robust reduction of the clinical disease scores throughout the duration of the experiment (FIG. 12A). Treatment reduced the average peak clinical scores (FIG. 12B) as well as the overall severity of EAE measured as a reduction in the cumulative disease index (CDI) (FIG. 12C). Mice treated with 30 and 45 mg/Kg IC-100 also showed a tendency to a delayed disease onset (FIG. 12D). No differences in the day the mice reached their peak disease score were observed (FIG. 12E).

Figure 13B:
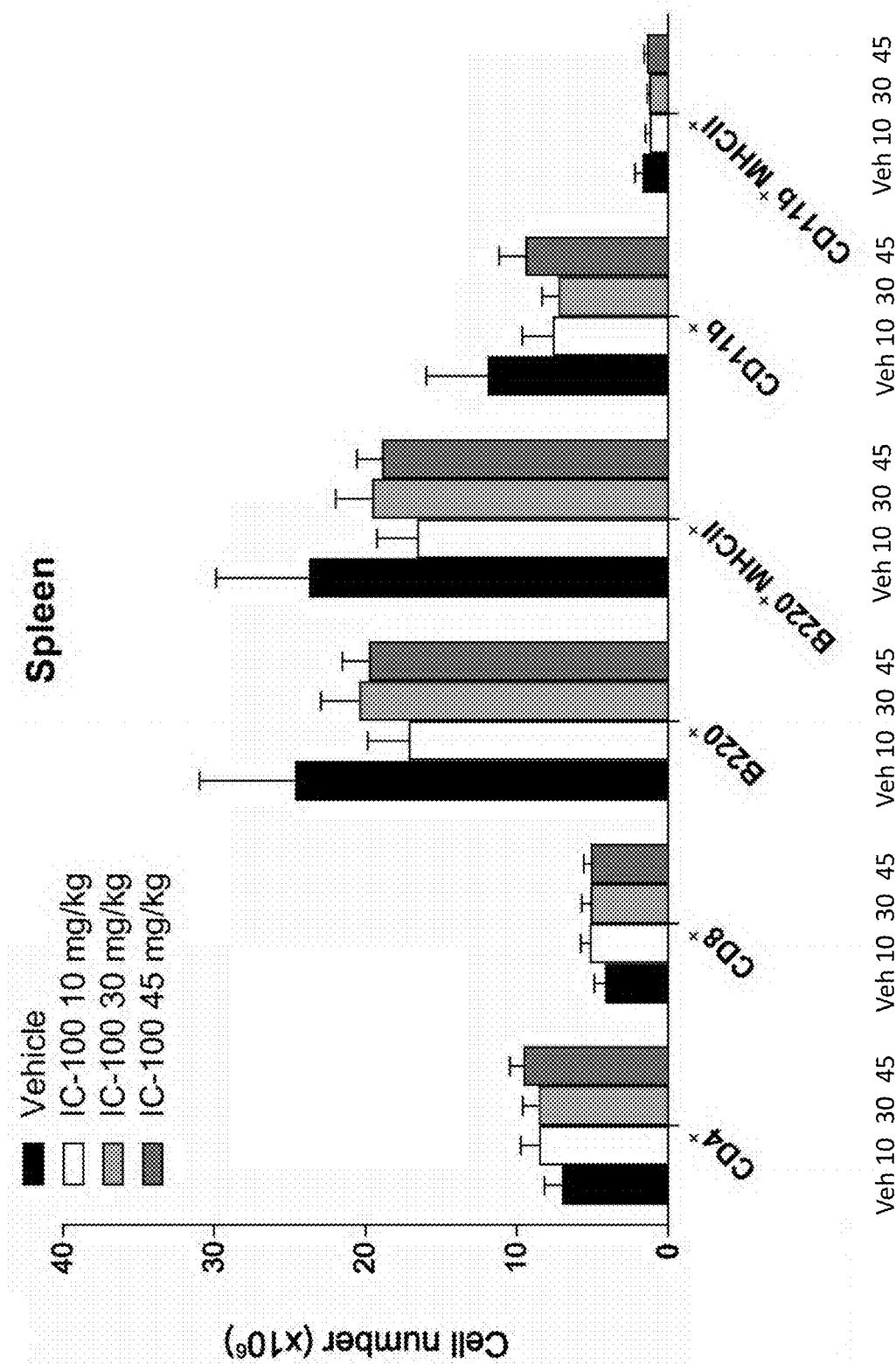

Treatment with the Anti-ASC Antibody IC-100 Reduces the Infiltration of Peripheral Immune Cells into the Spinal Cord Following EAE Initiation, persistence and severity of the clinical symptoms of EAE are directly correlated with the infiltration of immune cells into the spinal cord. To evaluate whether IC-100 affected this process, the immune cell populations isolated from the spinal cord at 35 dpi were profiled by flow cytometry. Treatment with 30 mg/Kg IC-100 significantly reduced the total number of encephalitogenic CD4+ T cells, as well as CD8+ T cells (FIG. 13A), the immune cell populations most crucial in driving EAE pathology. All other immune cell populations showed a clear trend towards a reduction. No differences in cell numbers were observed with any of the IC-100 doses in the spleen, suggesting our treatment did not interfere with the ability of the mice to mount an adequate immune response to the EAE challenge (FIG. 13B).

Figure 14:
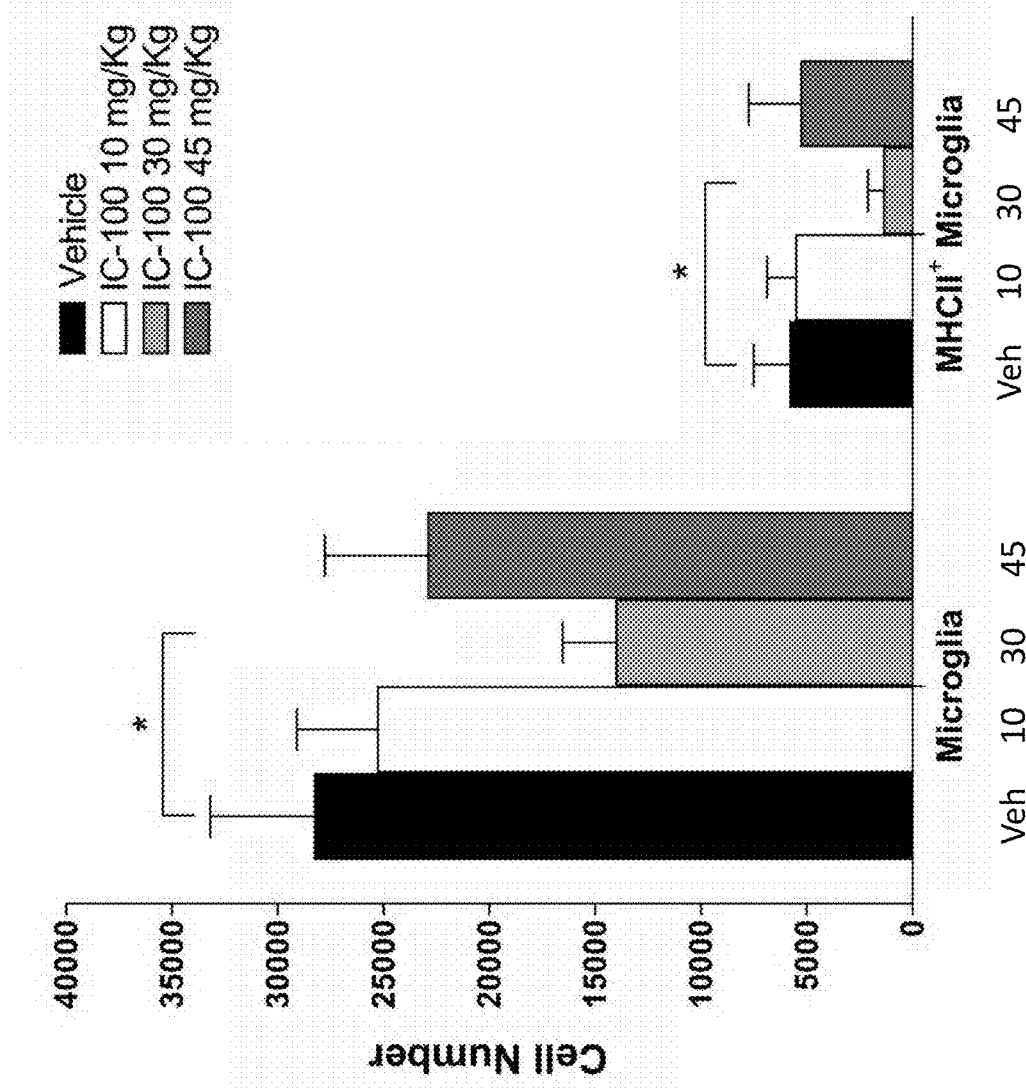
FIG. 14 illustrates that IC-100 treatment reduces peripheral immune cell infiltration into the spinal cord following EAE. Flow cytometric quantification of total microglia and MHCII activated microglia in the spinal cord at 35 dpi after EAE. Results are expressed as average±SEM of 5 mice/group, *p<0.05, Student's t test.

Treatment with the Anti-ASC Antibody IC-100 Reduces the Number and Activation State of Microglia Following EAE Microglia participate in the immune-inflammatory response to CNS disease. As their activation state increases, they proliferate and upregulate surface expression of MHCII. To assess whether IC-100 affected this response, we quantified by flow cytometry the number of total microglia and $MHCII^+$ activated microglia in the spinal cord. Both populations were significantly reduced by treatment with 30 mg/Kg IC-100 indicating that at this dose IC-100 is effective in suppressing microglia activation and microglia-mediated neuroinflammation (see FIG. 14).

REFERENCES

Brambilla R, Morton P D, Ashbaugh J J, Karmally S, Lambertsen K, and Bethea J R (2014) Astrocytes play a key role in EAE pathophysiology by orchestrating in the CNS the inflammatory response of resident and peripheral immune cells and by suppressing remyelination. GLIA, 62:452-457.

Example 4: Use of Humanized Anti-ASC Antibody in an Animal Model of Viral Associated Lung Inflammation The murine coronavirus, mouse hepatitis virus strain A59 (MHV-A59) model is used to study the pathogenesis and the response of the host to coronavirus infections. This model virus has been shown to infect the lungs, liver, spleen, brain and spinal cord, among others. In addition, this model also shows demyelination consistent with a multiple sclerosis-like phenotype (Weiss and Leibowitz 2011). Thus, here we propose to use the MHV-A59 model to test the effects of IC100 in improving the effects of coronavirus infection on survival/recovery and inflammatory cytokine production. We hypothesize that IC100 will bind to ASC to inhibit inflammasome activation as a result of viral infection, resulting in increased survival and decreased production of pro-inflammatory cytokines, including IL-1β, TNF and IL-6.

LITERATURE CITED

He, L., Y. Ding, Q. Zhang, X. Che, Y. He, H. Shen, H. Wang, Z. Li, L. Zhao, J. Geng, Y. Deng, L. Yang, J. Li, J. Cai, L. Qiu, K. Wen, X. Xu and S. Jiang (2006). "Expression of elevated levels of pro-inflammatory cytokines in SARS- CoV-infected ACE2+ cells in SARS patients: relation to the acute lung injury and pathogenesis of SARS." J Pathol 210(3): 288-297.

Kerr, N. A., J. P. de Rivero Vaccari, S. Abbassi, H. Kaur, R. Zambrano, S. Wu, W. D. Dietrich and R. W. Keane (2018). "Traumatic Brain Injury-Induced Acute Lung Injury: Evidence for Activation and Inhibition of a Neural-Respiratory-Inflammasome Axis." J Neurotrauma 35(17): 2067-2076.

Mehta, P., D. F. McAuley, M. Brown, E. Sanchez, R. S. Tattersall, J. J. Manson and U. K. Hlh Across Speciality Collaboration (2020). "COVID-19: consider cytokine storm syndromes and immunosuppression." Lancet 395 (10229): 1033-1034.

Nieto-Torres, J. L., C. Verdia-Baguena, J. M. Jimenez-Guardeno, J. A. Regla-Nava, C. Castano-Rodriguez, R. Fernandez-Delgado, J. Torres, V. M. Aguilella and L. Enjuanes (2015). "Severe acute respiratory syndrome coronavirus E protein transports calcium ions and activates the NLRP3 inflammasome." Virology 485: 330-339.

Ravi Kumar, S., S. Paudel, L. Ghimire, S. Bergeron, S. Cai, R. L. Zemans, G. P. Downey and S. Jeyaseelan (2018). "Emerging Roles of Inflammasomes in Acute Pneumonia." Am J Respir Crit Care Med 197(2): 160-171.

Ruan, Q., K. Yang, W. Wang, L. Jiang and J. Song (2020). "Clinical predictors of mortality due to COVID-19 based on an analysis of data of 150 patients from Wuhan, China." Intensive Care Med.

Tosato, G. and K. D. Jones (1990). "Interleukin-1 induces interleukin-6 production in peripheral blood monocytes." Blood 75(6): 1305-1310.

Weiss, S. R. and J. L. Leibowitz (2011). "Coronavirus pathogenesis." Adv Virus Res 81: 85-164.

Numbered Embodiments of the Disclosure

Other subject matter contemplated by the present disclosure is set out in the following numbered embodiments:

1. A method of treating inflammation in lungs of a patient in need thereof, the method comprising: administering to the patient a composition comprising an agent that inhibits inflammasome signaling, whereby the inflammation in the lungs of the patient is treated.

2. The method of embodiment 1, wherein the inflammation in the lungs is caused by a condition selected from a viral infection, a central nervous system (CNS) injury, a neurodegenerative disease, an autoimmune disease, asthma, chronic obstructive pulmonary disease, cystic fibrosis, interstitial lung disease and acute respiratory distress syndrome.

3. The method of embodiment 2, wherein the CNS injury is selected from the group consisting of traumatic brain injury (TBI), stroke and spinal cord injury (SCI).

4. The method of embodiment 2, wherein the neurodegenerative disease is selected from the group consisting of Alzheimer's disease (AD)/Dementia, amyotrophic lateral sclerosis (ALS), multiple sclerosis (MS) and Parkinson's disease (PD).

5. The method of any one of the above embodiments, wherein the administration of the composition results in inhibition of inflammasome activation in lung cells of the patient.

6. The method of any one of embodiments 1-4, wherein the administration of the composition results in a reduction of caspase-1, nucleotide-binding leucine-rich repeat pyrin domain containing protein 1 (NLRP1), nucleotide-binding leucine-rich repeat pyrin domain containing protein 2 (NLRP2), nucleotide-binding leucine-rich repeat pyrin domain containing protein 3 (NLRP3), NLR family CARD domain-containing protein 4 (NLRC4), caspase-11, X-linked inhibitor of apoptosis protein (XIAP), pannexin-1, Apoptosis-associated Speck-like protein containing a Caspase Activating Recruitment Domain (ASC), interleukin-18 (IL-18), high mobility group box 1 (HMGB1) or absent in melanoma 2 (AIM2) levels in lung cells of the patient as compared to a control, wherein the control is an untreated patient.

7. The method of embodiment 5 or 6, wherein the lung cells are Type II alveolar cells.

8. The method of any one of embodiments 1-5, wherein the administration of the composition results in a reduction in acute lung injury (ALI) as compared to a control, wherein the control is an untreated patient.

9. The method of embodiment 8, wherein the reduction in ALI is evidenced by a reduction in neutrophil infiltration into alveolar and/or interstitial space, reduced or absent alveolar septal thickening or a combination thereof.

10. The method of any one of the above embodiments, wherein the agent is an extracellular vesicle (EV) uptake inhibitor, an antibody that binds to an inflammasome component or a combination thereof.

11. The method of embodiment 10, wherein the EV uptake inhibitor is a compound or an antibody, wherein the antibody is selected from Table 1.

12. The method of any one of embodiments 10-11, wherein the agent is an EV uptake inhibitor in combination with an antibody that binds to an inflammasome component.

13. The method of embodiment 12, wherein the EV uptake inhibitor is a heparin.

14. The method of embodiment 13, wherein the heparin is Enoxaparin.

15. The method of any one of embodiments 10-14, wherein the antibody that binds to an inflammasome component is an antibody that specifically binds to a component of a mammalian AIM2, NLRP1, NLRP2, NLRP3 or NLRC4 inflammasome.

16. The method of embodiment 10 or 15, wherein the inflammasome component is caspase-1, ASC or AIM2.

17. The method of embodiment 16, wherein the inflammasome component is ASC.

18. The method of embodiment 17, wherein the antibody binds to an N-terminal PYRIN-PAAD-DAPIN domain (PYD), C-terminal caspase-recruitment domain (CARD) domain or an epitope derived from the PYD or CARD domain of the ASC protein.

19. The method of embodiment 17, wherein the antibody binds to an amino acid having at least 85% sequence identity with an amino acid sequence selected from the group consisting of SEQ ID NO: 1 and SEQ ID NO: 2.

20. The method of any one of embodiments 17-19, wherein the antibody inhibits ASC activity in the lungs of the patient.

21. The method of any one of the above embodiments, wherein the composition is formulated with a pharmaceutically acceptable carrier or diluent.

22. The method of any one of the above embodiments, wherein the composition is administered intracerebroventricularly, intraperitoneally, intravenously, intranasally or by inhalation.

23. A method of treating inflammation in lungs of a patient that has been subjected to a viral infection, a central nervous system (CNS) injury, the method comprising: administering to the patient a composition comprising an agent that inhibits inflammasome signaling, whereby the inflammation in the lungs of the patient is treated.

24. The method of embodiment 23, wherein the CNS injury is selected from the group consisting of traumatic brain injury (TBI), stroke and spinal cord injury (SCI).

25. The method of any one of embodiments 23-24, wherein the administration of the composition results in inhibition of inflammasome activation in lung cells of the patient.

26. The method of any one of embodiments 23-24, wherein the administration of the composition results in a reduction of caspase-1, NLRP1, NLRP2, NLRP3, NLRC4, caspase-11, XIAP, pannexin-1, Apoptosis-associated Speck-like protein containing a Caspase Activating Recruitment Domain (ASC), interleukin-18 (IL-18), high mobility group box 1 (HMGB1) or absent in melanoma 2 (AIM2) levels in lung cells of the patient as compared to a control, wherein the control is an untreated patient.

27. The method of embodiment 25 or 26, wherein the lung cells are Type II alveolar cells.

28. The method of any one of embodiments 23-27, wherein the administration of the composition results in a reduction in acute lung injury (ALI) as compared to a control, wherein the control is an untreated patient.

29. The method of embodiment 28, wherein the reduction in ALI is evidenced by a reduction in neutrophil infiltration into alveolar and/or interstitial space, reduced or absent alveolar septal thickening or a combination thereof.

30. The method of any one of embodiments 23-29, wherein the agent is an extracellular vesicle (EV) uptake inhibitor, an antibody that binds to an inflammasome component or a combination thereof.

31. The method of embodiment 30, wherein the EV uptake inhibitor is a compound or an antibody, wherein the antibody is selected from Table 1.

32. The method of any one of embodiments 30-31, wherein the agent is an EV uptake inhibitor in combination with an antibody that binds to an inflammasome component.

33. The method of embodiment 32, wherein the EV uptake inhibitor is a heparin.

34. The method of embodiment 33, wherein the heparin is Enoxaparin.

35. The method of any one of embodiments 30-34, wherein the antibody that binds to an inflammasome component is an antibody that specifically binds to a component of a mammalian AIM2, NLRP1, NLRP2, NLRP3 or NLRC4 inflammasome.

36. The method of embodiment 30 or 35, wherein the inflammasome component is caspase-1, ASC or AIM2.

37. The method of embodiment 36, wherein the inflammasome component is ASC.

38. The method of embodiment 37, wherein the antibody binds to the PYD, CARD domain or an epitope derived from the PYD or CARD domain of the ASC protein.

39. The method of embodiment 37, wherein the antibody binds to an amino acid having at least 85% sequence identity with an amino acid sequence selected from the group consisting of SEQ ID NO: 1 and SEQ ID NO: 2.

40. The method of any one of embodiments 37-39, wherein the antibody inhibits ASC activity in the lungs of the patient.

41. The method of any one of embodiments 23-40, wherein the composition is formulated with a pharmaceutically acceptable carrier or diluent.

42. The method of any one of embodiments 23-41, wherein the composition is administered intracerebroventricularly, intraperitoneally, intravenously, intranasally or by inhalation.

43. A monoclonal antibody or an antibody fragment thereof that binds to Apoptosis-associated Speck-like protein containing a Caspase Activating Recruitment Domain (ASC), wherein the antibody or the antibody fragment binds specifically to an epitope of ASC, wherein the epitope comprises or consists of the amino acid sequence of SEQ ID NO: 5 or 5-10, 10-15 or 15-20 amino acids of SEQ ID NO: 5.

44. A monoclonal antibody or an antibody fragment thereof that binds specifically to ASC, wherein the antibody or the antibody fragment comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3.

45. A monoclonal antibody or an antibody fragment thereof that binds specifically to ASC, wherein the antibody or the antibody fragment comprises a light chain variable (VL) region and a heavy chain variable (VH) region, wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3.

46. A monoclonal antibody or an antibody fragment thereof that binds specifically to ASC, wherein the antibody or the antibody fragment comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8, or a variant thereof having at least one amino acid substitution in HCDR1, HCDR2, and/or HCDR3; and wherein the VL region amino acid sequence comprises LCDR1 of SEQ ID NO: 12, LCDR2 of SEQ ID NO: 13 and LCDR3 of SEQ ID NO: 14, or a variant thereof having at least one amino acid substitution in LCDR1, LCDR2, and/or LCDR3.

47. The monoclonal antibody or the antibody fragment thereof of embodiment 44, wherein the VH region amino acid sequence comprises SEQ ID NO: 18, 19, 20, 21, 22, or an amino acid sequence that is at least 95%, 96%, 97%, 98% or 99% identical to the amino acid sequence of SEQ ID NO: 18, 19, 20, 21, or 22.

48. The monoclonal antibody or the antibody fragment thereof of embodiment 45, wherein the VL region amino acid sequence comprises SEQ ID NO: 28, 29, 30, 31, or an amino acid sequence that is at least 95%, 96%, 97%, 98% or 99% identical to the amino acid sequence of SEQ ID NO: 28, 29, 30 or 31.

49. The monoclonal antibody or the antibody fragment thereof of embodiment 46, wherein the VH region amino acid sequence comprises SEQ ID NO: 18, 19, 20, 21, 22, or an amino acid sequence that is at least 95%, 96%, 97%, 98% or 99% identical to the amino acid sequence of SEQ ID NO: 18, 19, 20, 21 or 22; and wherein the VL region amino acid sequence comprises SEQ ID NO: 28, 29, 30, 31, or an amino acid sequence that is at least 95%, 96%, 97%, 98% or 99% identical to the amino acid sequence of SEQ ID NO: 28, 29, 30 or 31.

50. The monoclonal antibody or the antibody fragment thereof of embodiment 46, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 28 or an amino acid sequence that is at least 95%, 96%, 97%, 98% or 99% identical to the amino acid sequence of SEQ ID NO: 28.

51. The monoclonal antibody or the antibody fragment thereof of embodiment 46, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 29 or an amino acid sequence that is at least 95%, 96%, 97%, 98% or 99% identical to the amino acid sequence of SEQ ID NO: 29.

52. The monoclonal antibody or the antibody fragment thereof of embodiment 46, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 30 or an amino acid sequence that is at least 95%, 96%, 97%, 98% or 99% identical to the amino acid sequence of SEQ ID NO: 30.

53. The monoclonal antibody or the antibody fragment thereof of embodiment 46, wherein the VH region amino acid sequence comprises SEQ ID NO: 18, or an amino acid sequence that is at least 95%, 96%, 97%, 98% or 99% identical to the amino acid sequence of SEQ ID NO: 18; and wherein the VL region amino acid sequence comprises SEQ ID NO: 31 or an amino acid sequence that is at least 95%, 96%, 97%, 98% or 99% identical to the amino acid sequence of SEQ ID NO: 31.

54. The monoclonal antibody or the antibody fragment thereof of embodiment 46, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 28 or an amino acid sequence that is at least 95%, 96%, 97%, 98% or 99% identical to the amino acid sequence of SEQ ID NO: 28.

55. The monoclonal antibody or the antibody fragment thereof of embodiment 46, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 29 or an amino acid sequence that is at least 95%, 96%, 97%, 98% or 99% identical to the amino acid sequence of SEQ ID NO: 29.

56. The monoclonal antibody or the antibody fragment thereof of embodiment 46, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 30 or an amino acid sequence that is at least 95%, 96%, 97%, 98% or 99% identical to the amino acid sequence of SEQ ID NO: 30.

57. The monoclonal antibody or the antibody fragment thereof of embodiment 46, wherein the VH region amino acid sequence comprises SEQ ID NO: 19, or an amino acid sequence that is at least 95%, 96%, 97%, 98% or 99% identical to the amino acid sequence of SEQ ID NO: 19; and wherein the VL region amino acid sequence comprises SEQ ID NO: 31 or an amino acid sequence that is at least 95%, 96%, 97%, 98% or 99% identical to the amino acid sequence of SEQ ID NO: 31.

58. The monoclonal antibody or the antibody fragment thereof of embodiment 46, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 28 or an amino acid sequence that is at least 95%, 96%, 97%, 98% or 99% identical to the amino acid sequence of SEQ ID NO: 28.

59. The monoclonal antibody or the antibody fragment thereof of embodiment 46, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 29 or an amino acid sequence that is at least 95%, 96%, 97%, 98% or 99% identical to the amino acid sequence of SEQ ID NO: 29.

60. The monoclonal antibody or the antibody fragment thereof of embodiment 46, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 30 or an amino acid sequence that is at least 95%, 96%, 97%, 98% or 99% identical to the amino acid sequence of SEQ ID NO: 30.

61. The monoclonal antibody or the antibody fragment thereof of embodiment 46, wherein the VH region amino acid sequence comprises SEQ ID NO: 20, or an amino acid sequence that is at least 95%, 96%, 97%, 98% or 99% identical to the amino acid sequence of SEQ ID NO: 20; and wherein the VL region amino acid sequence comprises SEQ ID NO: 31 or an amino acid sequence that is at least 95%, 96%, 97%, 98% or 99% identical to the amino acid sequence of SEQ ID NO: 31.

62. The monoclonal antibody or the antibody fragment thereof of embodiment 46, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 28 or an amino acid sequence that is at least 95%, 96%, 97%, 98% or 99% identical to the amino acid sequence of SEQ ID NO: 28.

63. The monoclonal antibody or the antibody fragment thereof of embodiment 46, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 29 or an amino acid sequence that is at least 95%, 96%, 97%, 98% or 99% identical to the amino acid sequence of SEQ ID NO: 29.

64. The monoclonal antibody or the antibody fragment thereof of embodiment 46, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 30 or an amino acid sequence that is at least 95%, 96%, 97%, 98% or 99% identical to the amino acid sequence of SEQ ID NO: 30.

65. The monoclonal antibody or the antibody fragment thereof of embodiment 46, wherein the VH region amino acid sequence comprises SEQ ID NO: 21, or an amino acid sequence that is at least 95%, 96%, 97%, 98% or 99% identical to the amino acid sequence of SEQ ID NO: 21; and wherein the VL region amino acid sequence comprises SEQ ID NO: 31 or an amino acid sequence that is at least 95%, 96%, 97%, 98% or 99% identical to the amino acid sequence of SEQ ID NO: 31.

66. The monoclonal antibody or the antibody fragment thereof of embodiment 46, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 28 or an amino acid sequence that is at least 95%, 96%, 97%, 98% or 99% identical to the amino acid sequence of SEQ ID NO: 28.

67. The monoclonal antibody or the antibody fragment thereof of embodiment 46, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 29 or an amino acid sequence that is at least 95%, 96%, 97%, 98% or 99% identical to the amino acid sequence of SEQ ID NO: 29.

68. The monoclonal antibody or the antibody fragment thereof of embodiment 46, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 30 or an amino acid sequence that is at least 95%, 96%, 97%, 98% or 99% identical to the amino acid sequence of SEQ ID NO: 30.

69. The monoclonal antibody or the antibody fragment thereof of embodiment 46, wherein the VH region amino acid sequence comprises SEQ ID NO: 22, or an amino acid sequence that is at least 95%, 96%, 97%, 98% or 99% identical to the amino acid sequence of SEQ ID NO: 22; and wherein the VL region amino acid sequence comprises SEQ ID NO: 31 or an amino acid sequence that is at least 95%, 96%, 97%, 98% or 99% identical to the amino acid sequence of SEQ ID NO: 31.

70. The monoclonal antibody or the antibody fragment thereof of any one of embodiments 44-69, wherein the ASC is human ASC protein.

71. The monoclonal antibody fragment of any one of embodiments 44-70, wherein the antibody fragment is an Fab, an F(ab')$_2$, an Fab', an scFv, a single domain antibody, a diabody or a single chain camelid antibody.

72. The monoclonal antibody or the antibody fragment thereof of any one of embodiments 44-71, wherein the monoclonal antibody or the antibody fragment thereof is human, humanized or chimeric.

73. An isolated nucleic acid molecule encoding the monoclonal antibody or the antibody fragment thereof of any one of embodiments 44-72.

74. An expression vector comprising the nucleic acid molecule of embodiment 73.

75. The expression vector of embodiment 32, wherein the nucleic acid molecule is operatively linked to regulatory sequences suitable for expression of the nucleic acid segment in a host cell.

76. A recombinant host cell comprising the expression vector of embodiment 74 or 75.

77. A method for producing an antibody or an antibody fragment that binds specifically to ASC, the method comprising: culturing a recombinant host cell comprising the expression vector of embodiment 74 or 75 under conditions whereby the nucleic acid molecule is expressed, thereby producing the monoclonal antibody or the antibody fragment thereof that binds specifically to ASC.

78. A pharmaceutical composition comprising the monoclonal antibody or the antibody fragment thereof of any one of embodiments 44-72, and a pharmaceutically acceptable carrier, diluent or excipient.

79. A method of treating inflammation in a subject, the method comprises administering to the subject a therapeutically effective amount of the monoclonal antibody or the antibody fragment thereof of any one of embodiments 44-72, thereby treating the inflammation in the subject.

80. The method of embodiment 79, wherein the administering the monoclonal antibody or the antibody fragment thereof reduces levels of at least inflammatory cytokine.

81. The method of embodiment 80, wherein the inflammation is an inflammasome-related inflammation.

82. The method of embodiment 81, wherein the inflammasome-related inflammation is associated with a viral infection, a central nervous system (CNS) injury, an autoimmune or neurodegenerative disease.

83. The method of embodiment 82, wherein the CNS injury selected from the group consisting of traumatic brain injury (TBI), stroke and spinal cord injury (SCI).

84. The method of embodiment 82, wherein the autoimmune or neurodegenerative disease is amyotrophic lateral sclerosis (ALS), Alzheimer's disease, Parkinson's disease, muscular dystrophy (MD) or multiple sclerosis (MS).

85. The method of any one of embodiments 79-84, wherein the administration of the monoclonal antibody or the antibody fragment thereof results in inhibition of inflammasome activation in the subject.

86. The method of any one of embodiments 79-84, wherein the administration of the monoclonal antibody or the antibody fragment thereof results in a reduction in the activity of ASC as compared to a control.

87. The method of embodiment 86, wherein the control is an untreated subject.

88. The method of any one of embodiments 79-87, wherein the administration is intracerebroventricularly, intraperitoneally, intravenously or by inhalation.

89. A method of treating multiple sclerosis (MS) in a subject, the method comprises administering to the subject a therapeutically effective amount of the monoclonal antibody or the antibody fragment thereof of any one of embodiments 44-72, thereby treating MS in the subject.

90. The method of embodiment 89, wherein the administering the monoclonal antibody or the antibody fragment thereof reduces levels of at least inflammatory cytokine.

91. The method of embodiment 89, wherein the administration of the monoclonal antibody or the antibody fragment thereof results in inhibition of inflammasome activation in the subject.

92. The method of any one of embodiments 89-91, wherein the administration of the monoclonal antibody or the antibody fragment thereof results in a reduction in the activity of ASC as compared to a control.

93. The method of embodiment 92, wherein the control is an untreated subject.

94. The method of any one of embodiments 89-93, wherein the administration is intracerebroventricularly, intraperitoneally, intravenously, intranasally or by inhalation.

95. The method of any one of embodiments 2, 23 or 82, wherein said viral infection is caused by a coronavirus or an influenza virus.

96. The method of embodiment 95, wherein said coronavirus is a SARS or MERS virus.

97. The method of embodiment 96, wherein said SARS coronavirus is SARS-CoV or SARS-CoV-2.

98. The method of embodiment 95, wherein the influenza virus is a pandemic influenza.

99. The method of embodiment 98, wherein the pandemic influenza virus is influenza A H5N1 (avian influenza) or influenza A H1N1 (swine flu).

100. The method of embodiment 95, wherein the viral infection causes acute respiratory distress syndrome (ARDS).

The various embodiments described above can be combined to provide further embodiments. All of the U.S. patents, U.S. patent application publications, U.S. patent application, foreign patents, foreign patent application and non-patent publications referred to in this specification are incorporated herein by reference, in their entirety. Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for treating a patient suffering from a coronavirus infection, said method comprising administering to the patient an effective amount of a composition comprising a monoclonal antibody or fragment thereof that comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8; and wherein the VL region amino acid sequence comprises LCDR1 of SEQ ID NO: 12, LCDR2 of SEQ ID NO: 13 and LCDR3 of SEQ ID NO: 14 that inhibits inflammasome signaling, whereby inflammation in the lungs of the patient is ameliorated or reversed.

2. The method of claim 1, wherein the coronavirus is SARS-CoV-2.

3. The method of claim 1, wherein the inflammation in the lungs results from a cytokine storm.

4. The method of claim 1, wherein the lung inflammation presents as Acute Respiratory Distress Syndrome (ARDS).

5. The method of claim 1, wherein the monoclonal antibody or fragment thereof comprises a VH region amino acid sequence comprising SEQ ID NO: 19 and a VL region amino acid sequence comprising SEQ ID NO: 30.

6. A method for treating a lung inflammation resulting from a coronavirus infection, said method comprising administering an effective amount of a composition comprising a monoclonal antibody or fragment thereof that comprises a heavy chain variable (VH) region and a light chain variable (VL) region, wherein the VH region amino acid sequence comprises HCDR1 of SEQ ID NO: 6, HCDR2 of SEQ ID NO: 7 and HCDR3 of SEQ ID NO: 8; and wherein the VL region amino acid sequence comprises LCDR1 of SEQ ID NO: 12, LCDR2 of SEQ ID NO: 13 and LCDR3 of SEQ ID NO: 14 that inhibits inflammasome signaling, whereby the inflammation in the lungs of the patient is ameliorated or reversed.

7. The method of claim 6, wherein the coronavirus is SARS-CoV-2.

8. The method of claim 6, wherein the inflammation in the lungs results from a cytokine storm.

9. The method of claim 6, wherein the lung inflammation presents as Acute Respiratory Distress Syndrome (ARDS).

10. The method of claim 6, wherein the monoclonal antibody or fragment thereof comprises a VH region amino acid sequence comprising SEQ ID NO: 19 and a VL region amino acid sequence comprising SEQ ID NO: 30.

* * * * *